(12) United States Patent
Murray

(10) Patent No.: US 10,307,185 B2
(45) Date of Patent: Jun. 4, 2019

(54) REVISION CONNECTORS, SYSTEMS, AND METHODS THEREOF

(71) Applicant: GLOBUS MEDICAL, INC., Audubon, PA (US)

(72) Inventor: Patrick Murray, Collegeville, PA (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 15/613,769

(22) Filed: Jun. 5, 2017

(65) Prior Publication Data

US 2017/0281243 A1    Oct. 5, 2017

Related U.S. Application Data

(63) Continuation-in-part of application No. 15/346,199, filed on Nov. 8, 2016, which is a continuation-in-part of application No. 15/228,019, filed on Aug. 4, 2016, which is a continuation-in-part of application No. 15/083,467, filed on Mar. 29, 2016, now Pat. No. 9,980,755.

(51) Int. Cl.
*A61B 17/70* (2006.01)
*A61B 90/00* (2016.01)

(52) U.S. Cl.
CPC ...... *A61B 17/7049* (2013.01); *A61B 17/7004* (2013.01); *A61B 17/705* (2013.01); *A61B 17/7007* (2013.01); *A61B 17/7032* (2013.01); *A61B 17/7052* (2013.01); *A61B 17/7011* (2013.01); *A61B 17/7037* (2013.01); *A61B 2090/037* (2016.02)

(58) Field of Classification Search
CPC .................................................. A61B 17/705
See application file for complete search history.

(56) References Cited

U.S. PATENT DOCUMENTS

| | | |
|---|---|---|
| 5,419,522 A | 5/1995 | Luecke et al. |
| 5,601,552 A | 2/1997 | Cotrel |
| 5,688,273 A | 11/1997 | Errico et al. |
| 5,947,966 A | 9/1999 | Drewry et al. |
| 6,113,600 A | 9/2000 | Drummond et al. |
| 6,136,003 A | 10/2000 | Hoeck et al. |
| 6,171,311 B1 | 1/2001 | Richelsoph |
| 6,328,740 B1 | 12/2001 | Richelsoph |
| 6,402,751 B1 | 6/2002 | Hoeck et al. |
| 6,524,310 B1 | 2/2003 | Lombardo et al. |
| 6,602,253 B2 | 8/2003 | Richelsoph et al. |
| 6,872,208 B1 | 3/2005 | McBride et al. |
| 6,958,066 B2 | 10/2005 | Richelsoph et al. |
| 7,029,474 B2 | 4/2006 | Richelsoph et al. |
| 7,175,622 B2 | 2/2007 | Farris |
| 7,344,537 B1 | 3/2008 | Mueller |
| 7,585,314 B2 | 9/2009 | Taylor et al. |
| 7,678,112 B2 | 3/2010 | Rezach |

(Continued)

FOREIGN PATENT DOCUMENTS

FR    3006886 A1    12/2014

*Primary Examiner* — Jan Christopher L Merene

(57) ABSTRACT

Connector assemblies, systems, and methods thereof. A modular connector has a first end that clamps to a first rod in an existing construct and a second end having a modular connection point configured to connect a second rod in a new construct such that the new construct can be extended from the existing construct.

16 Claims, 54 Drawing Sheets

(56) References Cited

U.S. PATENT DOCUMENTS

| | | |
|---|---|---|
| 7,699,872 B2 | 4/2010 | Farris et al. |
| 7,717,938 B2 | 5/2010 | Kim et al. |
| 7,744,632 B2 | 6/2010 | Usher |
| D622,395 S | 8/2010 | Iott et al. |
| 7,806,912 B2 | 10/2010 | Lawton et al. |
| 7,842,071 B2 | 11/2010 | Hawkes |
| 7,909,854 B2 | 3/2011 | Schwab |
| 7,942,901 B2 | 5/2011 | Rezach |
| 7,976,567 B2 | 7/2011 | Null et al. |
| 7,993,371 B2 | 8/2011 | Farris |
| 8,021,399 B2 | 9/2011 | Ritland |
| 8,097,022 B2 | 1/2012 | Marik |
| 8,236,028 B2 | 8/2012 | Kalfas et al. |
| 8,246,657 B1 | 8/2012 | Samuel |
| 8,252,030 B2 | 8/2012 | Iott et al. |
| 8,313,515 B2 | 11/2012 | Brennan et al. |
| 8,337,527 B2 | 12/2012 | Hawkins et al. |
| 8,337,532 B1 | 12/2012 | McLean et al. |
| 8,372,119 B2 | 2/2013 | Kim et al. |
| 8,414,623 B2 | 4/2013 | Baker et al. |
| 8,506,602 B2 | 8/2013 | Slivka et al. |
| 8,518,085 B2 | 8/2013 | Winslow et al. |
| 8,523,906 B2 | 9/2013 | McLean et al. |
| 8,548,080 B2 | 10/2013 | Chang et al. |
| 8,628,559 B2 | 1/2014 | Iott et al. |
| 8,641,739 B2 | 2/2014 | McLean et al. |
| 8,715,323 B2 | 5/2014 | Ballard et al. |
| 88,721,689 | 5/2014 | Butler et al. |
| 8,758,411 B1 * | 6/2014 | Rayon .......... A61B 17/7004 606/259 |
| 8,771,319 B2 | 7/2014 | Prajapati |
| 8,845,694 B2 | 9/2014 | Ritland |
| 8,852,237 B2 | 10/2014 | Kalfas et al. |
| 8,870,923 B2 | 10/2014 | Richelsoph |
| 8,882,803 B2 | 11/2014 | Iott et al. |
| 8,920,471 B2 | 12/2014 | Barrus et al. |
| 8,998,961 B1 | 4/2015 | Ziemek et al. |
| 9,113,961 B2 | 8/2015 | Larroque-Lahitette |
| 9,220,541 B1 | 12/2015 | Dant et al. |
| 9,283,003 B2 | 3/2016 | Iott et al. |
| 2003/0028192 A1 * | 2/2003 | Schar .......... A61B 17/7052 606/252 |
| 2004/0162558 A1 | 8/2004 | Hegde et al. |
| 2005/0055026 A1 | 3/2005 | Biedermann et al. |
| 2005/0228378 A1 | 10/2005 | Kalfas et al. |
| 2006/0079892 A1 * | 4/2006 | Roychowdhury . A61B 17/7044 606/253 |
| 2006/0233597 A1 | 10/2006 | Ensign et al. |
| 2006/0241602 A1 | 10/2006 | Jackson |
| 2007/0270817 A1 | 11/2007 | Rezach |
| 2008/0262553 A1 | 10/2008 | Hawkins et al. |
| 2009/0264931 A1 | 10/2009 | Miller et al. |
| 2010/0280552 A1 * | 11/2010 | Lee .......... A61B 17/705 606/250 |
| 2010/0298884 A1 * | 11/2010 | Faizan .......... A61B 17/705 606/266 |
| 2011/0087289 A1 | 4/2011 | Pham et al. |
| 2011/0106166 A1 | 5/2011 | Keyer et al. |
| 2011/0245872 A1 * | 10/2011 | Nilsson .......... A61B 17/7049 606/250 |
| 2013/0006307 A1 * | 1/2013 | Robinson .......... A61B 17/7052 606/252 |
| 2013/0197556 A1 | 8/2013 | Shelton, IV et al. |
| 2014/0018858 A1 | 1/2014 | Laeng et al. |
| 2014/0094858 A1 | 4/2014 | Picetti et al. |
| 2014/0121706 A1 | 5/2014 | Iott et al. |
| 2014/0172017 A1 * | 6/2014 | McLean .......... A61B 17/7011 606/271 |
| 2014/0251042 A1 | 9/2014 | Asselin et al. |
| 2014/0277163 A1 * | 9/2014 | Kretzer .......... A61B 17/7049 606/278 |
| 2015/0057708 A1 | 2/2015 | Ballard et al. |
| 2015/0119941 A1 | 4/2015 | Daniels et al. |
| 2015/0359568 A1 | 12/2015 | Rezach |

\* cited by examiner

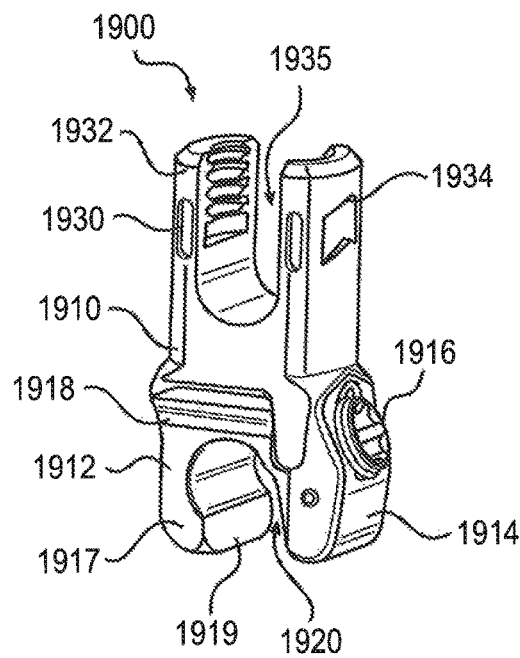
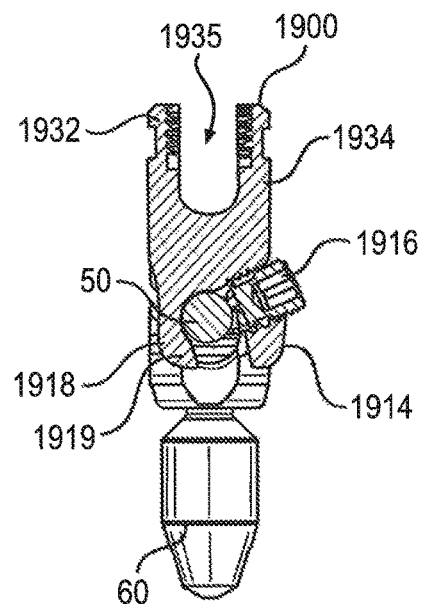
FIG. 44   FIG. 45
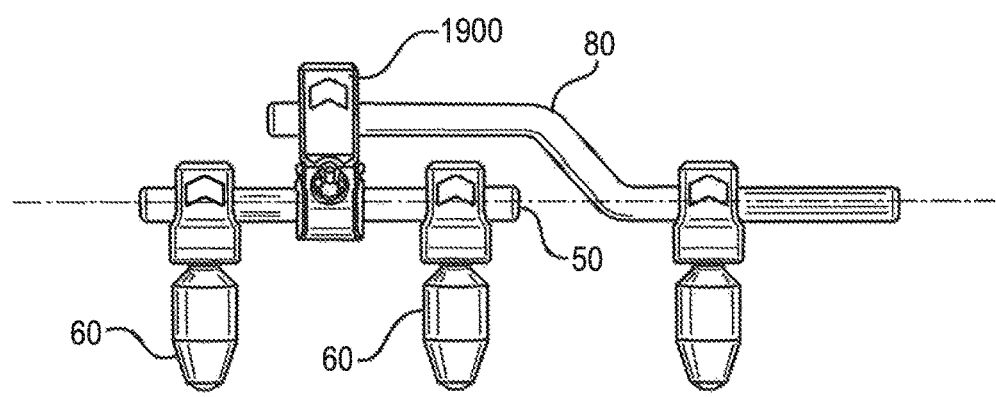
FIG. 46

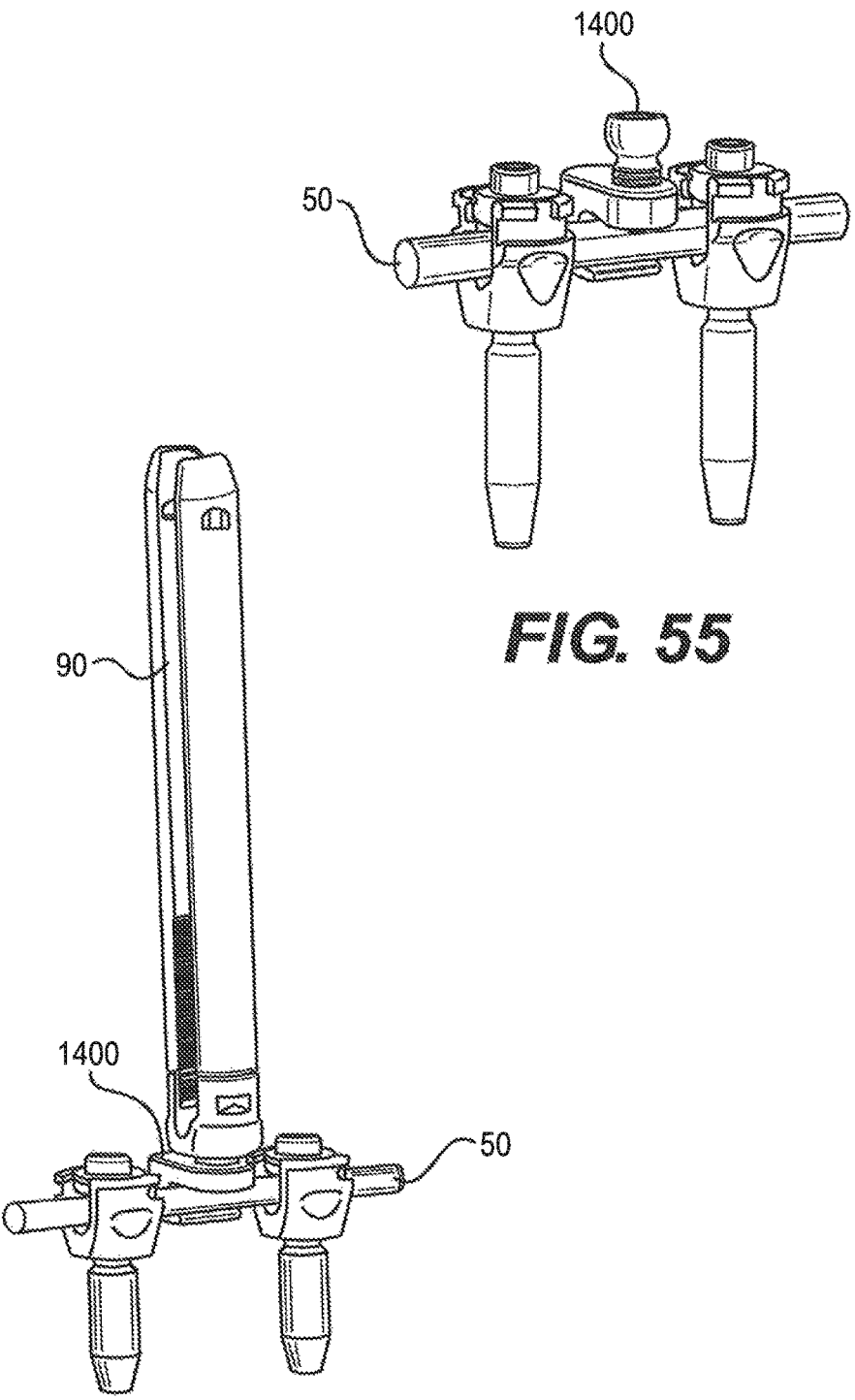

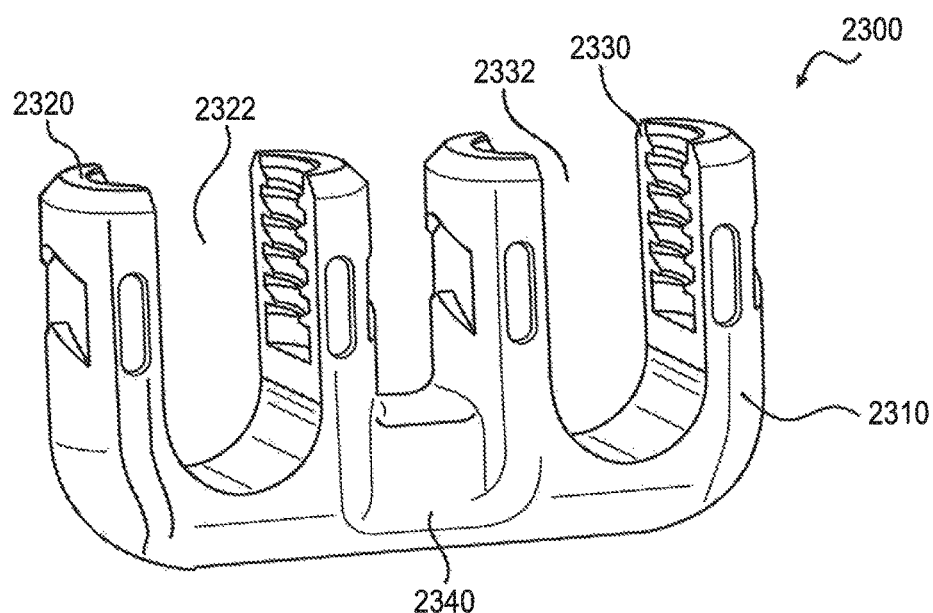
FIG. 62
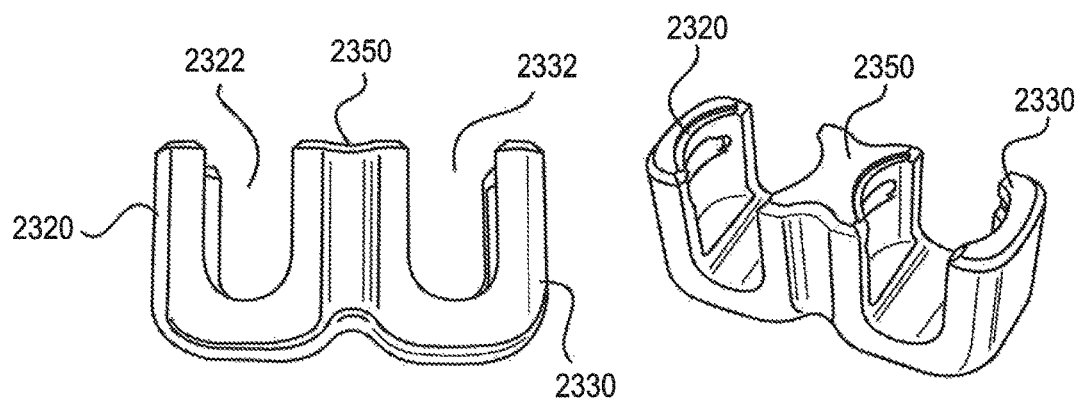
FIG. 63  FIG. 64

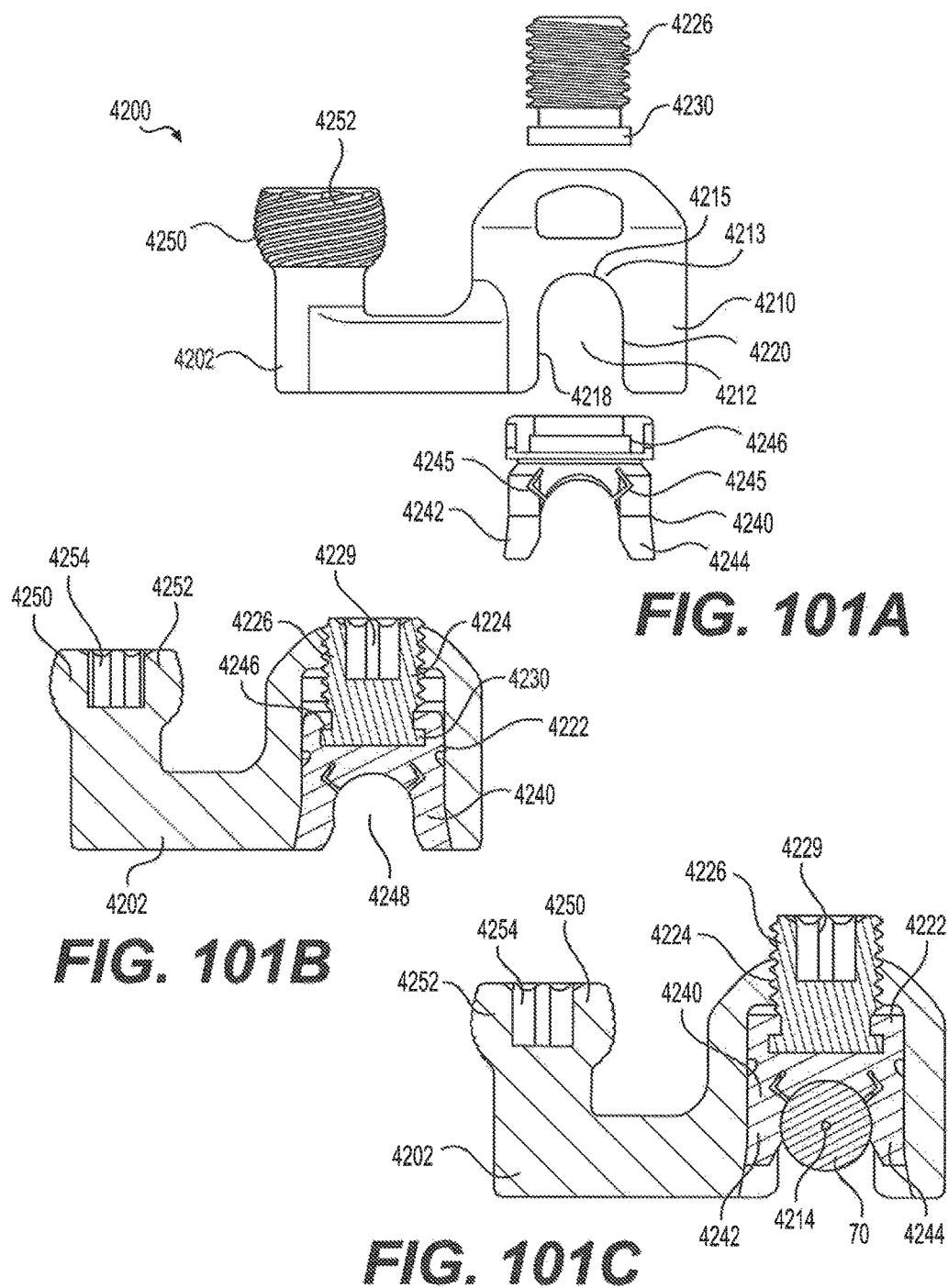

REVISION CONNECTORS, SYSTEMS, AND METHODS THEREOF

CROSS-REFERENCE TO RELATED APPLICATION

The present application is a Continuation-in-Part of U.S. patent application Ser. No. 15/346,199, filed Nov. 8, 2016, which is a Continuation-in-Part of U.S. patent application Ser. No. 15/228,019, filed Aug. 4, 2016, which is a Continuation-in-Part of U.S. patent application Ser. No. 15/083,467, filed Mar. 29, 2016, which are all incorporated herein by reference in their entireties for all purposes.

BACKGROUND

Field of the Invention

The present invention relates to rod connectors, such as spinal hardware connectors.

Description of the Related Art

At times, spinal surgeons may be required to add additional fixation to spinal segments adjacent to previously instrumented levels. In these cases, the hardware from the initial surgery may interfere with placement of new fixation for the adjacent level. Therefore, there is a need for connector implants that attach to the existing spinal fusion construct on one end and extend fixation to adjacent levels in need of fusion. Quicker recovery times and lessened discomfort makes minimally invasive surgical (MIS) techniques favorable in these situations.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present disclosure relates to components, systems, and methods for connecting one device to another device. For example, one elongate implant, such as a first rod, may be coupled to another elongate implant, such as a second rod. The elongate implants, such as rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a scoliosis operation, or at a later surgery, for example, in a revision surgery. In a revision surgery, connectors can be used to connect new fixation constructs to existing fixation constructs without the need to remove the original hardware. The different connection modes provided in the following exemplary embodiments offer a range of options to be chosen based on a specific clinical scenario and/or surgeon preference. Although certain configurations are shown herein, it is envisioned that any suitable number, type, and selection of connectors and implants may be chosen and configured by the skilled surgeon.

According to one embodiment, a modular connector system includes a connector having a body having a first clamping portion and a second modular portion. The first clamping portion has a first passage having a first longitudinal axis extending therethrough and being sized to allow a first rod to be inserted therein, a bottom portion having an opening in communication with the first passage, and a first securing mechanism comprising a set screw, a clamp having two opposing legs, and an opening defined between the two opposing legs, the clamp being connected to the set screw and the set screw being rotatably connected to the body, the first securing mechanism having an unlocked position configured to receive the first rod and a locked position configured to releasably secure the first rod in the opening between the two opposing legs of the clamp and in the first passage. The second modular portion has a post extending from the body and having a partially spherical outer surface. The post is configured to receive a plurality of different modular connectors. Each modular connector is configured to articulate relative to the body of the connector. The modular connector may include a tulip-style assembly, a headed rod, or other suitable modular component.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 44 is a perspective view of a revision connector according to a nineteenth exemplary embodiment;

FIG. 45 is a sectional view of the revision connector shown in FIG. 44, mounted on an existing construct;

FIG. 46 is a side elevational view of the revision connector shown in FIG. 45, connecting a new construct to the existing construct;

FIG. 55 is a perspective view of the top loading connector shown in FIG. 31, mounted on an existing construct;

FIG. 56 is a perspective view of the top loading connector shown in FIG. 31, connecting a new construct to the existing construct;

FIG. 62 is a side perspective view of a double head lateral connector according to a twenty-third exemplary embodiment;

FIG. 63 is a side elevational view of the double head lateral connector shown in FIG. 62;

FIG. 64 is a top perspective view of the double head lateral connector shown in FIG. 62;

FIGS. 101A-101F depict yet another embodiment of a top loading connector.

DETAILED DESCRIPTION

Figure 1:
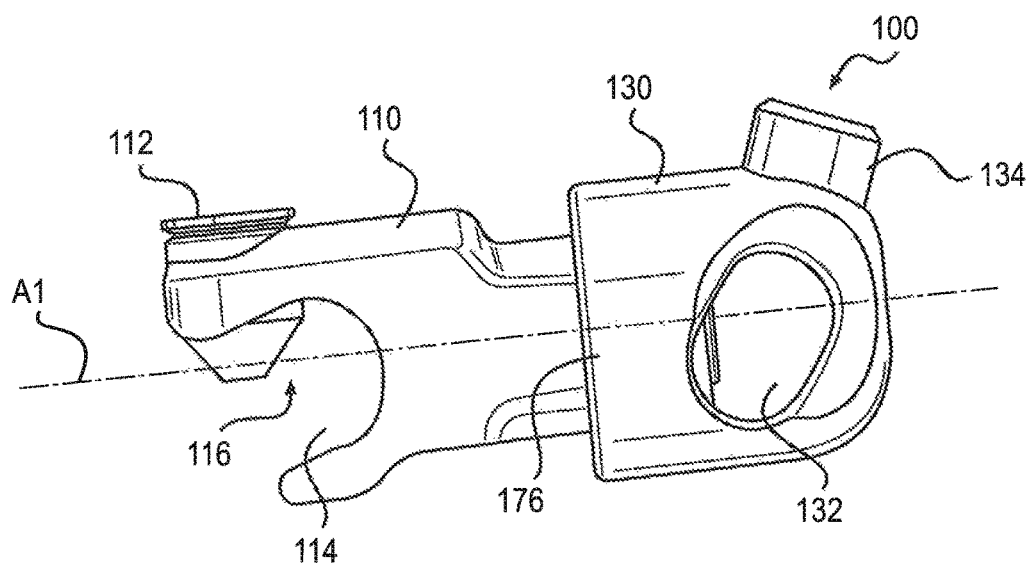
FIG. 1 is a side elevational view of an articulating revision connector according to a first exemplary embodiment.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The present disclosure relates to components, systems, and methods for connecting one elongate implant, such as a first rod, to another elongate implant, such as a second rod. The elongate implants, such as rods, are well known to connect adjacent vertebrae in a spinal fusion procedure. Depending on the configuration of rods or implants, it may be desirable to have one rod connected to another rod or additional implant. In the case of two or more rods, these rods may be interconnected with one or more connectors, for example, in a single given surgery, such as a scoliosis operation, or at a later surgery, for example, in a revision surgery.

For example, connectors can be used to connect new fixation constructs to existing fixation constructs without the need to remove index surgery hardware. A benefit to such direct attachment to existing constructs saves operating time, causes less disruption to the patient, and minimizes patient healing time. The ability of the inventive connectors to maintain connection with existing constructs can maximize utility in cases of varying patient anatomy and existing spinal constructs. The different connection modes provided in the following exemplary embodiments offer a range of options to be chosen based on a specific clinical scenario and/or surgeon preference. Thus, although certain configurations are shown herein, it is envisioned that any suitable number, type, and selection of connectors and implants, such as rods, may be chosen and configured by the skilled surgeon.

While the different connection modes disclosed herein can be used independently, those skilled in the art will recognize that the connection modes can be combined "à la carte" according to patient needs. Further, while the connection modes disclosed herein can be provided separately, kits that include various and multiple combinations of different connection modes can also be provided.

Figure 2:
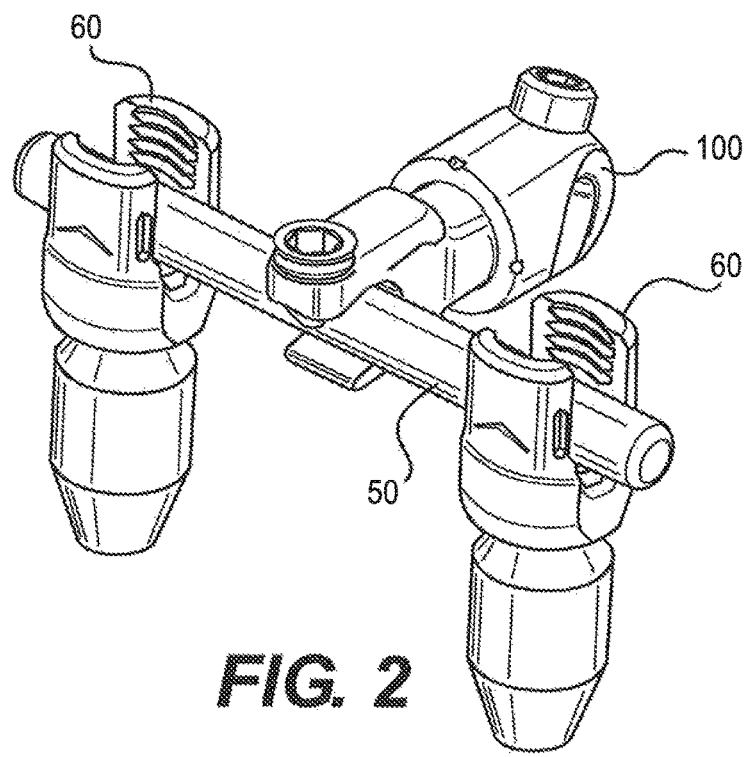
FIG. 2 is a perspective view of the articulating revision connector shown in FIG. 1 connected to an existing rod construct.

Referring to FIGS. 1-5, an articulating revision connector assembly 100 ("connector assembly 100") according to a first exemplary embodiment is shown. Connector assembly 100 is used to attach to a first rod 50, for example, that is already present in an existing construct. As shown in FIG. 2, first rod 50 can be supported by and secured to one or more screw heads 60 (e.g., a tulip assembly connected to a polyaxial pedicle screw). Although not shown, a cap or securing member, such as a threaded cap, may then be engaged with the threaded portion of the tulip to secure the rod 50 therein. While FIG. 2 shows connector assembly 100 as being located between screw heads 60, those skilled in the art will recognize that connector assembly 100 can be located in other places along first rod 50. For example, the connector assembly 100 can positioned such that it is substantially in contact with a portion of the screw heads 60 (e.g. substantially in contact with an outer portion of the tulip assembly).

Referring back FIG. 1, connector assembly 100 is an open lateral connector that extends an existing construct an adjacent level. Connector assembly 100 includes an open clamp portion 110 rotatably connected to a closed clamp portion 130 that provides articulation about open clamp portion 110 to a desired angle. Once the desired rotational position is achieved, closed clamp portion 130 can be secured to open clamp portion 110, locking the articulation.

Open clamp portion 110 includes a securing mechanism 112, such as a set screw, that is rotatably connected thereto. Open clamp portion 110 includes a blind passage 114 with a clamp opening 116 that extends along a first axis "A1". Securing mechanism 112 is mounted in a through passage 118 (shown in FIG. 5) extending generally orthogonally relative to first axis A1.

Figure 3:
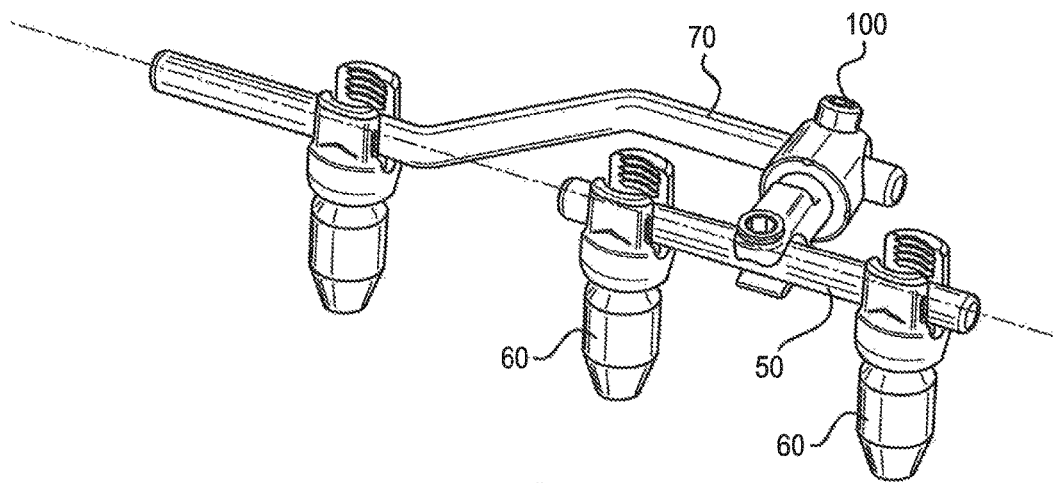
FIG. 3 is a perspective view of the articulating revision connector and rod construct shown in FIG. 2, with the connector also being connected to a newly installed rod.
Figure 4A:
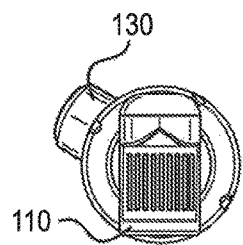
FIG. 4A-E are end elevational views of the connector shown in FIG. 1, with the articulating portion rotated about multiple angles with respect to the fixed portion of the connector.
Figure 4B:
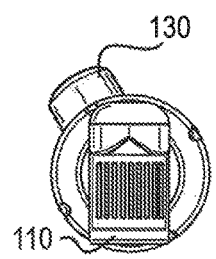
Figure 4C:
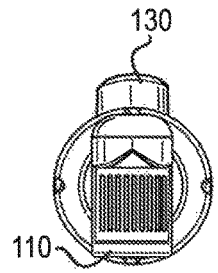
Figure 4D:
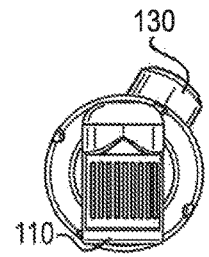
Figure 4E:
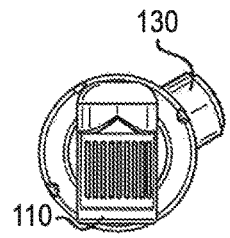

Closed clamp portion 130 is rotatably connected to open clamp portion 110. Closed clamp portion 130 has a passage 132 extending therethrough that is sized to allow passage of a second rod 70 (shown in FIG. 3) therethrough. The passage 132 is preferably sized and shaped to receive the rod 70. In the embodiment shown, the passage 132 is elongated to have a length greater than its width to allow for some translation of the rod 70 in the passage 132 before the securing member 134 is tightened. It is envisioned, however, that the passage 132 may be substantially circular or cylindrical in shape. Rod 70 may be a Z-rod (shown in FIG. 71) in order to extend rod 50 co-linearly, as shown in FIG. 3. Although not shown, any other suitable rod may be selected, for example, to allow for a parallel configuration or to select a rod that may be bent in situ.

Closed clamp portion 130 includes a securing member 134 that is adapted to bias second rod 70. Securing member 134 is rotatably mounted in a through-passage 135 that extends generally obliquely relative to longitudinal axis A1. The rotation of closed clamp portion 130 relative to open clamp portion 110 is illustrated in FIGS. 4A-4E, which show closed clamp portion 130 rotated across five different positions relative to open clamp portion 110. Those skilled in the art will recognize that closed clamp 130 has 360° of rotation relative to open clamp portion 110. It is envisioned, however, that the clamp 130 may be permitted to rotate any suitable amount relative to open clamp portion 110.

Figure 5:
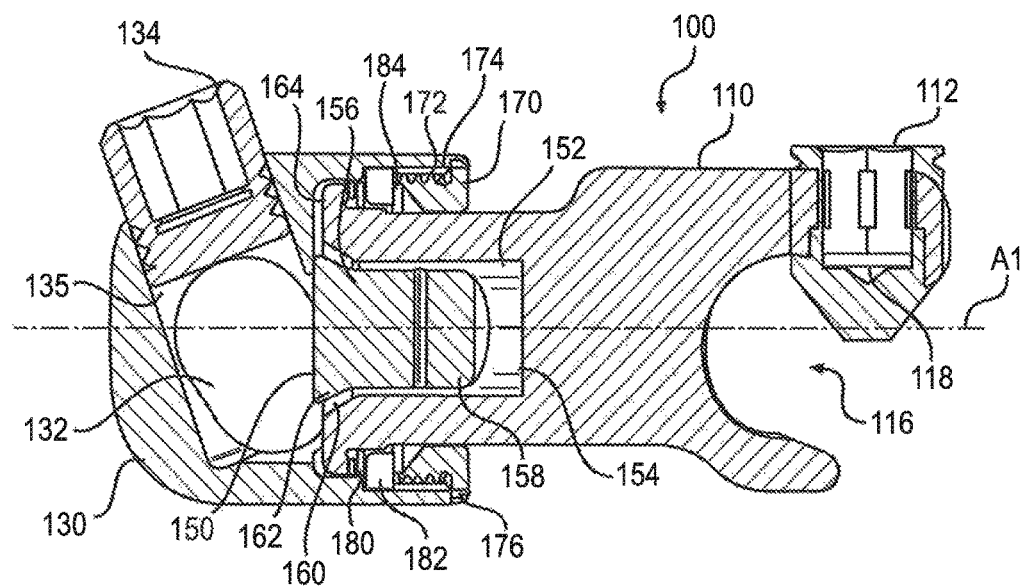
FIG. 5 is a sectional view of the articulating revision connector shown in FIG. 1.

Referring to FIG. 5, a locking mechanism 150 is configured to releasably prevent rotation of closed clamp portion 130 relative to open clamp portion 110 when rod 70 (not shown in FIG. 5) is inserted into passage 132. Locking mechanism 150 includes a blind passage 152 formed in closed clamp portion 130 and extending along longitudinal axis A1. Passage 152 has a first set of teeth 154. An insert 156 is longitudinally disposed in passage 152. Insert 156 has a second set of teeth 158 that are releasably engageable with the first set of teeth 154, such that, when insert 156 is longitudinally translated toward open clamp portion 110, second set of teeth 158 engages first set of teeth 154, restricting rotation of open clamp portion 110 relative to closed clamp portion 130.

Passage 152 has an outwardly flared opening 160, and insert 156 has a corresponding outwardly flared end 162 that is adapted to engage outwardly flared opening 160 when insert 156 is longitudinally translated toward open clamp portion 110. Flared opening 160 of passage 152 also includes a lip 164 that extends radially away from first axis A1.

A cap 170 is threadably connected to closed clamp portion 130 to rotatably retain closed clamp portion 130 on open clamp portion 110. Cap 170 includes a threaded connection 172 that threadably engaged with mating threads 174 on closed clamp portion 130. An exterior of cap 170 also includes radially spaced recesses 176 allow for the application of a tool (not shown), such as, for example, a spanner wrench, to attach/remove cap 170 to/from closed clamp portion 130.

A plurality of bushings and washers 180-184 are located on the exterior of open clamp portion 110 between cap 170 and lip 164 and serve to form a frictional connection between cap 170 and lip 164 when closed clamp portion 130 is locked to open clamp portion 110.

To assemble connector assembly 100 and add rod 70 to an existing construct, clamp opening 116 of connector assembly 100 is secured to rod 50, and rod 70 is then inserted into passage 132 as shown in the exemplary configuration shown in FIG. 3. When rod 70 is located at a desired angle with respect to rod 50, securing mechanism 112 is advanced through passage 118, such that securing mechanism 112 biases rod 70 against insert 156, advancing insert 156 along longitudinal axis A1 toward passage 114. Teeth 158 on insert 156 engage with teeth 154 in passage 152 and seat flared end 162 of insert 156 on flared opening 160 of passage 152, forcing lip 164 to bias toward cap 170, thereby restricting rotation of open clamp portion 110 relative to closed clamp portion 130.

Figure 6:
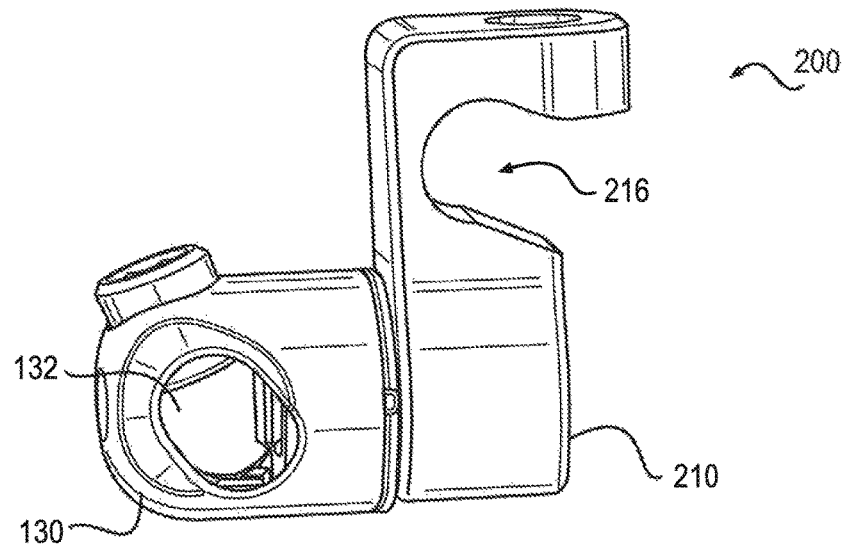
FIG. 6 is a side elevational view of an articulating revision connector according to a second exemplary embodiment.

In an alternative embodiment, shown in FIG. 6, a clamp assembly 200 incorporates closed clamp portion 130, but, instead of open clamp portion 110, includes an open clamp portion 210 rotatably attached thereto. Open clamp portion 210 comprises a clamp opening 216 extending obliquely relative to the first axis A1, with opening 216 in an offset plane relative to opening 132 in closed clamp portion 130.

Figure 7:
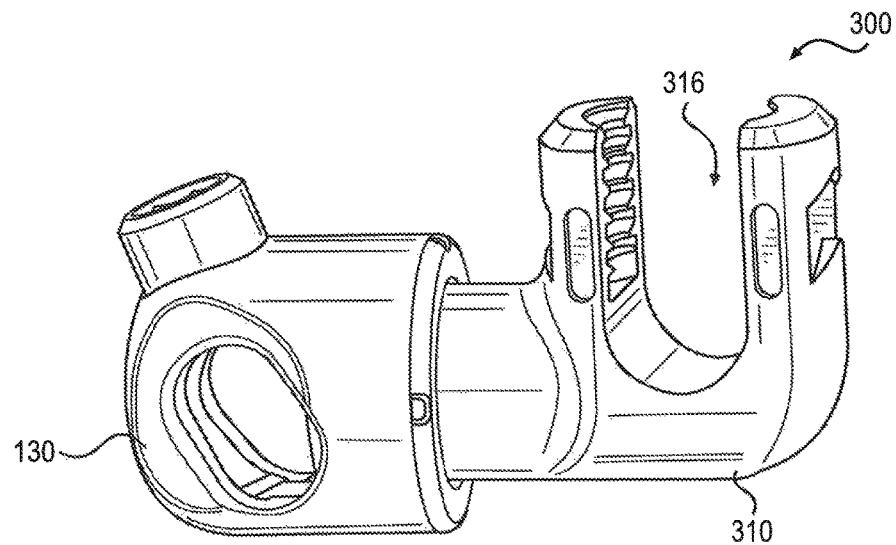
FIG. 7 is a perspective view of an articulating revision connector according to a third exemplary embodiment.
Figure 8:
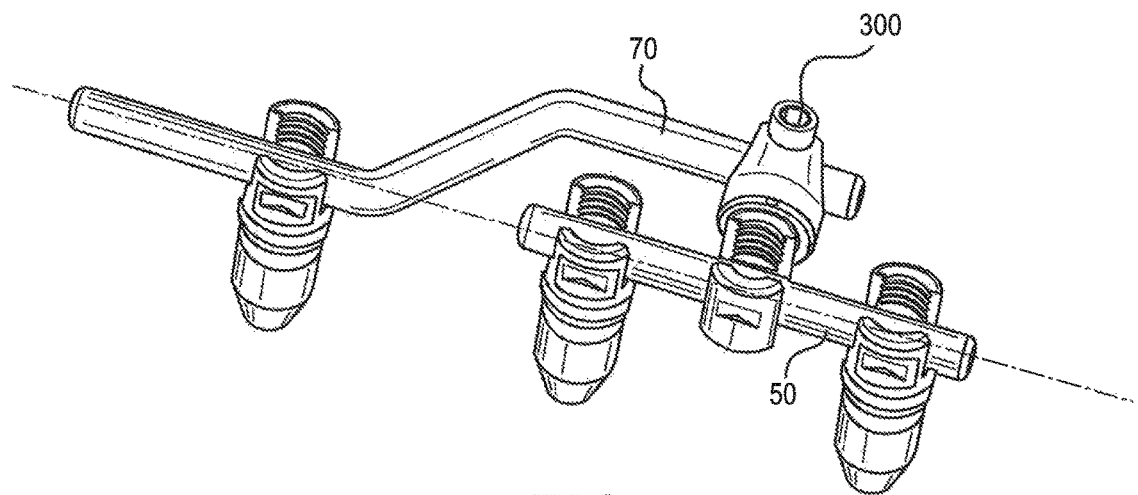
FIG. 8 is a perspective view of the connector shown in FIG. 7 connected to an existing rod construct and a newly installed rod.

In another alternative embodiment of a connector assembly 300, shown in FIG. 7, wherein an open clamp portion 310 comprises a clamp opening 316 extending generally orthogonally relative to first axis A1 such that a blind end of opening 316 extends along first axis A1, allowing the insertion of rod 50 in opening 316 to be coplanar with rod 70 after rod 70 is inserted into passage 132. FIG. 8 shows the connection of connector assembly 300 with rod 70 extending in the same lateral plane as existing rod 50. This configuration allows the open clamp portion 310 to be positioned beneath the existing rod 50. A threaded cap (not shown) may then be engaged with the threaded portion on the top of the open clamp portion 310 to secure the rod 50 therein, thereby coupling rod 50 to rod 70.

Figure 9:
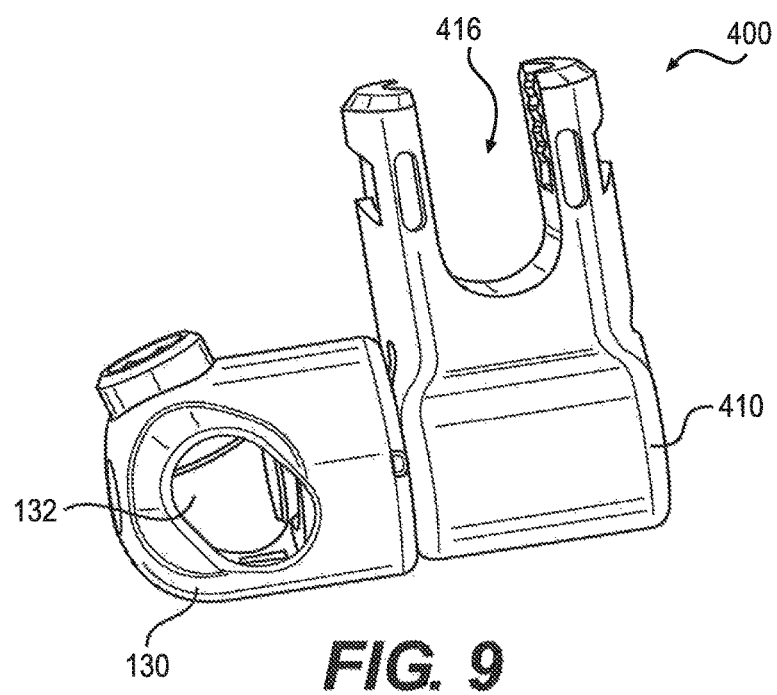
FIG. 9 is a perspective view of an articulating revision connector according to a fourth exemplary embodiment.
Figure 10:
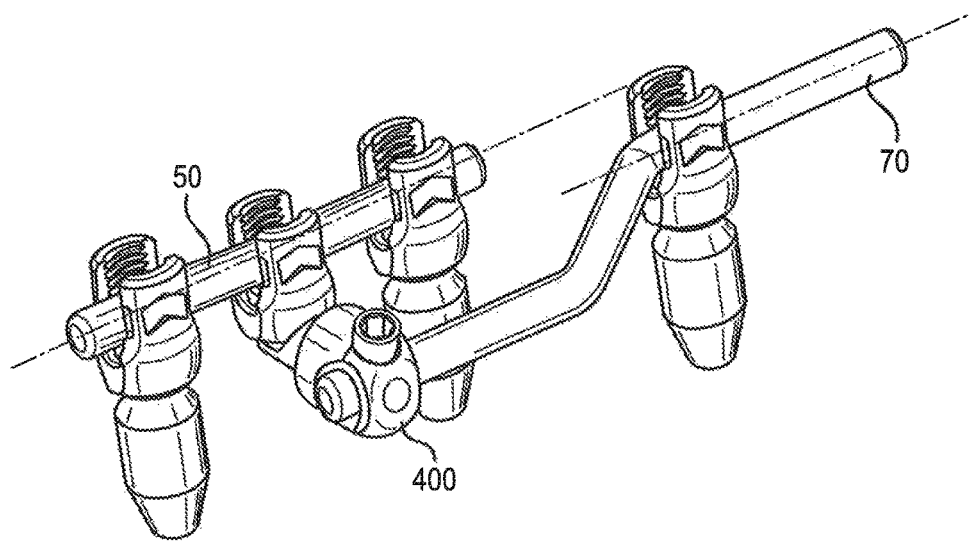
FIG. 10 is a perspective view of the connector shown in FIG. 9, connected to an existing rod construct and a newly installed rod.

In still another embodiment of a connector assembly 400, shown in FIGS. 9 and 10, an open clamp portion 410 comprises a clamp opening 416 extending generally orthogonally relative to first axis A1 such that a blind end of opening 416 extends above first axis A1, allowing the insertion of rod 50 in opening 416 to be skewed with respect to rod 70 after rod 70 is inserted into passage 132. The open clamp portion 410 may have a generally U-shaped configuration allowing for the open clamp portion 410 to be positioned beneath the existing rod 50. A threaded cap (not shown) may then be engaged with the threaded portion on the top of the open clamp portion 410 to secure the rod 50 therein, thereby coupling existing rod 50 to new rod 70.

Figure 11:
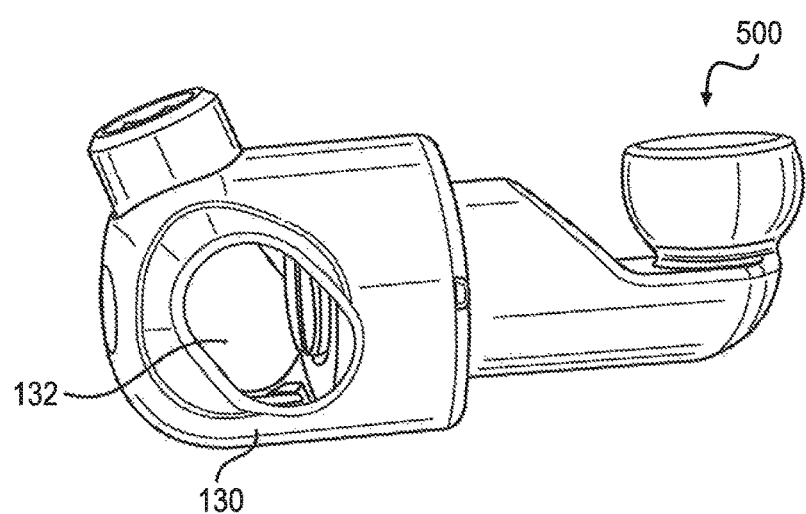
FIG. 11 is a perspective view of an articulating revision connector according to a fifth exemplary embodiment.
Figure 28:
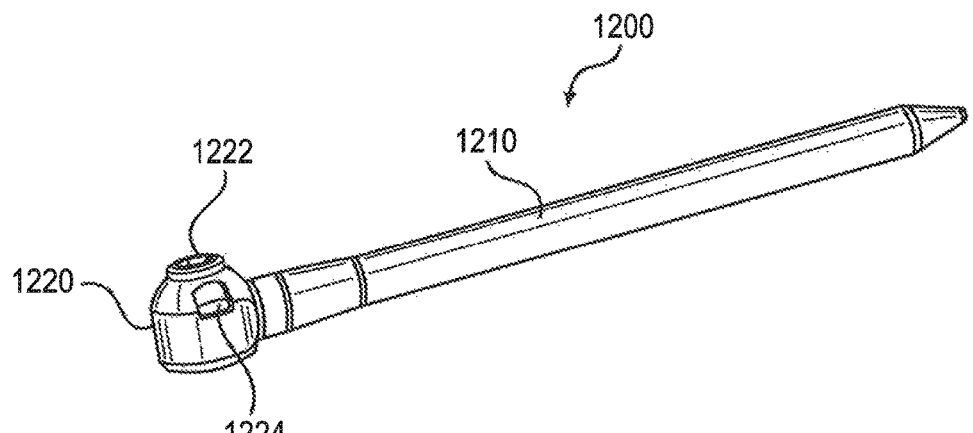
FIG. 28 is a perspective view of a link connector according to a twelfth exemplary embodiment.

In yet another embodiment of a connector assembly 500, shown in FIG. 11, and articulating modular lateral head connector is provided. In this embodiment, the open clamp portion is replaced with a connection point, such as a post, configured to receive a rod having a modular connection point 1220, for example, as depicted in FIG. 28 and described in more detail below. The post or connection point may have a partially spherical outer surface with a generally flat top surface to enable engagement with a corresponding opening in the rod.

Figure 12:
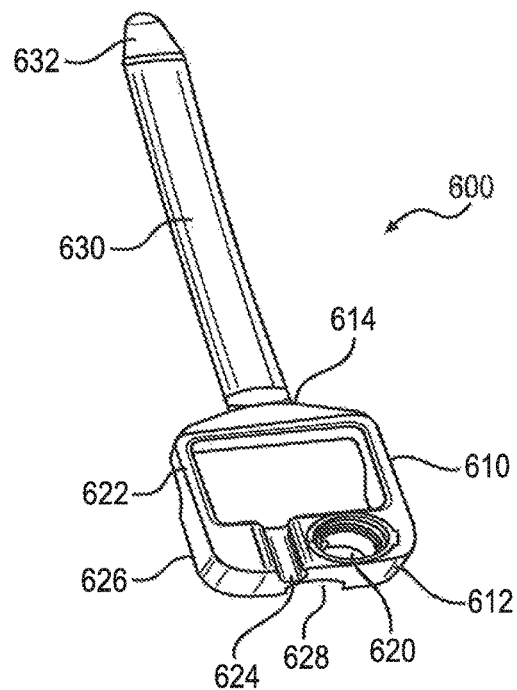
FIG. 12 is a perspective view of an integrated revision connector according to a sixth exemplary embodiment.
Figure 13:
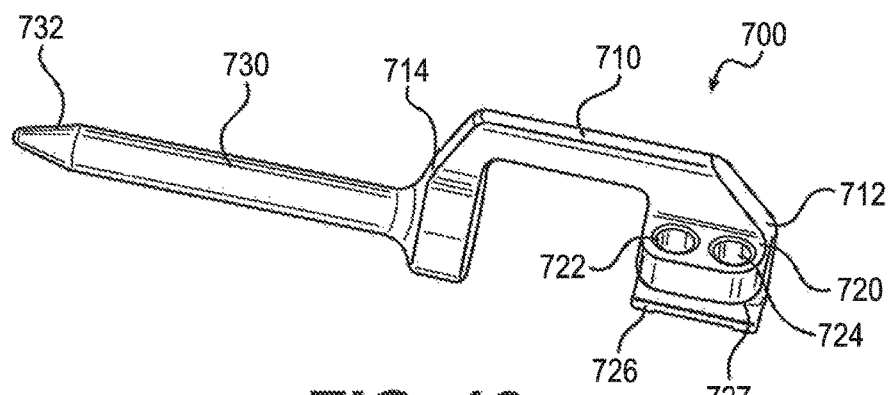
FIG. 13 is a perspective view of an integrated revision connector according to a seventh exemplary embodiment.

Referring now to FIGS. 12-27, a plurality of integrated revision connectors according to exemplary embodiments are shown. In an exemplary embodiment, shown in FIG. 12, a spinal revision connector assembly 600 includes a body 610 having a first end 612 and a second end 614. Body 610 is generally a closed loop that provides a space sufficiently large for the insertion of a pre-existing construct, such as, for example, a spinal implant screw head (not shown) therethrough, thereby minimizing the amount of new construct that is to be connected to an existing construct.

A first connecting member 620 is located at first end 612. In an exemplary embodiment, first connecting member 620 can be a threaded opening that allows for the insertion of a fastener, such as a set screw (not shown), that provides for connection to existing construct.

An upper surface 622 of first end 612 includes an arcuate recess 624 sized to accept a rod (not shown) from an existing construct. Similarly, a lower surface 626 includes an arcuate recess 628 sized to accept a rod (not shown) from an existing construct. Recesses 624, 626 can be the same or different sizes (as shown) in order to be able to accommodate rods of different diameters.

A rod 630 extends from second end 614 of body 610. Rod 630 can have a tapered tip 632 at a distal end of rod 630 from body 610. Rod 630 can extend an existing construct two adjacent level in order to provide required fixation.

Figure 14:
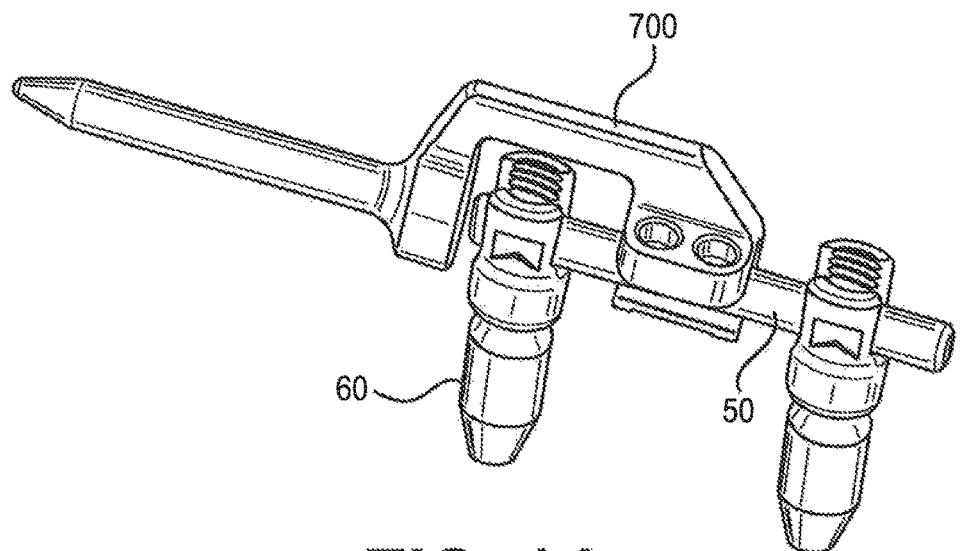
FIG. 14 is a perspective view of the integrated revision connector shown in FIG. 13, connected to an existing construct.
Figure 15:
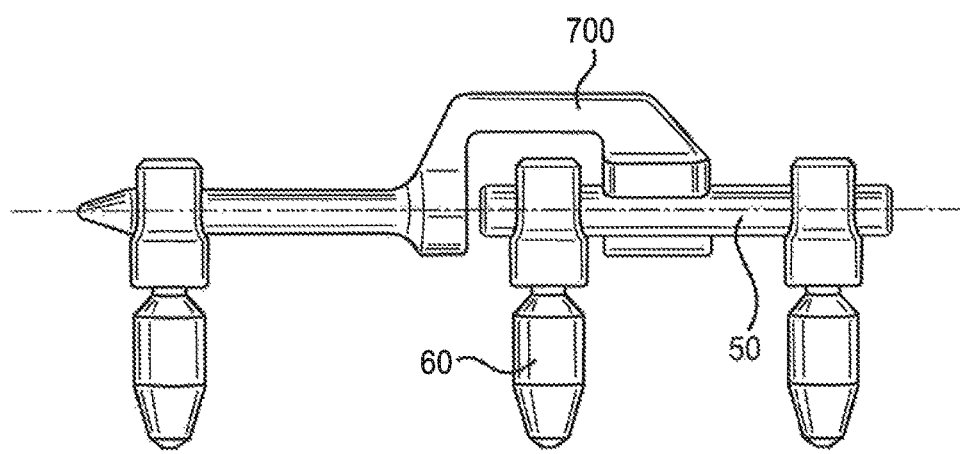
FIG. 15 is a side elevational view of the integrated revision connector connected to an existing construct shown in FIG. 14
Figure 16:
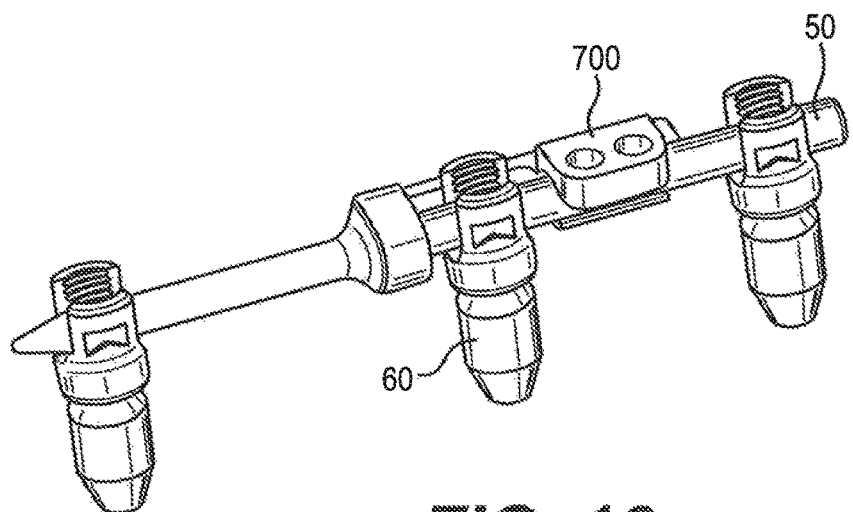
FIG. 16 is a perspective view of the integrated revision connector shown in FIG. 13, alternatively connected to an existing construct.

In an alternative exemplary embodiment, shown in FIGS. 13-16, a spinal revision connector assembly 700 includes a body 710 having a first end 712 and a second end 714. Body 710 is generally an open loop that provides a space sufficiently large for the insertion of body 710 over the top of a screw head 60 in an existing construct where rod 50 is of insufficient length protruding from the side of screw head 60, as shown in FIGS. 14 and 15. Alternatively, body 710 can go around screw head 60 in the existing construct, as shown in FIG. 16.

A first connecting member 720 is located at first end 712. In an exemplary embodiment, first connecting member 720 can be one or more threaded openings 722, 724, that allow for the insertion of a fastener, such as a set screw (not shown), that provides for connection to existing construct. Additionally, a lower lip 726 is used to support an underside of rod 50 to provide secure clamping of first connecting member 720 to rod 50, such that a passage 727 is formed between lower lip 726 and first end 712.

A rod 730 extends from second end 714 of body 710. Rod 730 can have a tapered tip 732 at a distal end of rod 730 from body 710. Rod 730 extends along a common axis with passage 727 such that rod 730 extends the existing construct of rod 50 at an adjacent level.

Figure 17:
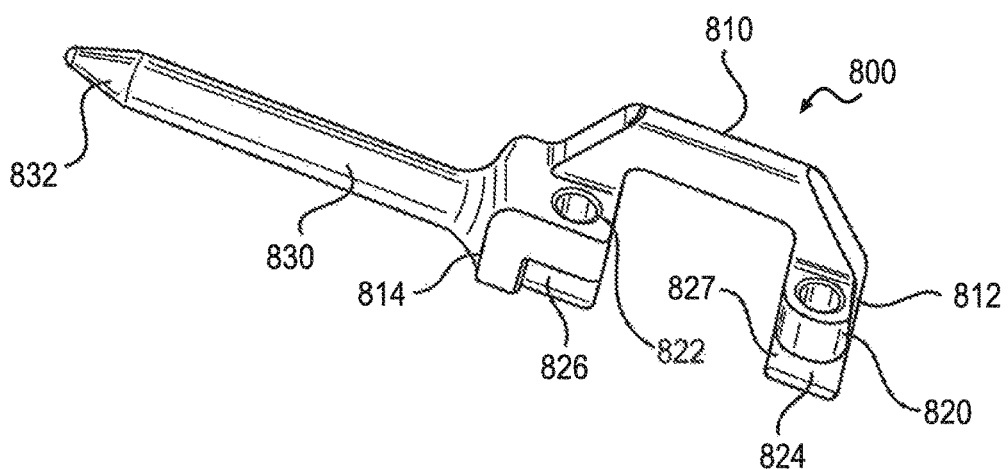
FIG. 17 is a perspective view of an integrated revision connector according to an eighth exemplary embodiment.
Figure 18:
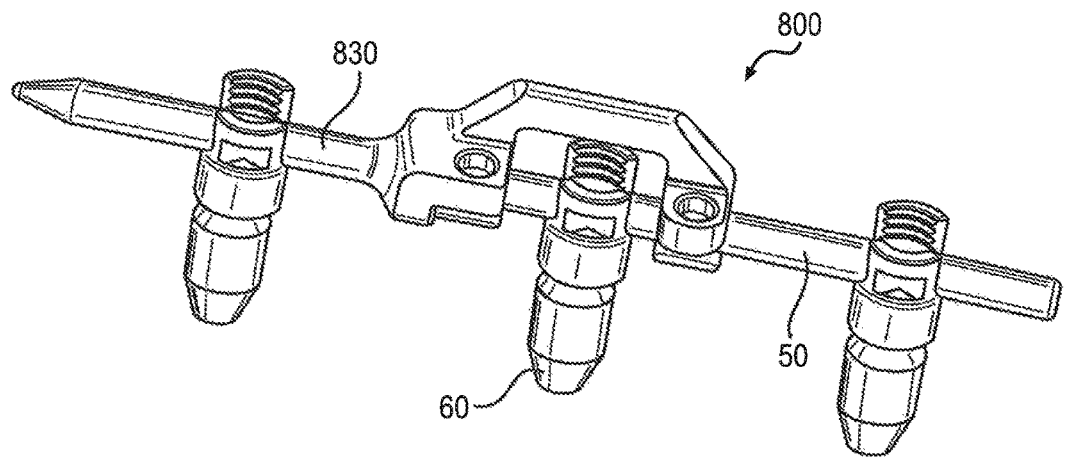
FIG. 18 is a perspective view of the integrated revision connector shown in FIG. 17, connected to an existing construct.

In another alternative exemplary embodiment, shown in FIGS. 17 and 18, a spinal revision connector assembly 800 includes a body 800 and having a first end 812 and a second end 814. Body 810 is generally an open loop with a space between first end 812 and second end 814 that allows for the insertion of body 810 over the top of screw head 60 in an existing construct where rod 50 is of insufficient length protruding from the side of screw head 60, as shown in FIG. 18. It is noted that, in FIG. 18, the length of rod 50 extending beyond screw head 60 is longer than that shown in FIG. 14, allowing for the use of assembly 800, as shown in FIG. 18.

A first connecting member 820 is located at first end 812 and a second connecting member 822 is located at second end 814. First connecting member 820 and second connecting member 822 can be threaded openings that allow for the insertion of a fastener, such as a set screw (not shown), to secure assembly 800 to rod 50 where rod 50 is sufficiently long to allow rod 50 to extend beyond screw head 60, such that rod 50 can be engaged and secured by second connecting member 822, as shown in FIG. 18. Additionally, a first lower lip 824 at first connecting member 820 and a second lower lip 826 at second connecting member 822 are used to support an underside of rod 50 to provide secure clamping of connecting members 820, 822 to rod 50, such that a passage 827 is formed between first lower lip 824 and first end 812 and between second lower lip 826 and second end 814.

A rod 830 extends from second end 814 of body 810. Rod 830 can have a tapered tip 832 at a distal end of rod 830 from body 810. Rod 830 extends along a common axis with passage 827 such that rod 730 extends the existing construct of rod 50 at an adjacent level.

Figure 19:
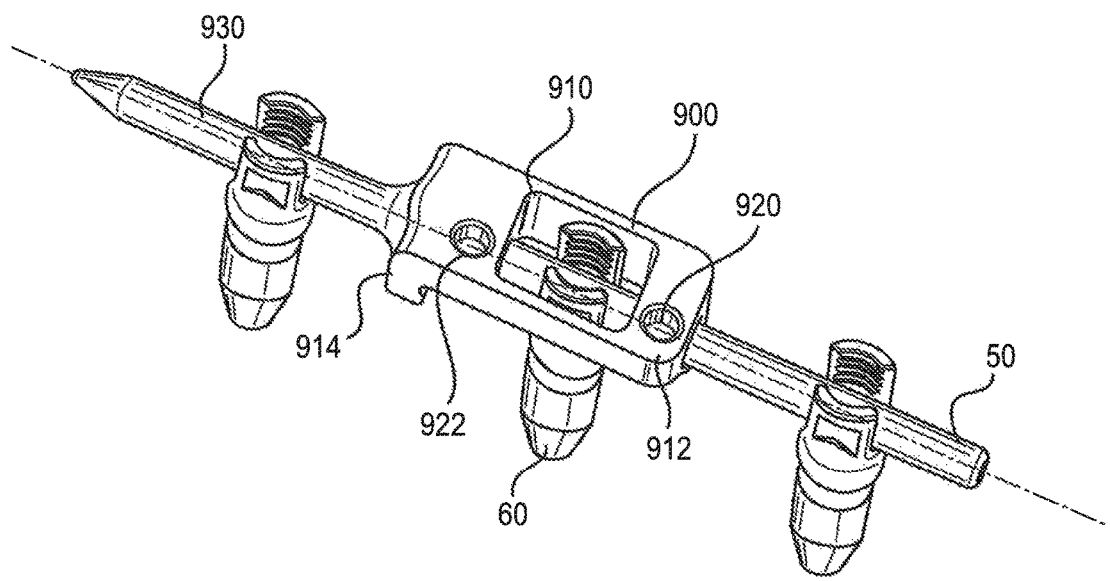
FIG. 19 is a perspective view of an integrated revision connector according to a ninth exemplary embodiment, connected to an existing construct.

In still another alternative exemplary embodiment, shown in FIG. 19, a spinal revision connector assembly 900 includes a body 910 having a first end 912 and a second end 914. Body 910 is generally a closed loop that provides a space between first end 912 and second end 914 sufficiently large for the insertion of a pre-existing construct, such as, for example, screw head 60, therethrough, thereby minimizing the amount of new construct that is to be connected to an existing construct.

A first connecting member 920 is located at first end 912 and a second connecting member 922 is located at second end 914. First connecting member 920 and second connecting member 922 can be threaded openings that allow for the insertion of a fastener, such as a set screw (not shown), to secure assembly 900 to rod 50 where rod 50 is sufficiently long to allow rod 50 to extend beyond screw head 60, such that rod 50 can be engaged and secured by second connecting member 922.

A rod 930 extends from second end 914 of body 910. Rod 930 can have a tapered tip 932 at a distal end of rod 930 from body 910.

Figure 20:
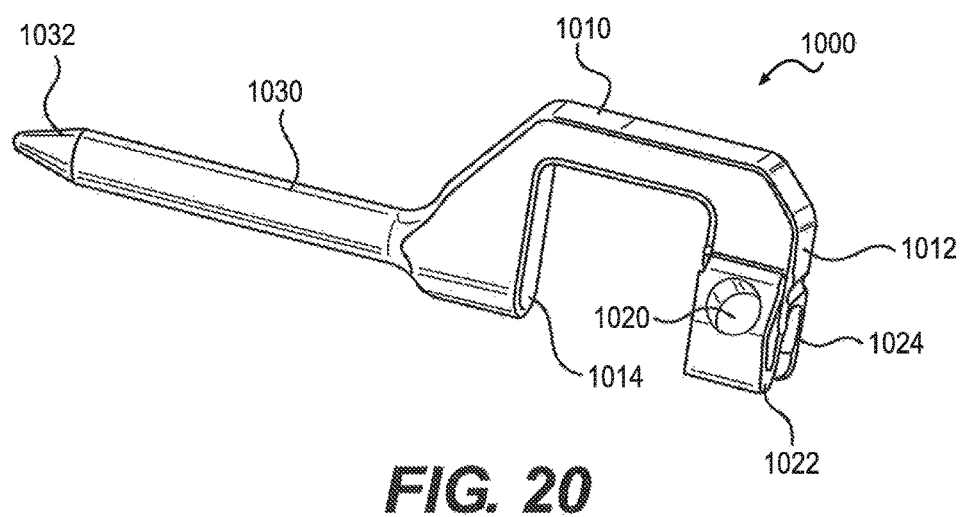
FIG. 20 is a perspective view of an integrated revision connector according to a tenth exemplary embodiment.
Figure 21:
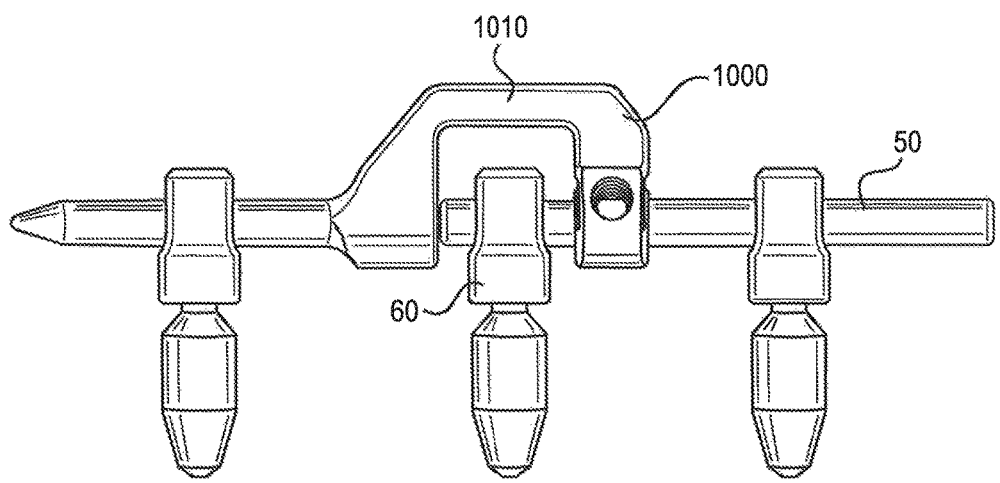
FIG. 21 is a perspective view of the integrated revision connector shown in FIG. 20, connected to an existing construct.
Figure 22:
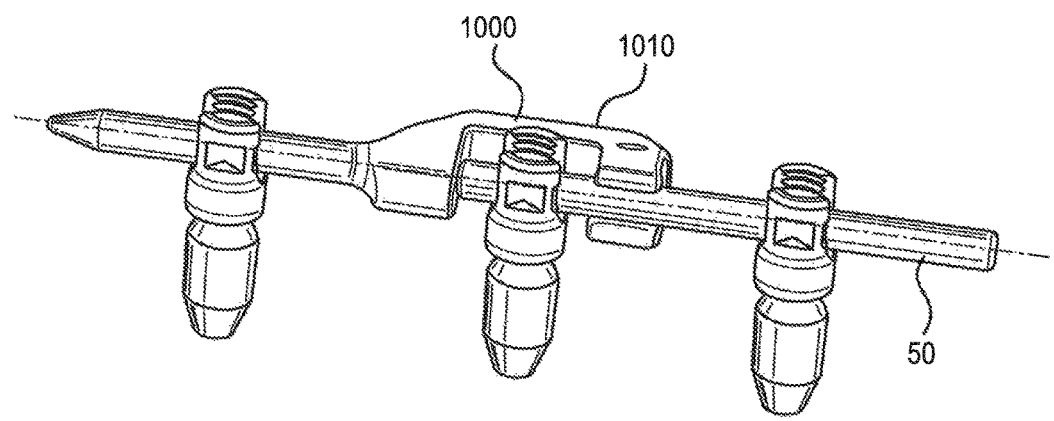
FIG. 22 is a perspective view of the integrated revision connector shown in FIG. 20, alternatively connected to an existing construct.
Figure 23:
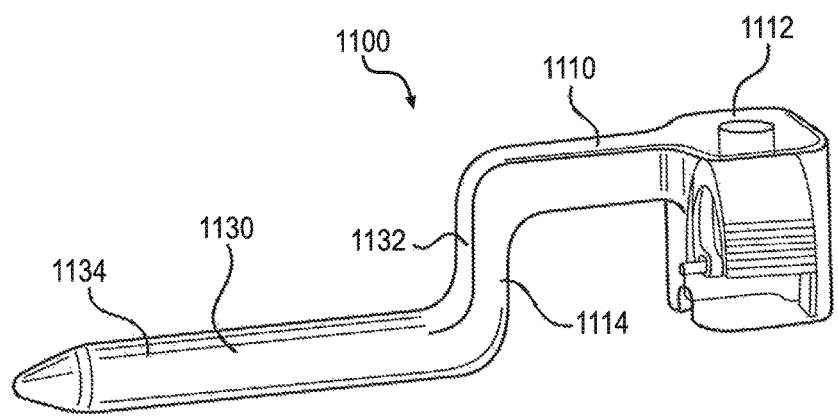
FIG. 23 is a perspective view of an integrated revision connector according to an eleventh exemplary embodiment.
Figure 24:
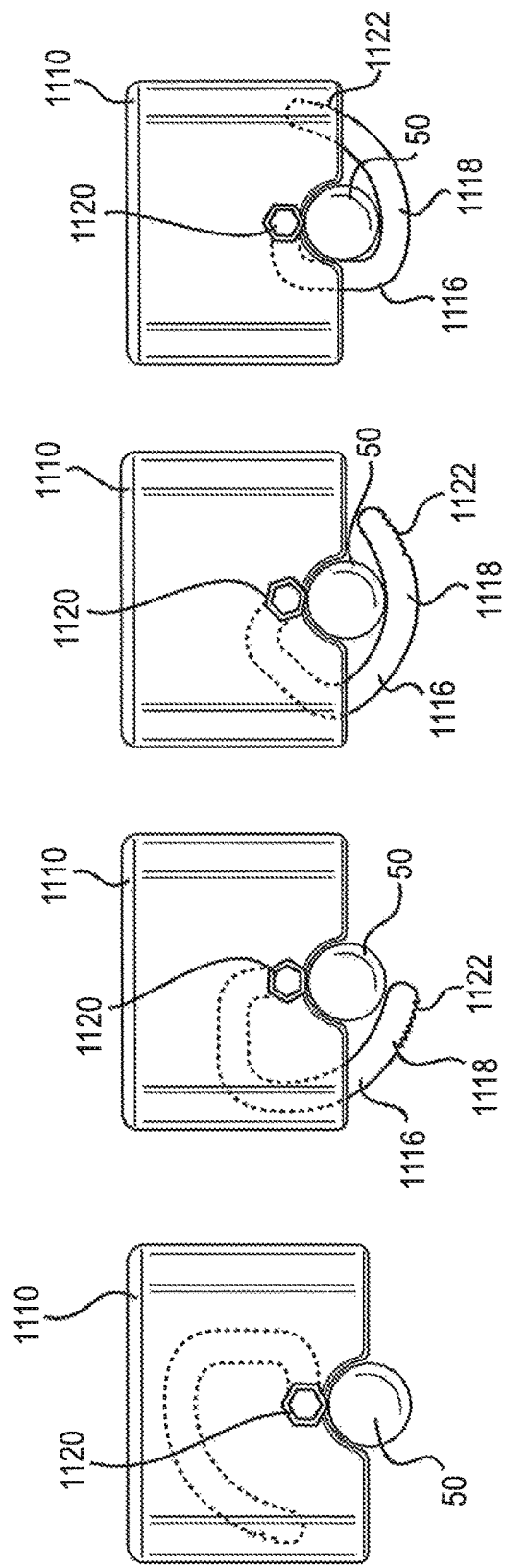
FIGS. 24A-D are side elevational views of advancing stages of a connecting mechanism of the integrated revision connector shown in FIG. 23.

In still another alternative exemplary embodiment, shown in FIGS. 20-22, a spinal revision connector assembly 1000 includes a body 1010 having a first end 1012 and a second end 1014. Body 1010 is generally an open loop that provides a space between first end 1012 and second end 1014 that is sufficiently large for the insertion of a pre-existing construct, such as, for example, screw head 60, therethrough, thereby minimizing the amount of new construct that is to be connected to an existing construct. FIG. 21 shows body 1010 extending over top of screw head 60, while FIG. 22 shows body 1010 extending around screw head 60.

A first connecting member 1020 is located at first end 1012. First connecting member 1020 can be a threaded opening that allows for the insertion of a fastener, such as a set screw (not shown), to secure assembly 1000 to rod 50. Connecting member 1020 also includes clamping surfaces 1022, 1024 that extend outwardly from first end 1012. Clamping surfaces 1022, 1024 are spaced sufficiently from each other to allow rod 50 to slide therethrough such that, when the fastener or set screw is secured, first connecting member 1020 securely grips rod 50.

A rod 1030 extends from second end 1014 of body 1010. Rod 1030 can have a tapered tip 1032 at a distal end of rod 1030 from body 1010. Rod 1030 extends at the adjacent level as for 50 (shown in FIG. 21).

In another alternative exemplary embodiment, shown in FIGS. 23-27, a spinal revision connector assembly 1100 includes a body 1110 having a first end 1112 and a second end 1114. First end 112 includes a clamp housing that contains an inner revolving mechanism 1116 that can be rotated to surround the underside of an existing rod 50.

Figure 25:
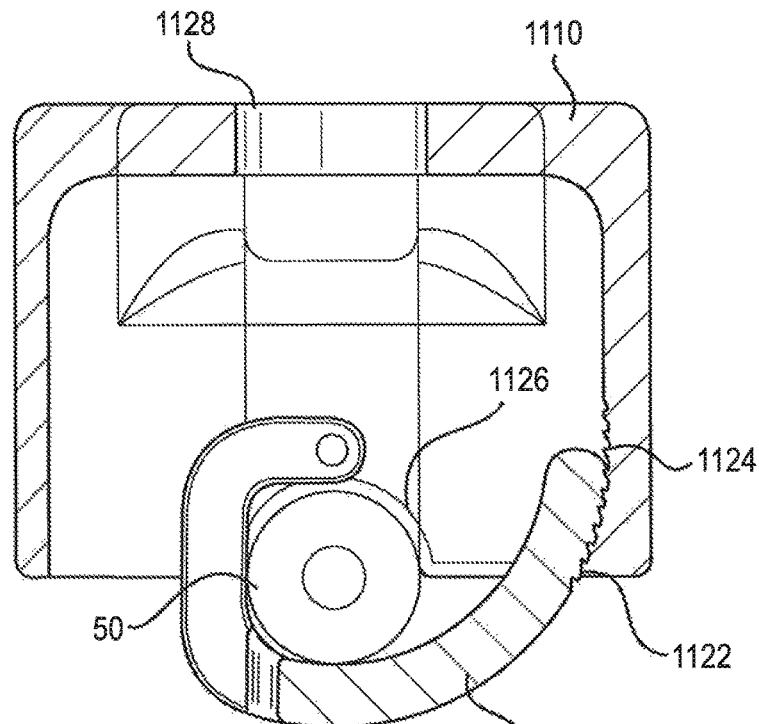
FIG. 25 is a sectional view of the connecting mechanism of the integrated revision connector shown in FIG. 23.

Mechanism 1116 includes a rotating clamp 1118 that is mounted on a pivot 1120. A distal end of clamp 1118 includes a plurality of ratchet teeth 1122. When clamp 1118 is rotated from the position shown in FIG. 24A to the position shown in FIG. 24D, ratchet teeth 1122 engage a securing mechanism in the form of internal ratchet teeth 1124 within body 1110 to secure clamp 1118 around rod 50, as shown in FIG. 25, preventing clamp 1118 from rotating backwards after final tightening. Clamp 1118 is rotated by rotating mechanism 1120. As shown in FIGS. 24A-24D, rotating mechanism 1120 can be a hex head screw that can be rotated by engaging a hex head tool, such as, for example, an Allen wrench (not shown), with rotating mechanism 1120 and rotating.

Figure 26:
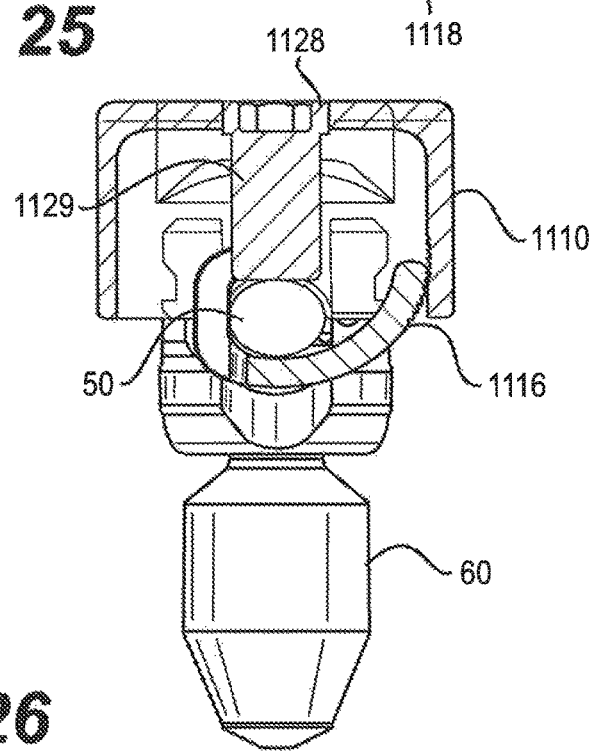
FIG. 26 is a sectional view of the connecting mechanism of the integrated revision connector shown in FIG. 23, connected to an existing construct.

Body 1110 includes arcuate cutouts 1126 on opposing sides thereof (only one cutout 1126 shown in FIG. 25), that are sized to receive rod 50 so that body 1110 snugly fits on rod 50. Body 1110 also includes a threaded top opening 1128 sized to receive a set screw 1129 inserted therein so that set screw 1129 can be screwed on top of rod 50, as shown in FIG. 26.

Figure 27:
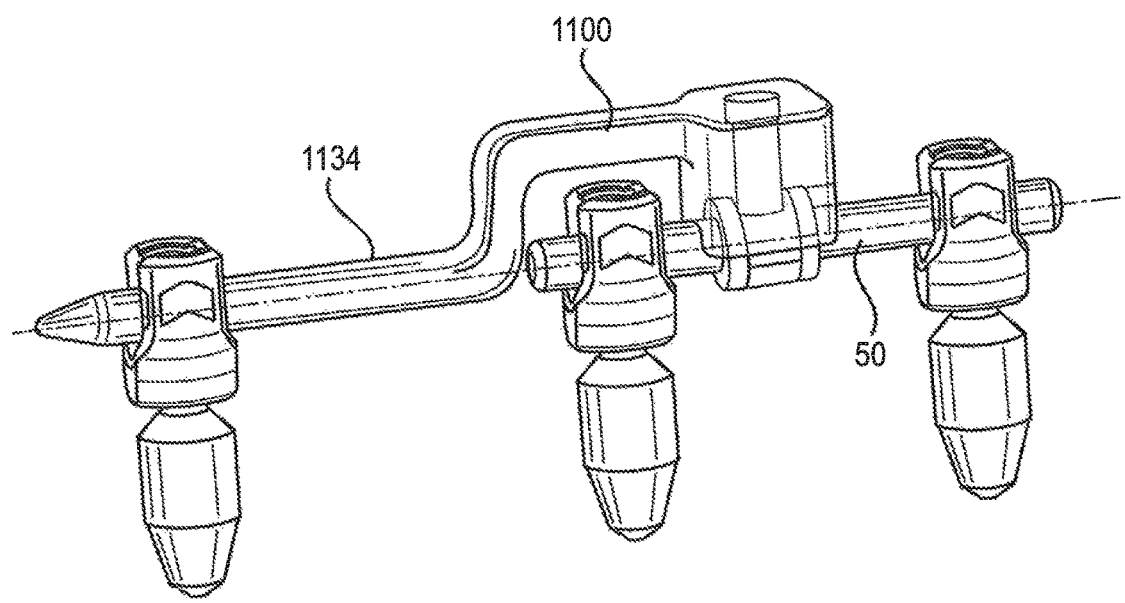
FIG. 27 is a perspective view of the integrated revision connector shown in FIG. 23, connected to the existing construct.

A rod 1130 extends from second end 1114 of body 1110. Second end 1114 comprises an offset portion 1132 and distal end 1134 extending away from offset portion 1132, such that distal end 1134 is at an adjacent level with rod 50, as shown in FIG. 27. A space is provided between first end 1112 and second end 1114 that is sufficiently large for the insertion of a pre-existing construct, such as, for example, a spinal implant screw head (not shown) therethrough, thereby minimizing the amount of new construct that is to be connected to an existing construct.

Referring now to FIGS. 28-38, a plurality of link connectors according to exemplary embodiments are shown. A first exemplary link connector 1200 is used with a mating modular connection point on a spinal screw, or a secondary connector implant.

Figure 29:
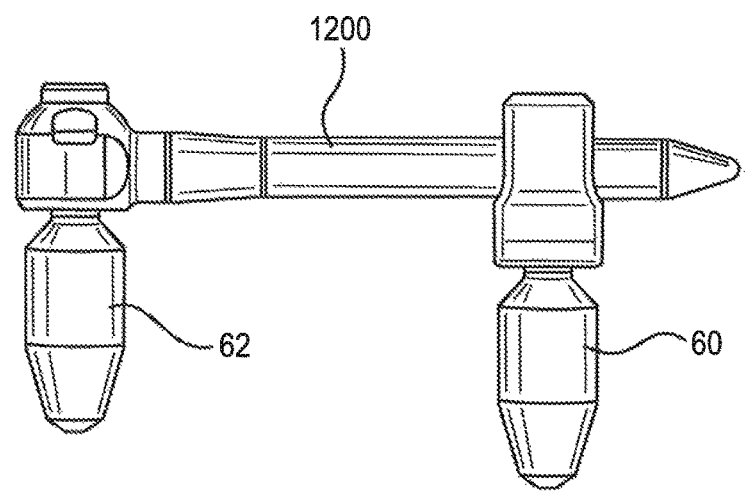
FIG. 29 is a side elevational view of the link connector shown in FIG. 28, connected to adjacent screws.

Referring specifically to FIGS. 28 and 29, a connector 1200 includes a rod 1210 within modular connection point 1220 at a first end. Connection point 1220 is a generally hollow body. Also, connection point 1220 includes a threaded connector, such as, for example, a fastener or set screw 1222 rotatably connected thereto and extending into the hollow body of connection point 1220. Additionally, connection point 1220 includes a diametrically opposed indents 1224 (only one indent 1224 shown in FIG. 28) to accommodate a gripping tool, such as, for example, a spanner wrench (not shown) that can be used to secure rod 1210 at a desired position while set screw 1220 is being tightened.

FIG. 29 shows connector 1200 spanning screw heads 60, 62. Connection point 1220 is secured directly to screw 62, while rod 1210 is secured to screw head 60, placed at an adjacent level.

Figures 30, 31:
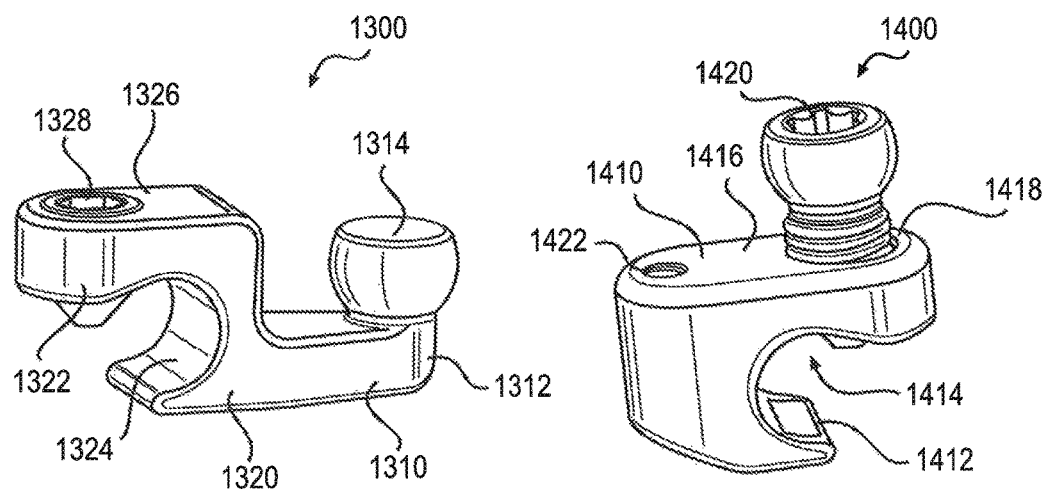
FIG. 30 is a perspective view of a lateral connector according to a thirteenth exemplary embodiment.
FIG. 31 is a perspective view of a top loading connector according to a fourteenth exemplary embodiment.

Referring to FIG. 30, an exemplary embodiment of a lateral connector 1300 is shown. Lateral connector 1300 includes a base 1310 having a first end 1312 with a connection point 1314 extending upwardly therefrom. Connection point 1314 is sized to fit into connection point 1220 and receives set screw 1222 from link connector 1200.

Figure 32:
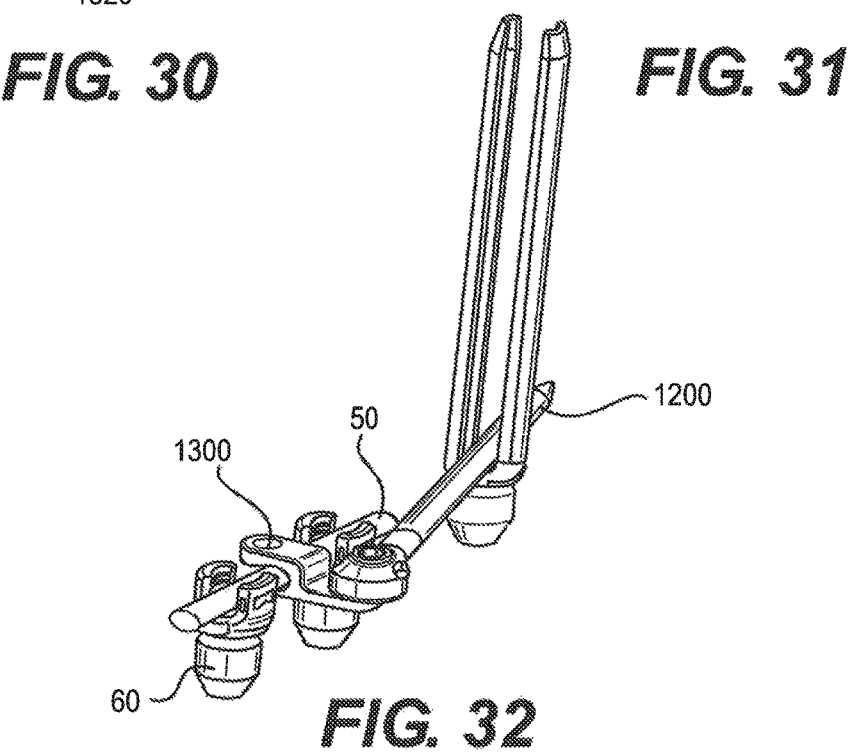
FIG. 32 is a perspective view of the link connector shown in FIG. 28 and the lateral connector shown in FIG. 30, connected to an existing construct and supporting a new construct.

Base 1310 also has a second end 1320 that includes a rod clamp 1322. Rod clamp 1322 includes an arcuate surface 1324 for engaging a rod and a top surface 1326, extending above connection point 1314, that supports a securing member, such as, for example, a set screw 1328 that can be rotated to secure rod 50 within rod clamp 1322, as shown in FIG. 32. As shown in FIG. 32, rod 1210 can extend at an oblique angle relative to rod 50, in order to accommodate for the lateral offset in lateral connector 1300.

Referring to FIG. 31, a top loading connector 1400 is shown. Connector 1400 includes a body 1410 that includes a rod clamp 1412. Rod clamp 1412 includes an arcuate surface 1414 for engaging a rod and a flat top surface 1416 disposed above arcuate surface 1414. Top surface 1416 includes a first threaded connection 1418 that receives a set screw 1420. Top surface 1416 also includes a second threaded connection 1422, for receiving an additional connector (not shown).

Figure 33:
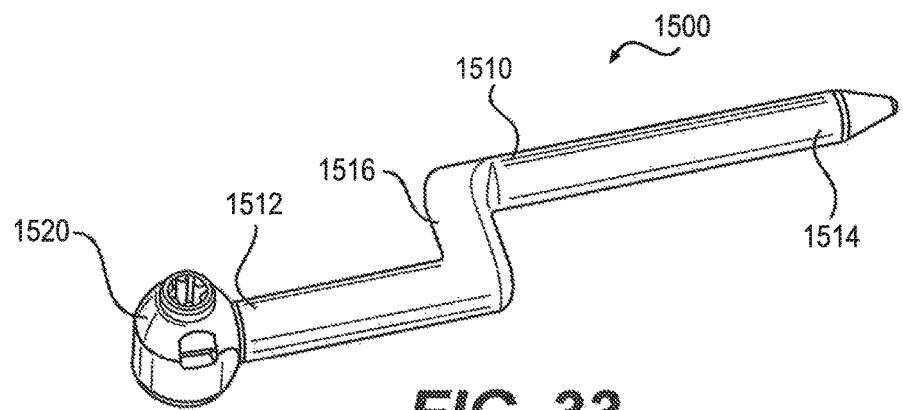
FIG. 33 is a perspective view of a lateral offset link connector according to a fifteenth exemplary embodiment.
Figure 34:
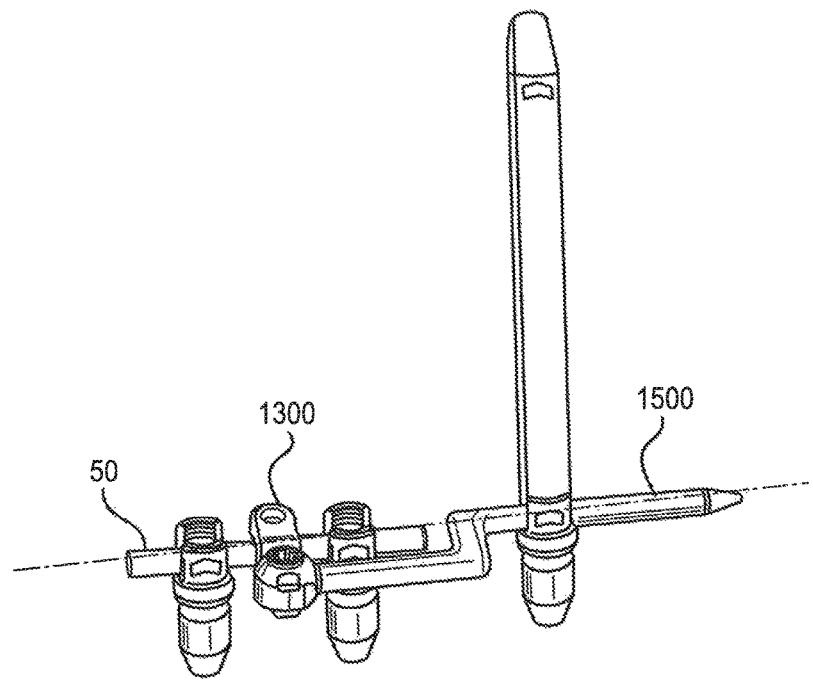
FIG. 34 is a perspective view of the lateral offset length connector shown in FIG. 33 and the lateral connector shown in FIG. 30, connected to an existing construct and supporting a new construct.

Referring now to FIGS. 33 and 34, a lateral offset link connector 1500 is shown. Link connector 1500 is similar to link connector 1200, with the exception that, instead of a straight elongate body 1210, link connector 1500 includes a body 1510 having a first end 1512 connected to a modular connection point 1520, similar to modular connection point 1220, a second, free end, 1514, and a lateral offset 1516, connecting first end 1512 with second end 1514. Lateral offset 1516 is sized to accommodate the same lateral offset as with lateral connector 1300.

As shown in FIG. 34, modular connection point 1520 can be connected to lateral connector 1300, which in turn is connected to a rod 50 in an existing construct such that second end 1514 extends generally co-linearly with rod 50, thereby allowing second end 1514, to effectively act as an extension of rod 50.

Figure 35:
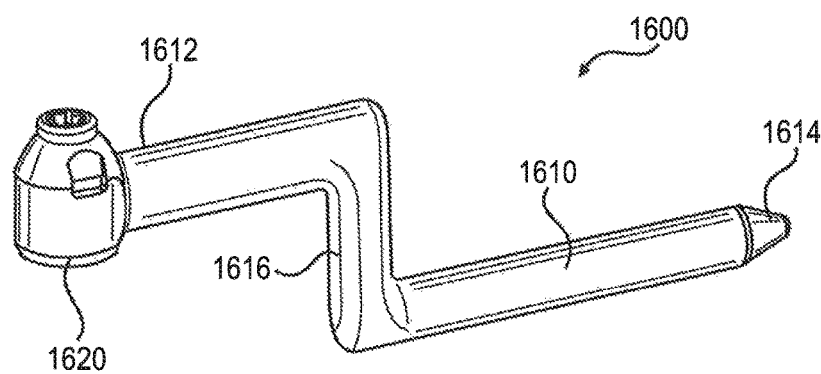
FIG. 35 is a perspective view of a sagittal offset link connector according to a sixteenth exemplary embodiment.
Figure 36:
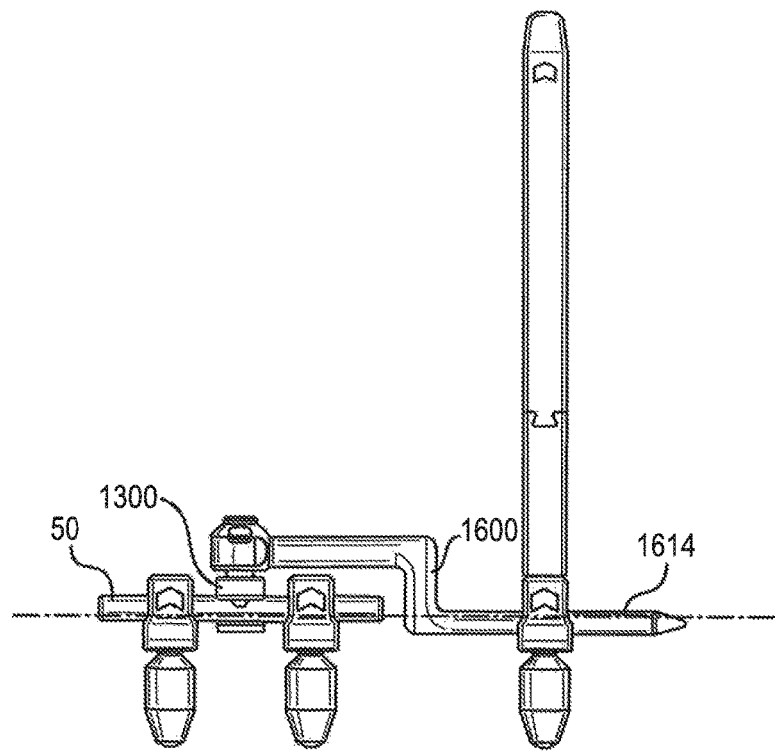
FIG. 36 is a side elevational view of the sagittal offset connector shown in FIG. 35, and the lateral connector shown in FIG. 30, connected to an existing construct and supporting a new construct.
Figure 37:
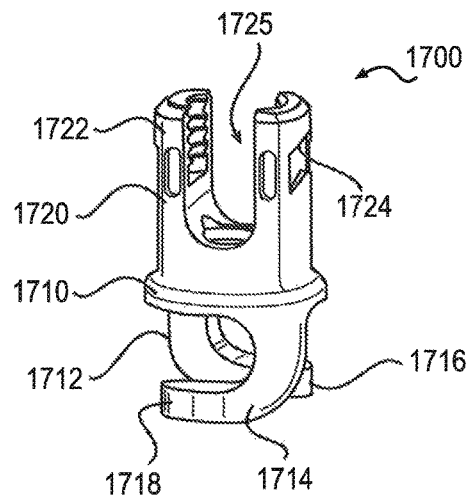
FIG. 37 is a perspective view of a revision connector according to a seventeenth exemplary embodiment.
Figure 38:
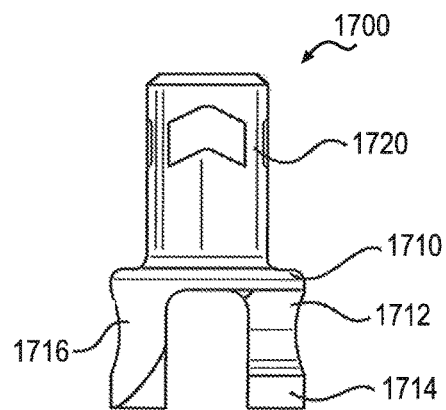
FIG. 38 is a side elevational view of the revision connector shown in FIG. 37.
Figure 39:
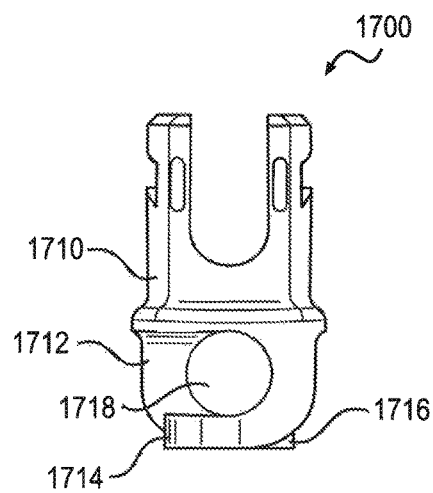
FIG. 39 is a front elevational view of the revision connector shown in FIG. 37.

Referring now to FIGS. 35 and 36, a sagittal offset link connector 1600 is shown. Link connector 1600 is similar to link connector 1500, with the exception that, instead of lateral offset 1516, link connector 1600 includes a body 1610 having a first end 1612 connected to modular connection point 1620, similar to modular connection point 1520, a second, free end, 1614, and a sagittal offset 1616, connecting first end 1612 with second end 1614. Sagittal offset 1616 is sized to allow connector 1600 to extend upward and over a screw head 60 when connected to a lateral connector 1300 and rod 50, as shown in FIG. 36.

As shown in FIG. 36, modular connection point 1620 can be connected to lateral connector 1300, which in turn is connected to a rod 50 in an existing construct such that second end 1614 extends generally co-linearly with rod 50, thereby allowing second end 1514, to effectively act as an extension of rod 50.

Referring now to FIGS. 37-57, a plurality of link connectors according to exemplary embodiments are shown. FIGS. 37-41 show a connector 1700 according to an exemplary embodiment. Connector 1700 is connected to an existing rod by a twisting connection and subsequent to attachment, a second, new rod may be positioned above and in-line with the existing rod. For example, connector 1700 may be inserted between two existing screw head 60, proximal to an adjacent level that needs additional fixation.

Connector 1700 includes a body 1710 having a connecting portion 1712 at a first end and a screw head portion 1720 at an opposing end. Connecting portion 1712 includes a pair of outwardly extending curved legs 1714, 1716 that extend downwardly from diametrically opposed sides of body 1710 in opposing directions, forming a passage 1718 sized to allow a rod 50 to extend therethrough.

Screw head portion 1720 includes a first arcuate portion 1722 and a second arcuate portion 1724 diametrically opposed from first arcuate portion 1722, forming a rod through-passage 1725 extending therebetween. The interior faces of each of arcuate portion 1722, 1724 are threaded at threads 1726 to accommodate insertion of a set screw 1730, shown in FIG. 41.

Figure 40:
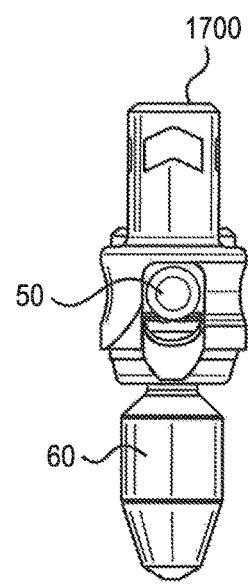
FIG. 40 is a side elevational view of the revision connector shown in FIG. 37, mounted on an existing construct.
Figure 41:
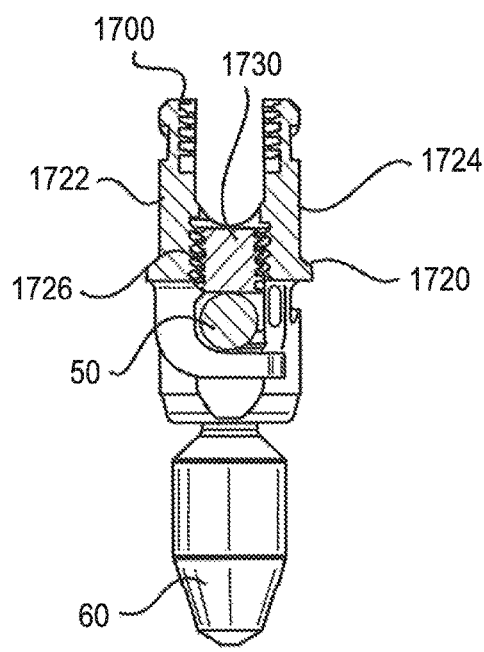
FIG. 41 is a sectional view of the revision connector and existing construct shown in FIG. 40.

To install connector 1700 on a rod 50, connector 1700 is inserted with rod through-hole 1725 facing in a medial/lateral direction and legs 1714, 1716 straddling rod 50, as shown in FIG. 40. Connector 1700 is then rotated 90° in situ, so that rod 50 extends through passage 1718, with legs 1714, 1716 extending underneath rod 50, as shown in FIG. 41. Set screw 1730 is then screwed downward to engage rod 50, securing connector 1700 to rod 50.

Figure 42:
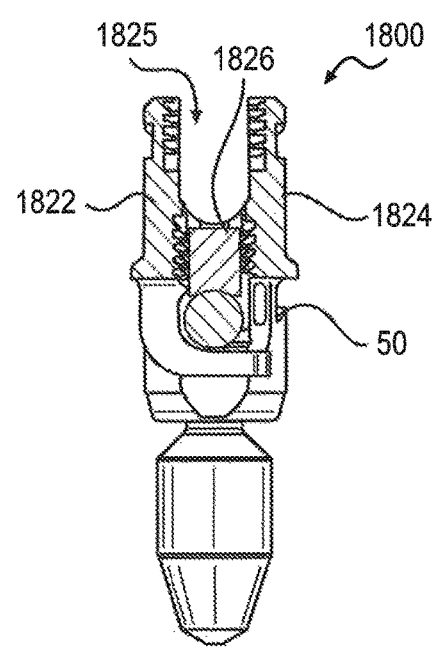
FIG. 42 is a sectional view of a revision connector according to an eighteenth exemplary embodiment, mounted on an existing construct.

In an alternative embodiment of a connector 1800, shown in FIG. 42, instead of threads 1726 and set screw 1730, lower interior surfaces of a first arcuate portion 1822 and a second arcuate portion 1824 are unthreaded and a wedge 1826 is advanced through a rod through-passage 1825 to engage rod 50 and secure rod 50 to connector 1800.

Figure 43:
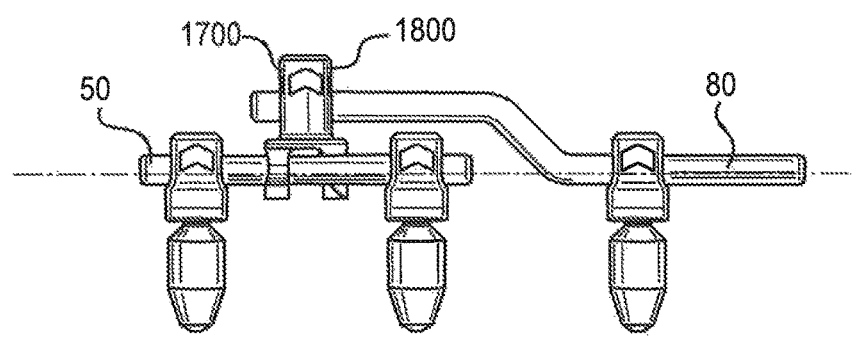
FIG. 43 is a side elevational view of the revision connector shown in FIG. 42, connecting a new construct to the existing construct.
Figure 47:
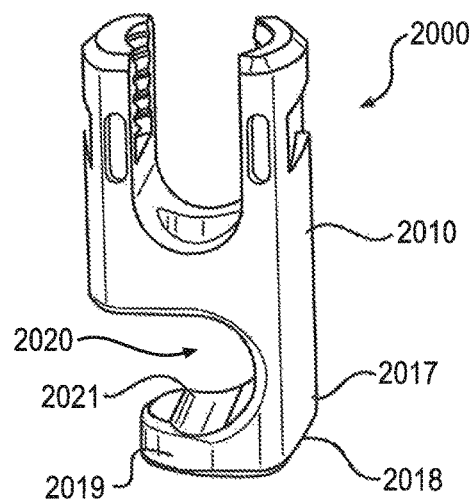
FIG. 47 is a perspective view of a revision connector according to a twentieth exemplary embodiment.

As shown in FIG. 43, either connector 1700 or connector 1800 can be attached to an existing rod 50 through passage 1718 and a new construct with a rod 80 can be inserted through rod through-passage 1725, 1825. A threaded cap (not shown) may then be engaged with the threaded portion on the top of the screw head portion 1720 to secure the rod 80 therein, thereby achieving fixation. If required, rod 80 can be bent to maintain new construct and an adjacent level with the existing rod 50.

FIGS. 44-46 show a connector 1900 according to an exemplary embodiment. Connector 1900 includes a body 1910 having a connecting portion 1912 at a first end and a head portion 1930 at an opposing end. Connecting portion 1912 includes a first generally longitudinally extending leg 1914 having a connection mechanism 1916 extending therethrough. In an exemplary embodiment, connection mechanism 1916 can be a set screw.

Connecting portion 1912 also includes a second leg 1917, having a first portion 1918 that extends generally longitudinally away from body 1910, generally parallel to first leg 1914. Second leg 1917 also includes a curved portion 1919 that curves an arcuate fashion toward first leg 1914, forming a passage 1920 therebetween. Passage 1920 is sized to allow connector 1900 to be connected to an existing rod 50, as shown in FIG. 46. Connection mechanism 1916 extends sufficiently through first leg 1914 to be able to extend into passage 1920.

Head portion 1930 includes a first arcuate portion 1932 and a second arcuate portion 1934 diametrically opposed from first arcuate portion 1932, forming a rod through-passage 1935 extending therebetween. Rod through-passage 1935 is sized to receive a rod 80 as part of a newly assembled construct, as shown in FIG. 46. If rod 80 is a "Z-Rod", rod 80 can be configured to achieve fixation at an adjacent level with rod 50.

Figure 48:
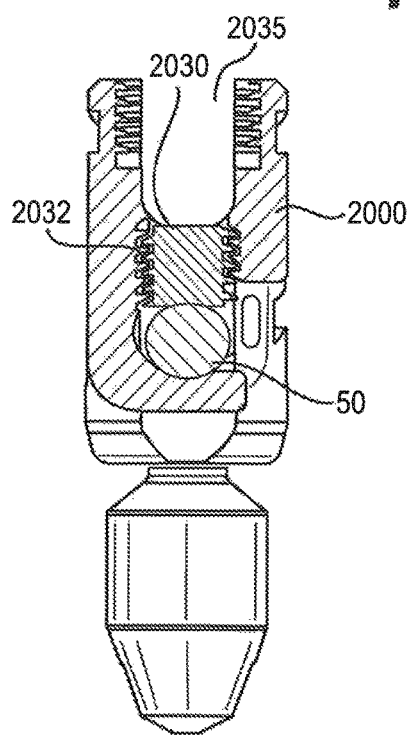
FIG. 48 is a sectional view of the revision connector shown in FIG. 47, with a set screw, mounted on existing construct.
Figure 49:
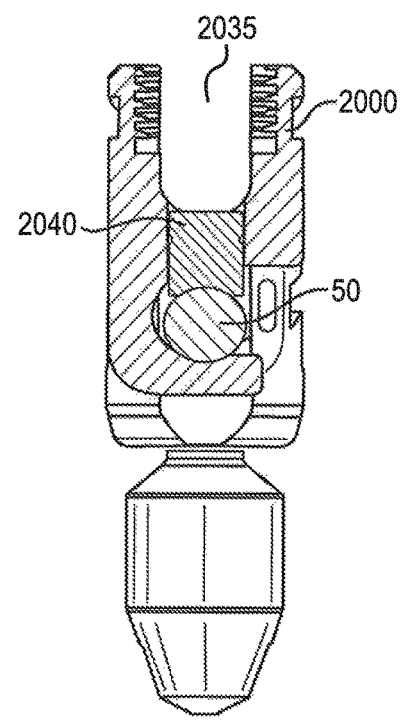
FIG. 49 is a sectional view of the revision connector shown in FIG. 47, with a wedge, mounted on existing construct.
Figure 50:
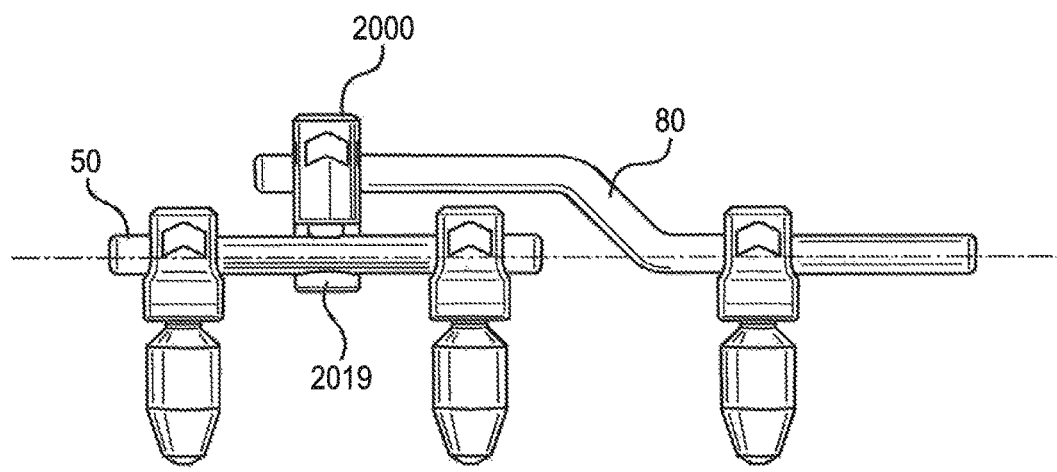
FIG. 50 is a side elevational view of the revision connector shown in FIG. 47, connecting a new construct to the existing construct.

FIGS. 47-50 show a connector 2000 according to an alternative exemplary embodiment. Connector 2000 is similar to connector 1900 as described above, with the exception that connector 2000 includes only a single leg 2017 extending downward from a body 2010. Leg 2017 includes a first portion 2018 that extends longitudinally outwardly, away from body 2010 and a curved portion 2019 that curves in an open hook fashion toward an opposing side of body 2010, forming an open passage 2020. Curved portion 2019 includes an arcuate support face 2021 faces open passage 2020 and serves as a support for an existing rod 50, as shown in FIG. 50.

FIG. 48 shows connector 2000 with an optional set screw 2030 can be threaded into a threaded passage 2032 to secure connector 2002 existing construct, such as, for example, rod 50.

Alternatively, FIG. 49 shows connector 2000 and optional wedge 2040 that can be used in place of set screw 2030, to secure rod 50 in connector 2000.

Similarly to connector 1900, connector 2000 has a rod through-passage 2035 is sized to receive a rod 80 as part of a newly assembled construct, as shown in FIG. 50. If rod 80 is a "Z-Rod", rod 80 can be configured to achieve fixation at an adjacent level with rod 50.

Figure 51:
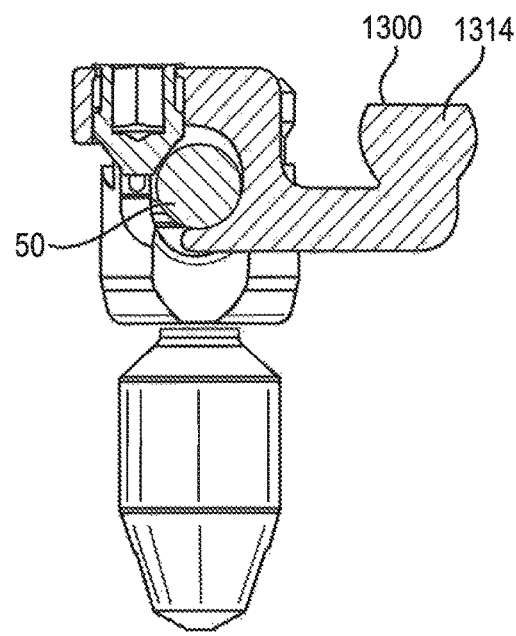
FIG. 51 is a sectional view of the lateral connector shown in FIG. 30, mounted on an existing construct.
Figure 52:
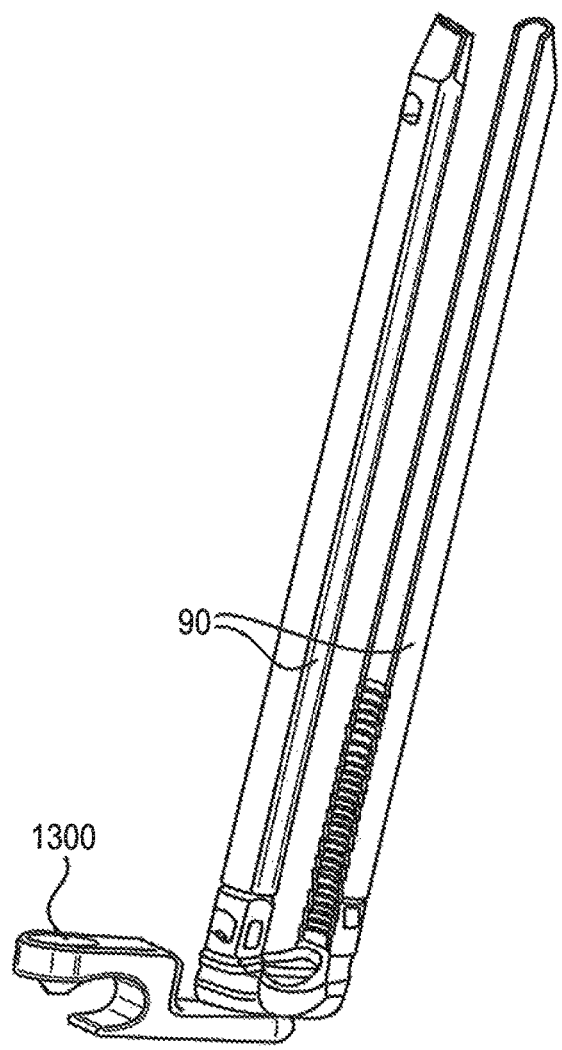
FIG. 52 is a perspective view of a new construct mounted on the lateral connector shown in FIG. 30.
Figure 53:
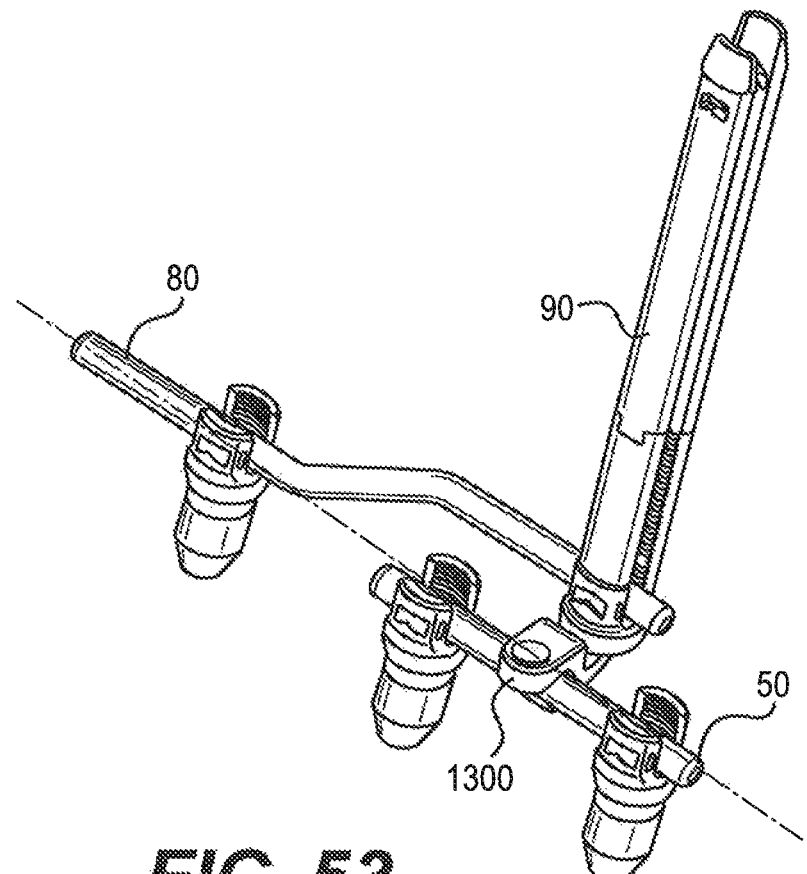
FIG. 53 is a perspective view of the lateral connector shown in FIG. 30, connecting the new construct to the existing construct.
Figure 54:
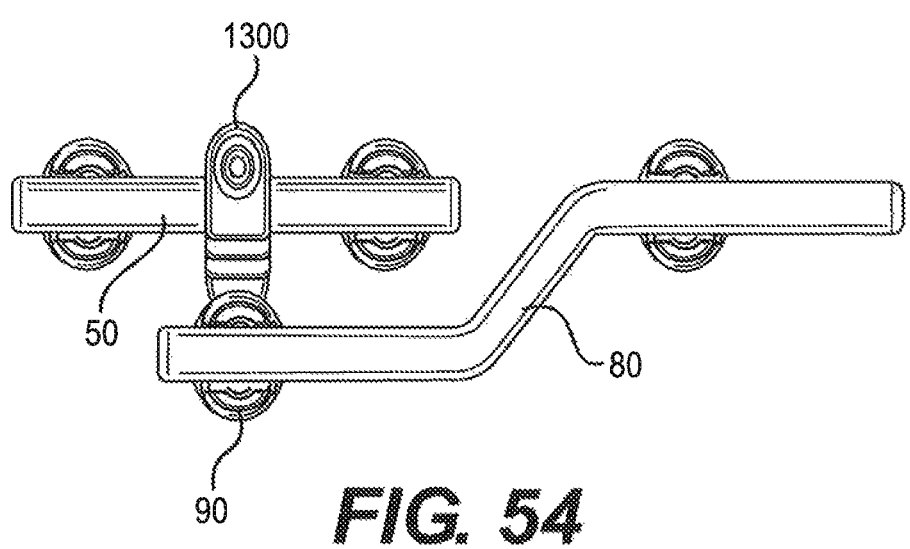
FIG. 54 is a top plan view of the lateral connector shown in FIG. 30, connecting the new construct to the existing construct.

Lateral connector 1300, shown previously in FIG. 30, can be used as shown in FIG. 51 to connect to a rod 50 in an existing construct. As shown in FIGS. 52-54, new construct 90 can be attached at connection point 1314 to achieve fixation. Instead of installing connector 1200 at an angle, as shown in FIG. 32, FIGS. 53 and 54 show that, when rod 80 is a Z-Rod, lateral connector 1300 can be used to support rod 80 such the rod 80 extends collinear with existing rod 50.

Figure 57:
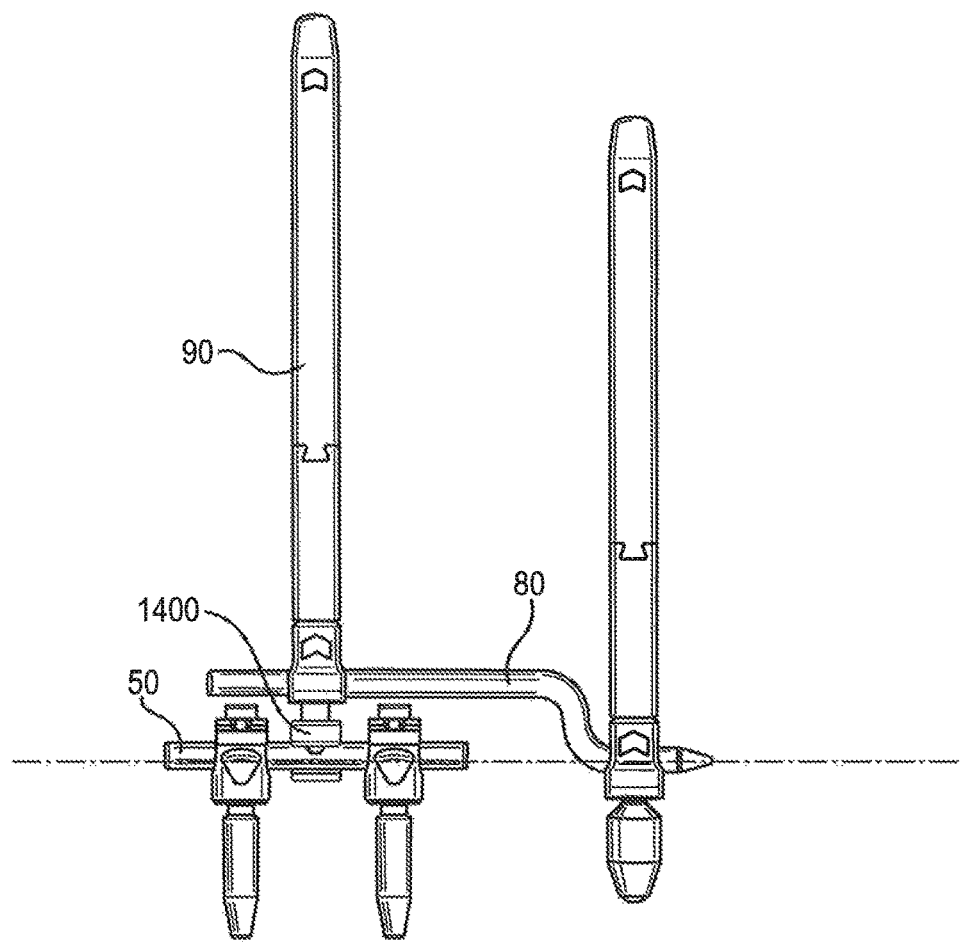
FIG. 57 is a side elevational view of the top loading connector shown in FIG. 31, connecting the new construct to the existing construct.

Top loading connector 1400, shown previously in FIG. 31, can be used. As shown in FIGS. 55-57 to connect to an existing rod 50. In an existing construct. As shown in FIGS. 56 and 57, new construct 90 can be attached at connection 1422 to achieve fixation. As will be appreciated by those skilled in the art, after the rod 80 is secured and attached to the existing rod 50 and the adjacent vertebra or vertebrae using a minimally invasive surgical (MIS) approach, the extensions may be detached from the tulips, thereby leaving the connector 1400 and rod 80 subcutaneously implanted in the patient.

Figure 58:
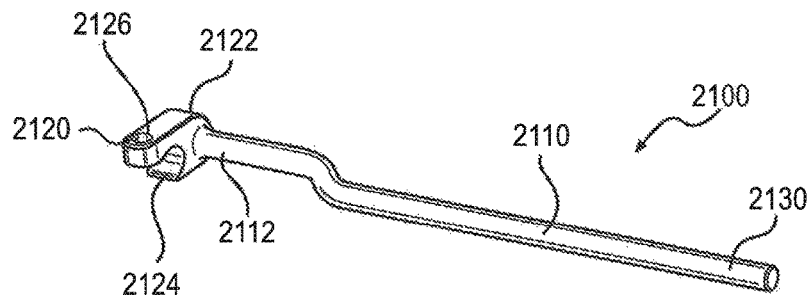
FIG. 58 is a perspective view of an offset revision rod according to a twenty-first exemplary embodiment.
Figure 59:
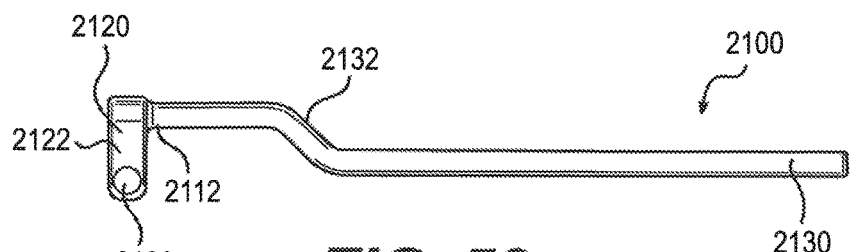
FIG. 59 is a top plan view of the offset revision rod shown in FIG. 58.

Referring now to FIGS. 58 and 59, an offset revision rod 2100 according to an exemplary embodiment is shown. Revision rod 2100 has an elongate body 2110 having a first end 2112, with an integrated single open clamp 2120 extending laterally therefrom. Claim 2120 includes a body 2122 with a clamp portion 2124 sized to accept and retain a rod (not shown) between proximal existing screw heads (also not shown). Body 2122 also includes a threaded opening 2126 sized to accept a fastener, such as a set screw (not shown), that can be screwed downwardly to secure the rod into clamp portion 2124.

Body 2110 further has a second end 2130 an offset 2132, between first end 2112 and second and 2130, such that first and 2112 and second end 2130 extend parallel to each other. Rod 2100 allows a fixation to be extended to adjacent level with a single implant. Offset 2132 allows rod 2100 to navigate around a most proximal screw head (not shown) in an existing construct.

Figure 60:
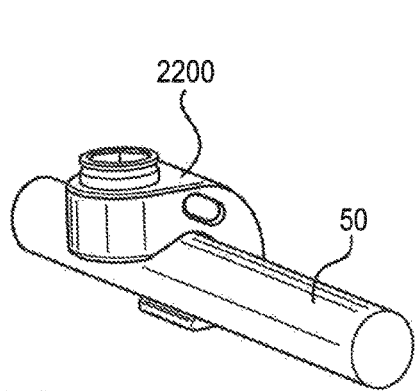
FIG. 60 is a side elevational view of a distraction/compression clamp according to a twenty-second exemplary embodiment.
Figure 61:
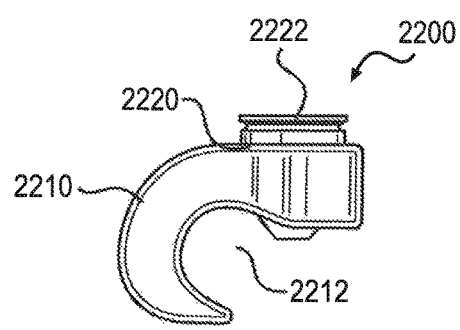
FIG. 61 is a perspective view of the distraction/compression clamp shown in FIG. 60, connected to existing construct.

A distraction/compression clamp 2200 is shown in FIGS. 60-61. Clamp 2200 has a single open clamp 2210 with a through passage 2212 sized to accept a rod 50 inserted therethrough. Claim 2200 also includes a threaded opening 2220 that is sized to accept a set screw 2222 to secure clamp 2200 to rod 50. Clamp 2200 can provide a fixed point for distraction and/or compression.

A double-headed lateral connector 2300 is shown in FIGS. 62-64. Connector 2300 includes a body 2310 having a first screw head 2320 (e.g., a first tulip) having a passage 2322 and a second screw head 2330 (e.g., a second tulip) having a passage 2332. Screw heads 2320 and 2330 are separated from each other by a connecting member 2340. Passage 2322 is sized to accept a first rod (not shown) from an existing construct and passage 2332 is sized to accept a second rod (not shown) from the new construct in order to extend the existing construct to an adjacent level. A threaded cap (not shown) may then be engaged with each of the threaded portions on the tops of the screw heads 2320 and 2330 to secure the respective rods therein, thereby coupling the rods substantially parallel to one another. While FIG. 62 shows screw heads 2320, 2330 extending parallel to each other, those skilled in the art will recognize that screw heads 2320, 2330 can also be offset or angled relative to each other.

While FIG. 62 shows connecting member 2340 connecting first screw head 2320 and second screw head 2330 only at the bottom portion of connector 2300, FIGS. 63 and 64 show a connecting member 2350 that connects first screw head 2320 and second screw head 2330 along the length of the screw heads.

Figure 65:
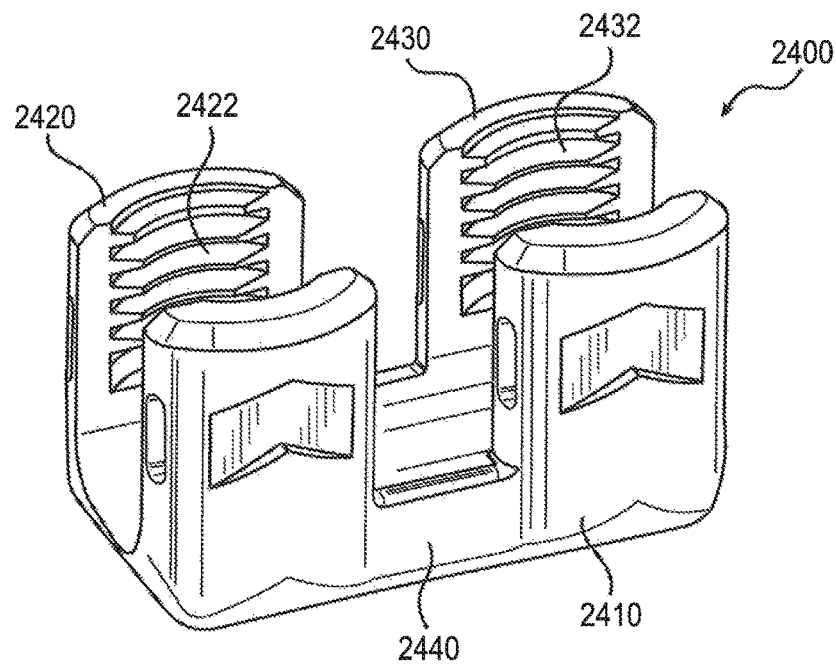
FIG. 65 is a perspective view of a double head in-line connector according to a twenty-fourth exemplary embodiment.

FIG. 65 shows a double-headed in-line connector 2400 according to an exemplary embodiment. While lateral connector 2300 discussed above laterally connects adjacent rods, in-line connector 2400 connects adjacent rods longitudinally. Connector 2400 includes a body 2410 having a first screw head 2420 having a passage 2422 and a second screw head 2430 having a passage 2432. Screw heads 2420 and 2430 are separated from each other by a connecting member 2440. Passage 2422 is sized to accept a rod (not shown) from an existing construct and passage 2432 is sized to accept a rod (not shown) from the new construct in order to extend existing construct to an adjacent level. A threaded cap (not shown) may then be engaged with each of the threaded portions on the tops of the screw heads 2420 and 2430 to secure the respective rods therein, thereby coupling the rods substantially in-line with one another. While FIG. 65 shows screw heads 2420, 2430 extending parallel to each other, those skilled in the art will recognize that screw heads 2420, 2430 can also be offset or angled relative to each other.

Figure 66:
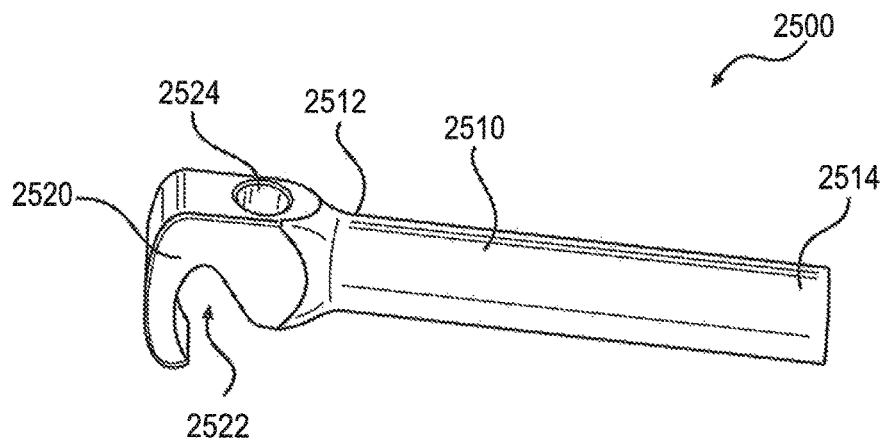
FIG. 66 is a perspective view of a J-hook connector according to a twenty-fifth exemplary embodiment.

A J-hook connector 2500 according to an exemplary embodiment is shown in FIG. 66. Connector 2500 includes an elongate body 2510 having a first end 2512 and a second end 2514. First end 2512 includes an open clamp 2520 attached thereto. Clamp 2520 includes a passage 2522 sized to allow a rod (not shown) to be inserted therethrough. Clamp 2520 also includes a threaded opening 2524 sized to allow a set screw (not shown) to be inserted therethrough to secure the rod within opening 2524.

Connector 2500 is used to connect a rod (not shown) on a first side of a patient's spine with first end 2512, and to insert second end 2514 into a screw head (not shown) on an opposing side of the patient's spine.

Figure 67:
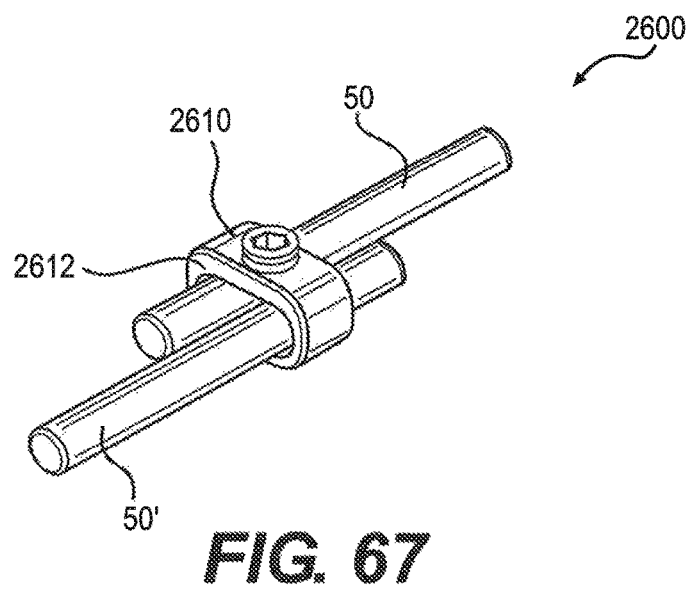
FIG. 67 is a perspective view of a modular head open lateral connector with connected rods according to a twenty-sixth exemplary embodiment.
Figure 68:
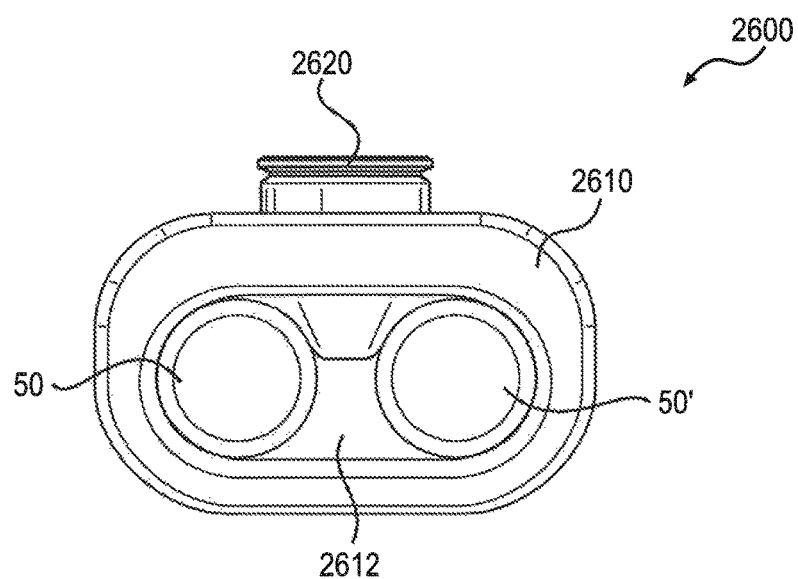
FIG. 68 is a side elevational view modular open head lateral connector with connected rods shown in FIG. 67.

A parallel connector 2600 according to an exemplary embodiment is shown in FIGS. 67 and 68. Connector 2600 includes a body 2610 having a generally oblong opening 2612 that is sized to allow the insertion of 2 rods 50, 50' therethrough to extend the length of rod 50, with rod 50'. As shown in FIG. 68, a single set screw 2620 extends through body 2610 between rods 50, 50' to secure rods 50, 50' to connector 2600. While a single set screw 2600 is shown, those skilled in the art will recognize that to set screws, one located above each of rod 50, 50', can be used to secure rods 50, 50', respectively, to connector 2600.

Figure 69:
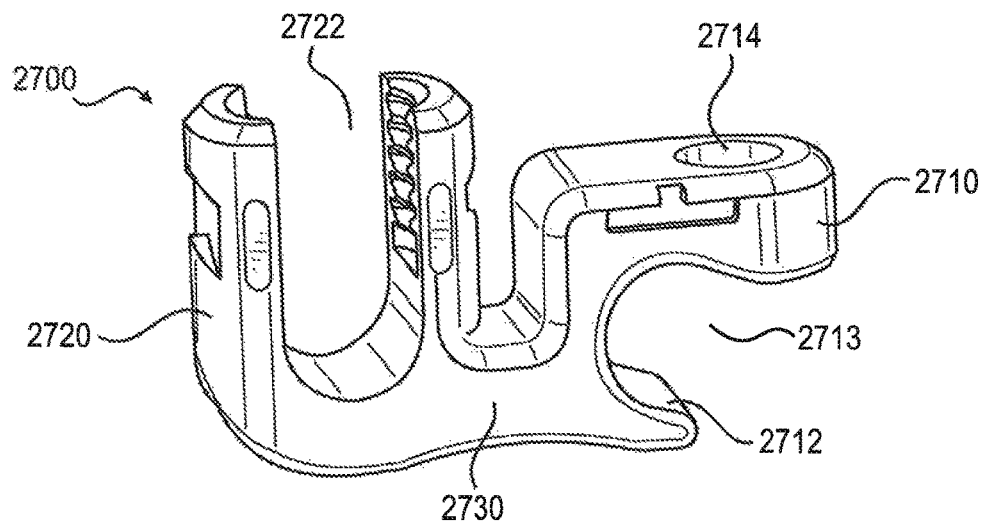
FIG. 69 is a perspective view of a single head open lateral connector according to a twenty-seventh exemplary embodiment.

FIG. 69 shows a single open head lateral connector 2700 according to an exemplary embodiment. Connector 2700 includes an open clamp 2710 and an adjacent screw head 2720, coupled to each other by a connector 2730.

Open clamp 2710 includes an arcuate portion 2712, forming a through-passage 2713 that is sized to accept a rod (not shown) from an existing construct inserted therein. Open clamp 2710 also includes a threaded opening 2714 sized to accept a set screw (not shown) that can be threaded into through-passage 2713 to secure the rod in through-passage 2713.

Screw head 2720 includes a passage 2722 that is sized to allow the insertion of a rod (not shown) in new construct therein. Through-passage 2713 and passage 2722 extend in a common plane such that the rod in the new construct is at the same level as the rod in the existing construct.

Figure 70:
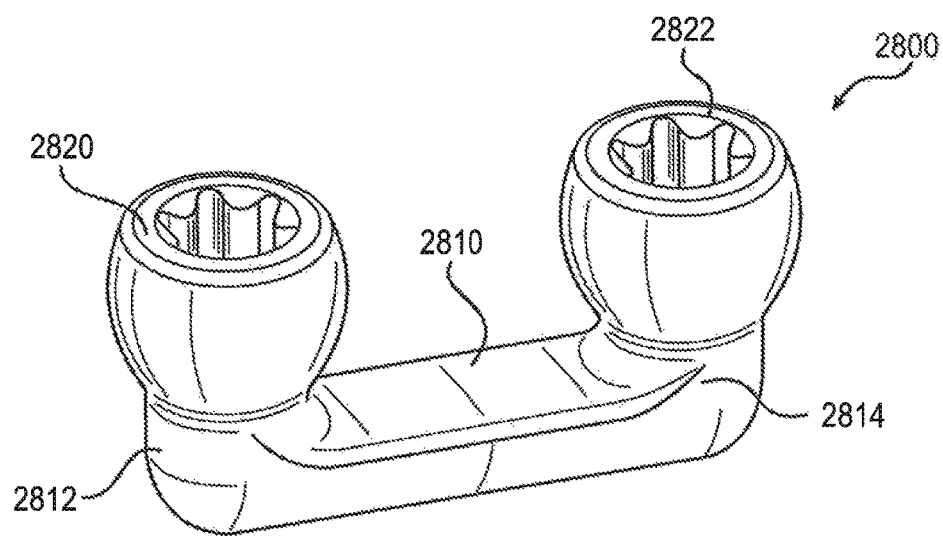
FIG. 70 is a perspective view of a double modular lateral connector according to a twenty-eighth exemplary embodiment.

FIG. 70 shows a double modular lateral connector 2800 according to an exemplary embodiment. Connector 2800 includes an elongate body 2810 having a first end 2812 and a second end 2814, distal from first end 2812. Each end 2812, 2814 includes a point of attachment 2820, 2822, respectively for the attachment of modular screw heads side-by-side, as shown, allowing for options variety of screw heads. Each point of attachment 2820, 2822 may be in the form of a post having a partially-spherical outer surface with a substantially flatten top surface having one or more recesses therein. In one embodiment, a tulip can be placed on attachment point 2820 before or after connecting to an existing rod (not shown). The new rod (not shown) can then be introduced, for example, in a second tulip attached to attachment point 2822 in order to extend the fixation at an adjacent level. In the alternative, a rod 1200, for example, shown in FIG. 28, with an integrated attachment point 1220 can connect to one or more of the posts on connector 2800. While connection points 2820 and 2822 are shown as being parallel to each other, those skilled in the art will recognize that connection points 2820, 2822 can also be offset or angled relative to each other.

Figure 71:
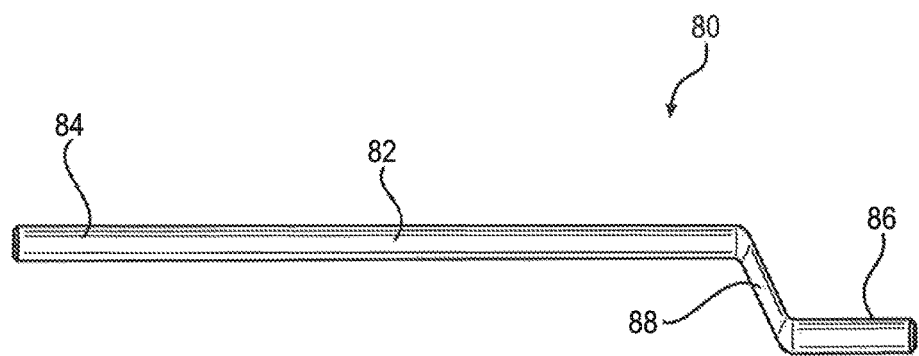
FIG. 71 is a side elevational view of a Z-rod according to a twenty-ninth exemplary embodiment.

FIG. 71 shows a Z-rod 80 according to an exemplary embodiment. As shown previously throughout, rod 80 is used to link to an existing construct at an adjacent level. Rod 80 includes a generally elongate body 82 having a first end, a second end 86, distal from first end 84, and a bent portion 88, located along body 82, between first and 84 and second end 86. The position and offset distance of bend portion 88 can be varied depending upon the location of existing construct and the particular patient anatomy.

Figure 72:
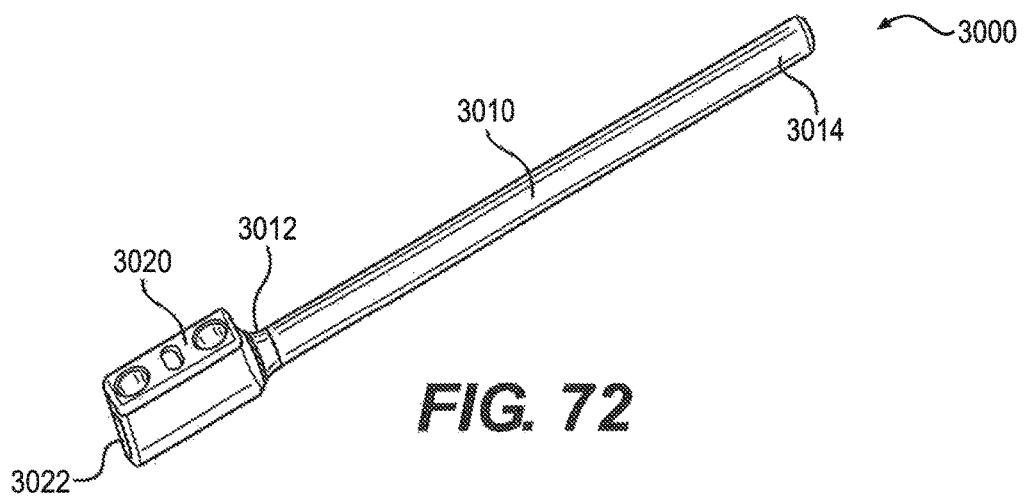
FIG. 72 is a perspective view of an in-line connector with integrated rod according to a thirtieth exemplary embodiment.

FIG. 72 shows an in-line connector with an integrated rod 3000 according to an exemplary embodiment. Rod 3000 includes an elongate body 3010 having a first end 3012 and a second end 3014, distal from first end 3012. A closed connector 3020 is attached to first end 3012. Connector 3020 includes an opening 3022, in line with, and, distal from body 3010 into which an existing rod (not shown) is inserted to extend the length of an existing construct at an adjacent level. Then one or more fasteners or set screws (not shown) may be positioned in the one or more openings in the connector portion 3020 to secure the existing rod therein, thereby coupling the new rod extension to the existing rod construct.

Figure 73:
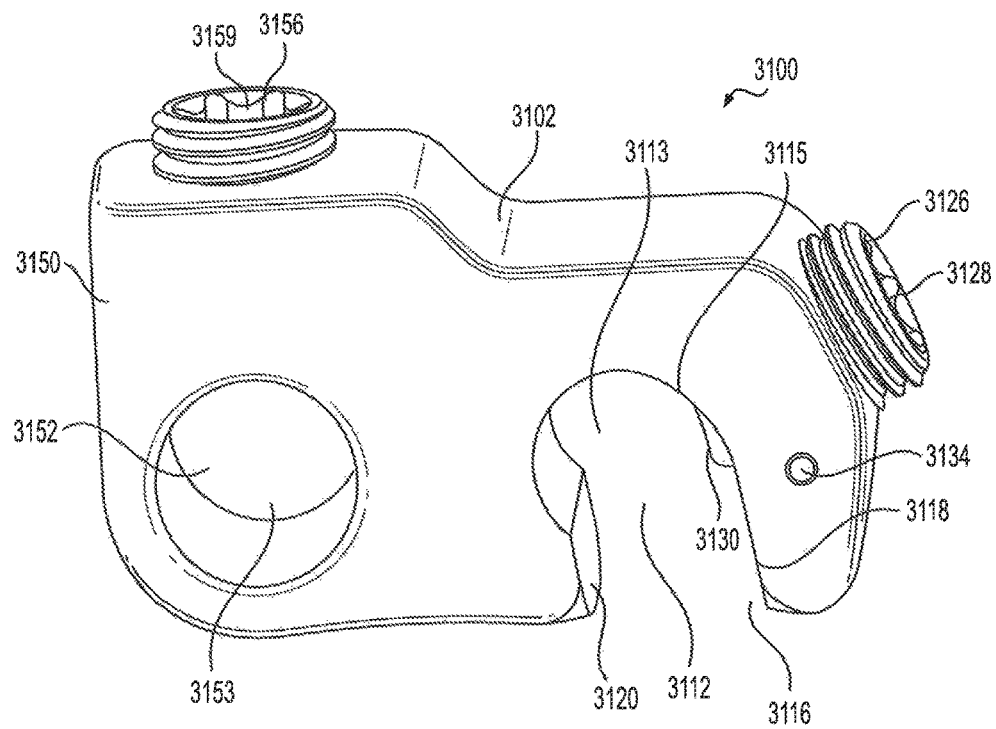
FIG. 73 is a perspective view of a top loading lateral connector with a closed connector portion according to a thirty-first exemplary embodiment.
Figure 74:
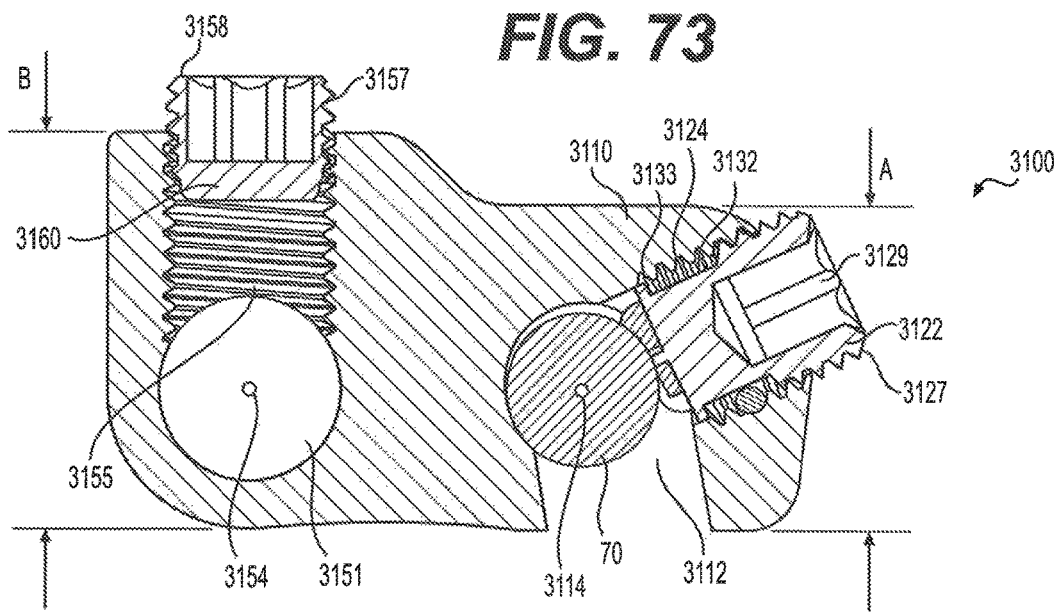
FIG. 74 is a sectional view of the connector shown in FIG. 73.

FIGS. 73 and 74 show a top loading connector 3100 according to an exemplary embodiment. Connector 3100 is a top loading lateral connector that has a body 3102 having two clamping portions that are laterally offset from each other. A first clamping portion 3110 has a first axial passage 3112 having a first longitudinal axis 3114 extending therethrough. Referring to FIG. 74, axis 3114 extends perpendicularly outwardly from the plane of the paper of the Figure.

First passage 3112 is sized to allow a first rod, such as a rod 70 (shown in FIG. 3) to be inserted thereinto. First passage 3112 is generally U-shaped and has a closed top portion 3113 that has a generally arcuate top wall 3115 and a bottom portion having an opening 3116 in communication with the rest of first passage 3112. Opening 3116 is defined by generally parallel opposing sidewalls 3118, 3120 that extend at an angle oblique to the vertical relative to body 3102 as shown in FIG. 74.

Opening 3114 is sufficiently large to allow opening 3114 to extend over rod 70 such that first clamping portion 3110 can be placed over rod 70 and slid over rod 70 until rod 70 is located in top portion 3113, as shown in FIG. 74.

A first securing mechanism 3122 is rotatably connected to first clamping portion 3110 and is adapted to extend into first passage 3112 to releasably secure first rod 70 in first passage 3112. First securing mechanism 3122 includes a threaded through-hole 3124 extending through body 3102 to first passage 3112 and a set screw 3126 that is rotatably inserted into through-hole 3124. A first end 3128 of set screw 3126 includes a threaded exterior 3127 that threadingly engages threaded through-hole 3124. First end 3128 of set screw 3126 also includes a receiver 3129, such as, for example, for an Allen wrench or a Torx® wrench, and an engagement end 3130 that extends into first passage 3112 to bias rod 70 against top wall 3115 in top portion 3113 to secure connector 3100 to rod 70.

Set screw 3126 also includes a securing channel 3132 that extends around a periphery of set screw 3126 between first end 3128 and securing end 3130. Securing channel 3132 includes a flared portion 3133 at a bottom end thereof. A retaining pin 3134 extends through body 3102 generally parallel to axis 3114 such that retaining pin 3134 extends through securing channel 3132 between set screw 3126 and through-hole 3124 and between threaded exterior 3127 and flared portion 3133 such that flared portion 3133 is stopped by retaining pin 3134 if set screw 3126 is attempted to be removed from body 3102.

Set screw 3126 extends at an angle oblique to the horizontal. Set screw 3126 can be angled at such an angle to give the implanting physician a better angle to access set screw 3126 than if set screw 3126 extended in a horizontal plane.

A second clamping portion 3150 has a second passage 3151 that has a second longitudinal axis 3154 extending therethrough. Second passage 3151 comprises a generally circular axial passage, or through-opening, 3153. Second longitudinal axis 3154 is parallel to first longitudinal axis 3114, and is sized to allow a second rod, such as, for example, a rod 80 shown in FIG. 71, to be inserted thereinto along second longitudinal axis 3154.

Similar to first clamping portion 3110, second clamping portion 3150 includes a second securing mechanism 3152 that is adapted to releasably secure second rod 80 in second passage 3153. Second securing mechanism 3150 includes a threaded through-hole 3155 and a set screw 3156 that is rotatably inserted into through-hole 3124. A first end 3158 of set screw 3156 includes a threaded exterior 3157 that threadingly engages threaded through-hole 3155. First end 3158 of set screw 3156 also includes a receiver 3159, such as, for example, for an Allen wrench or a Torx® wrench, and an engagement end 3160 that extends into second passage 3151 to bias a rod 80 (not shown) against the wall of through-opening 3153 to secure connector 3100 to rod 80.

A shown in FIG. 74, first clamping portion 3120 has a height "A" and second clamping portion 3150 has a height "B" that is higher than height "A".

Connector 3100 can be used to add a new construct to an existing construct. By way of example only, opening 3114 can be inserted over inserting first rod 70 in an existing construct. First connecting portion 3110 can be secured to first rod 70 by rotating securing mechanism 3122 and advancing securing mechanism 3122 into axial passage 3112 to secure first connecting portion 3110 to first rod 70. Second rod 80 can be inserted through through-opening 3153 and secured by set screw 3156.

Figure 75:
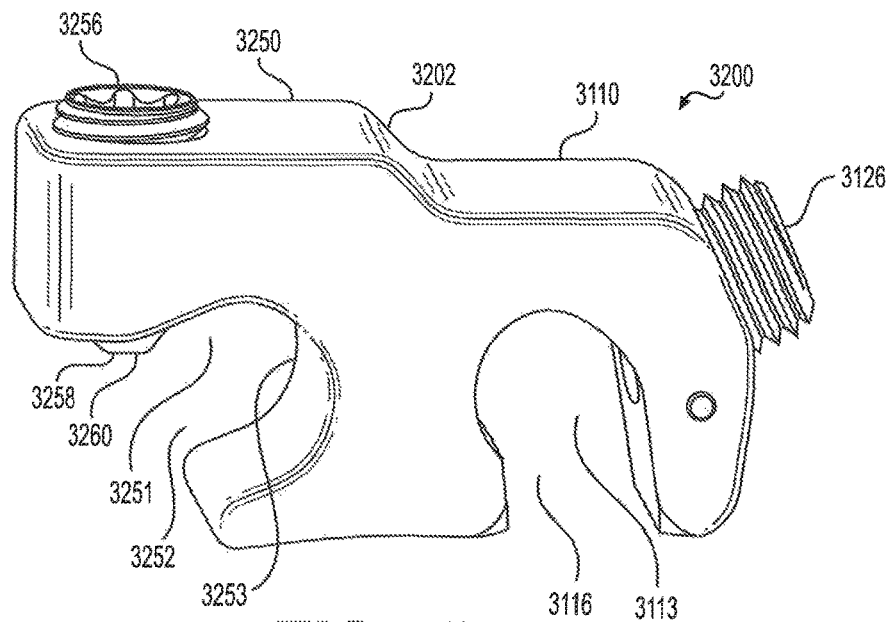
FIG. 75 is a perspective view of a top loading lateral connector with an open side connector portion according to a thirty-second exemplary embodiment.

An alternative embodiment of a connector 3200 is shown in FIG. 75. Connector 3200 is similar to connector 3100 with the exception of second connecting portion 3250, which differs from second connecting portion 3150 in connector 3100 as described below.

Instead of generally circular passage 3151, in connector 3200, a second connector portion 3250 has second passage 3251 with an opening 3252 defined by a generally U-shaped wall 3253 that allows connector 3200 to be inserted over second rod 80 (not shown) instead of requiring second rod 80 to slide through passage 3251. Also, connector 3200 can be reversed such that second connecting portion 3250 can be secured to existing rod 70 and first connecting portion 3110 can be secured to a new construct, such as rod 80.

A securing mechanism 3252 uses a different set screw 3256 than set screw 3156. Set screw 3256 has an engagement end 3260 having a tapered perimeter 3258 such that tapered perimeter 3258 engages second rod 80 and biases second rod 80 against wall 3153.

Figure 76:
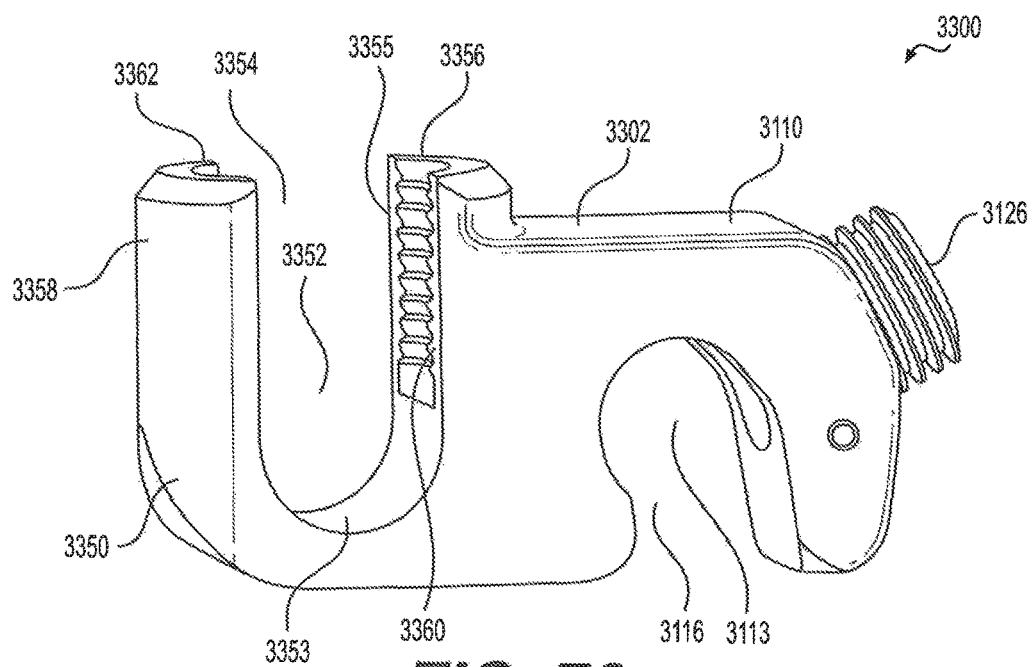
FIG. 76 is a perspective view of a top loading lateral connector with a tulip portion according to a thirty-third exemplary embodiment.

Another alternative embodiment of a connector 3300 is shown in FIG. 76. Connector 3300 is similar to connector 3100 with the exception of second connecting portion 3350, which differs from second connecting portion 3150 in connector 3100 as described below. In an exemplary embodiment, second connection portion 3350 can be a "tulip style" connection, as is recognized by those skilled in the art.

Second connecting portion 3350 has a second passage 3352 with a generally U-shaped opening 3354 that opens at the top of second connecting portion 3350 and has a closed bottom wall 3353 that is arcuate in shape. Opening 3354 is defined by bottom wall 3353 and opposing generally planar side walls 3356, 3358 that each include threads 3360, 3362, respectively, that extend away from their respective walls 3356, 3338. Threads 3360, 3362 are used to receive a securing member, such as set screw 3256 (shown in FIG. 75).

Opening 3354 allows for the insertion of rod 80 (not shown), which has a circular cross-section, or some other construct with a non-circular cross-section, such as an oblong cross-section.

Figure 77:
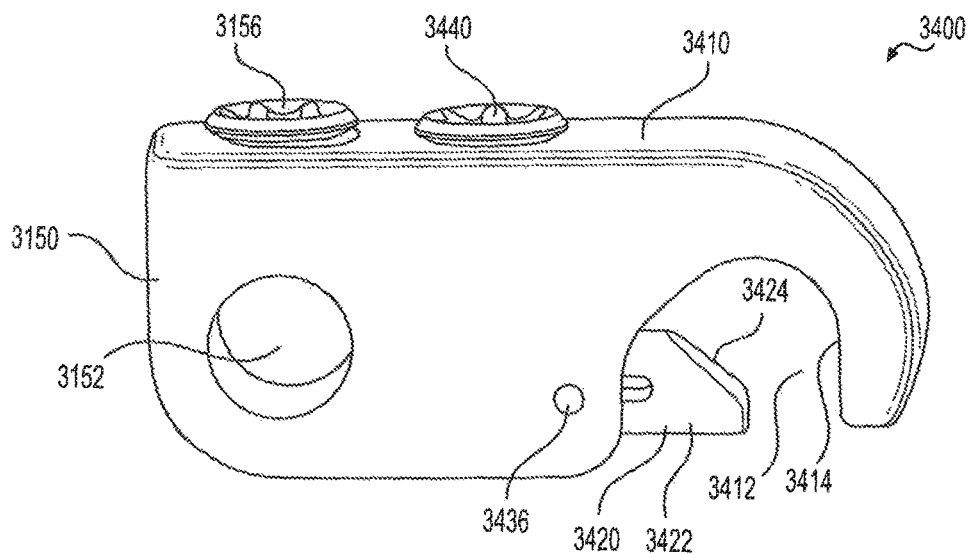
FIG. 77 is a perspective view of a top loading lateral connector with a sliding member according to a thirty-fourth embodiment.
Figure 78:
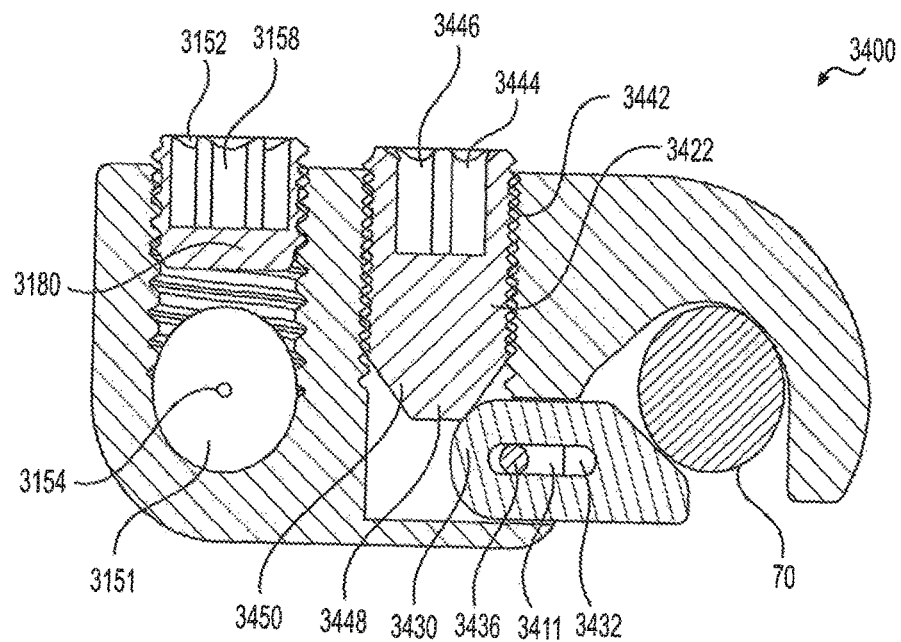
FIG. 78 is a cross-sectional view of the connector shown in FIG. 77.

Another alternative embodiment of a sliding member top loading connector 3400 is shown in FIGS. 77-78. Connector 3400 is similar to connector 3100 with the exception of first connecting portion 3410, which differs from first connecting portion 3110 in connector 3100 as described below.

First connecting portion 3410 includes an open first passage 3412 defined by an arcuate wall 3414 that allows connector 3400 to be placed over a member, such as rod 70 (shown in FIG. 78), in an existing construct to add on to the existing construct.

First connecting portion 3410 includes a securing mechanism 3422 having a locking portion in the form of a member 3420 that is extendible into first passage 3412. Member 3420 is translatably located in a horizontal passage 3411 that communicates with first passage 3412.

Member 3420 is a generally cylindrical member that is longitudinally translatable between a first rod unlocking position and a first rod locking position to releasably secure rod 70 against generally arcuate wall 3414 that defines first passage 3412. Member 3420 has a rod engaging surface 3424 that engages rod 70 and biases rod 70 against wall 3414. Rod engaging surface 3424 is angled with respect to the horizontal such that, as member 3420 is translated from the rod unlocking position to the rod locking position (as shown in FIG. 78), rod 70 slides up rod engaging surface 3424 to provide a secure connection between connector 3400 and rod 70.

Member 3420 also includes a cam surface 3430 that is acted upon to move member 3420. In an exemplary embodiment, cam surface 3430 is an arcuate surface, although those skilled in the art will recognize that cam surface 3430 can be another shape, such as for example, a sloped surface, so that, when cam surface 3430 is acted upon by another member from above, member 3420 translates into passage 3412.

Member 3420 includes a longitudinal slot 3432 that extends within member 3420 between rod engaging surface 3424 and cam surface 3430. A retaining pin 3436 extends through slot 3432 and retains member 3420 within horizontal passage 3411.

Securing mechanism 3422 also includes a rotating portion in the form of a set screw 3440 that is adapted to engage cam surface 3430 of member 3420 such that member 3420 is longitudinally translatable into engagement with first rod 70. Set screw 3440 is threadingly mounted in a threaded screw passage 3442 that is in communication with horizontal passage 3411. Set screw 3440 includes a first end 3444 having a receiver 3446, such as, for example, for an Allen wrench or a Torx® wrench, and an engagement end 3448 having a tapered tip 3450 such that, as set screw 3440 is screwed downwardly into screw passage 3442, tapered tip 3450 engages cam surface 3430 and longitudinally translates member 3420 into passage 3412 and into engagement with rod 70.

Figure 79:
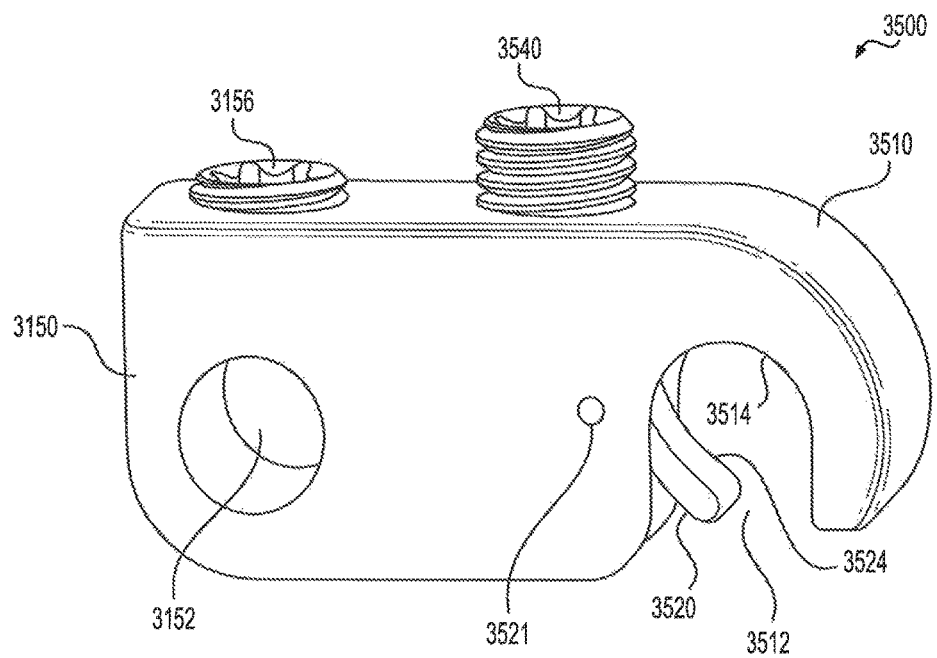
FIG. 79 is a perspective view of a top loading connector lateral with a pivoting member according to a thirty-fifth embodiment.
Figure 80:
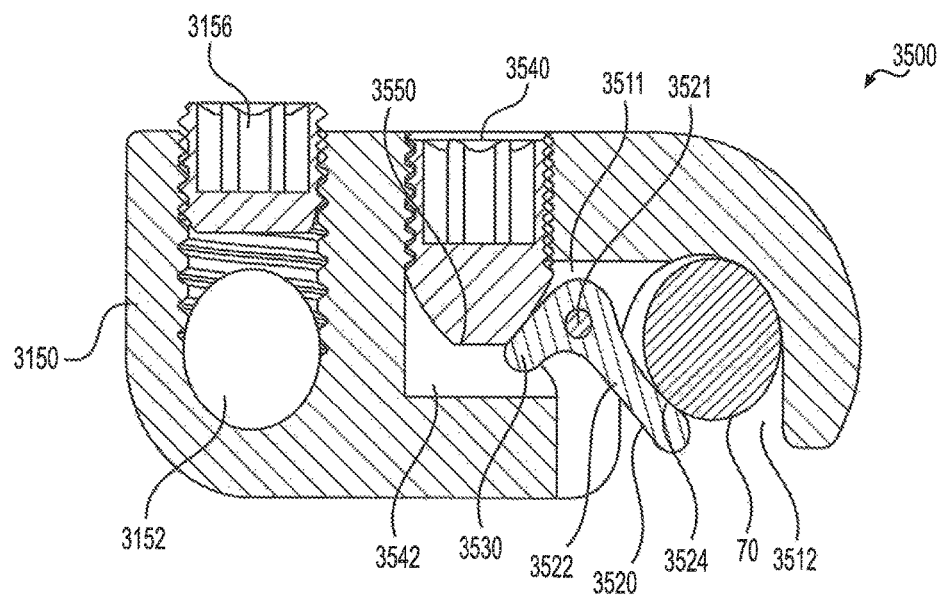
FIG. 80 is a cross-sectional view of the connector shown in FIG. 79.
Figure 81:
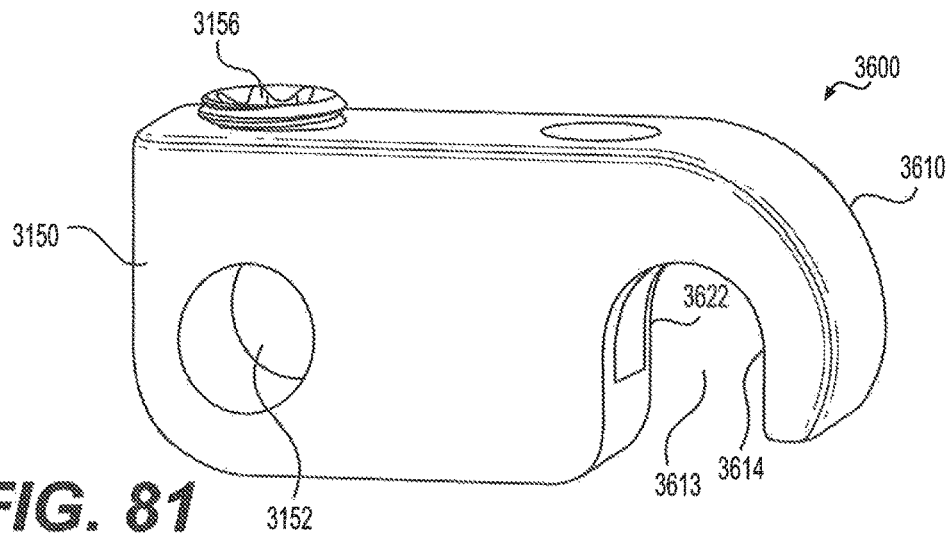
FIG. 81 is a perspective view of a top loading lateral connector with a cam lock according to a thirty-sixth embodiment.
Figure 82:
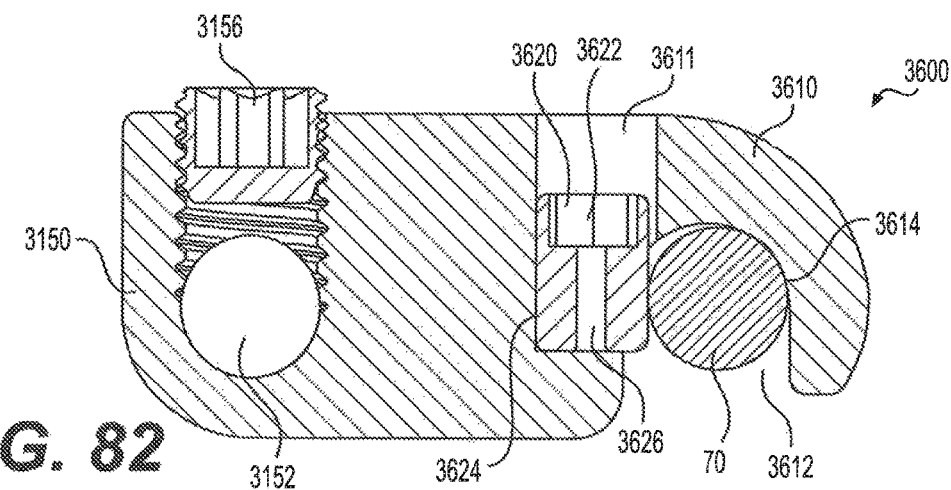
FIG. 82 is a sectional view of the connector shown in FIG. 81, with the cam in an unlocking position.
Figure 83:
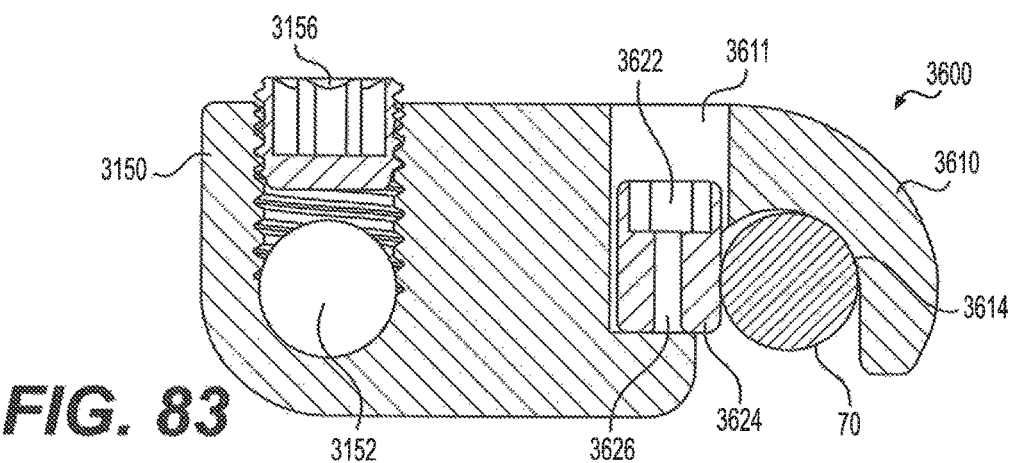
FIG. 83 is a sectional view of the connector shown in FIG. 81, with the cam in an locking position.

Still another alternative embodiment of a pivoting member top loading connector 3500 is shown in FIGS. 79-80. Connector 3500 is similar to connector 3100 with the exception of first connecting portion 3510, which differs from first connecting portion 3110 in connector 3100 as described below.

First connecting portion 3510 includes an open first passage 3512 defined by an arcuate wall 3514 that allows connector 3500 to be placed over a member, such as rod 70 (shown in FIG. 80), in an existing construct to add on to the existing construct.

First connecting portion 3510 includes a securing mechanism 3522 having a locking portion in the form of a member 3520 that is extendible into first passage 3512. Member 3520 is pivotally located in a pivot member passage 3511 that communicates with first passage 3512.

Member 3520 is a generally inverted "V-shaped" member that is pivotable about a pivot point 3521 in pivot member passage 3511 between a first rod unlocking position and a first rod locking position to releasably secure rod 70 in first passage 3512. Member 3520 has a rod engaging surface 3524 (a first leg of the "V") that engages rod 70 and biases rod 70 against wall 3514. Rod engaging surface 3524 can have at least a slightly arcuate profile such that, as member 3520 is pivoted from the rod unlocking position to the rod locking position (as shown in FIG. 80), rod engaging surface 3524 "cups" rod 70 to provide a secure connection between connector 3500 and rod 70. Member 3520 also includes a cam surface 3530 as the remaining leg of the "V" that is acted upon to pivot member 3520.

Securing mechanism 3522 also includes a rotating portion in the form of a set screw 3540 that is adapted to engage cam surface 3530 of member 3520 such that member 3520 is pivoted about pivot pin 3521, pivoting rod engaging surface 3524 into engagement with first rod 70. Set screw 3540 is threadingly mounted in a threaded screw passage 3542 that is in communication with pivot member passage 3511. Set screw 3540 includes a first end 3544 having a receiver 3546, such as, for example, for an Allen wrench or a Torx® wrench, and an engagement end 3548 having a tapered tip 3550 such that, as set screw 3540 is screwed downwardly into screw passage 3542, tapered tip 3550 engages cam surface 3530 and pivots member 3520 into passage 3512 and into engagement with rod 70.

Yet another alternative embodiment of a cam lock top loading connector 3600 is shown in FIGS. 80-85. Connector 3600 is similar to connector 3100 with the exception of first connecting portion 3610, which differs from first connecting portion 3110 in connector 3100 as described below.

First connecting portion 3610 includes an open first passage 3612 defined by an arcuate wall 3614 that allows connector 3600 to be placed over a member, such as rod 70 (shown in FIGS. 82-85), in an existing construct to add on to the existing construct.

First connecting portion 3610 includes a securing mechanism 3622 having a locking portion in the form of a member 3620 that is rotatably extendible into first passage 3612. Member 3620 is rotatably located in a vertical passage 3611 that communicates with first passage 3612.

Figure 84:
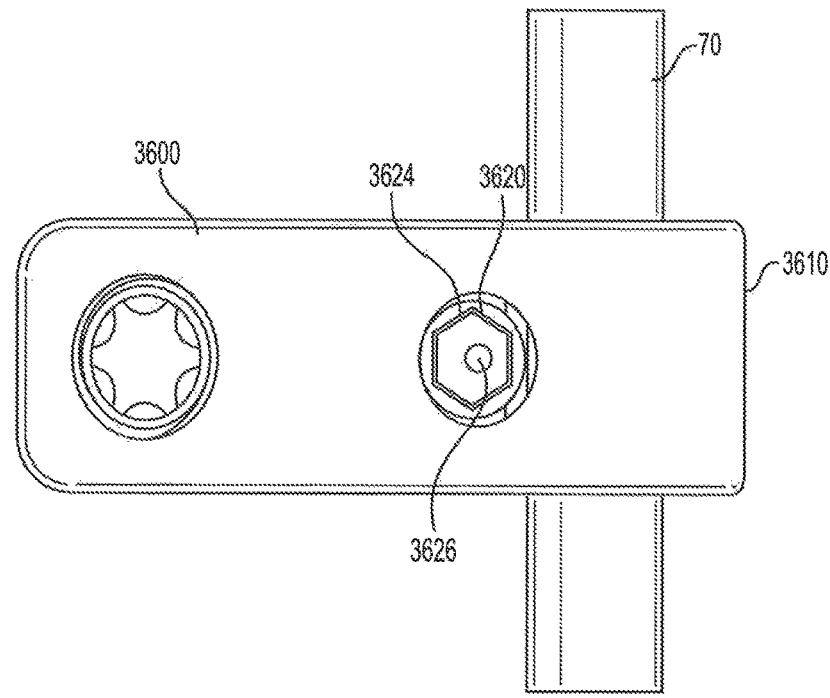
FIG. 84 is a top plan view of the connector shown in FIG. 81 connected to a rod, with the cam in the unlocking position.
Figure 85:
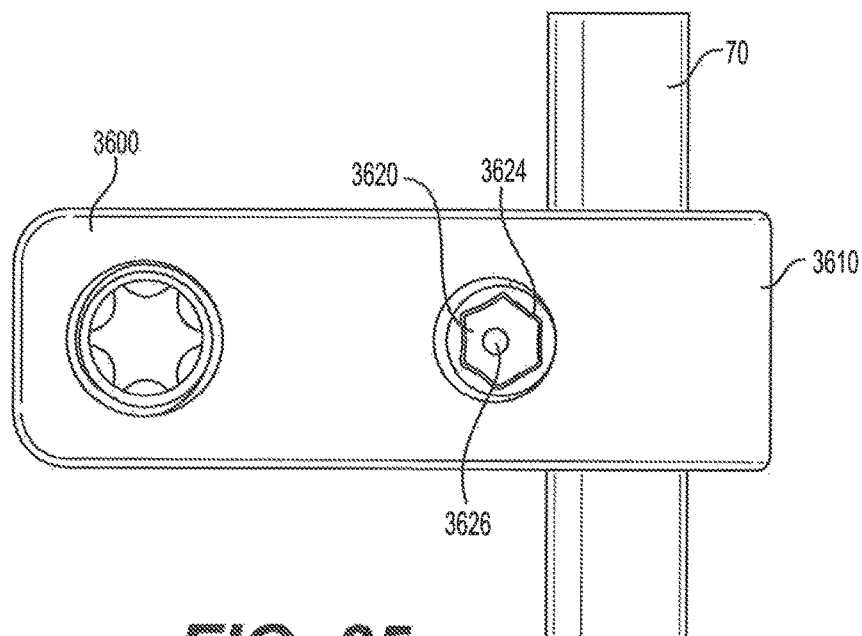
FIG. 85 is a top plan view of the connector shown in FIG. 81 connected to a rod, with the cam in the locking position.
Figure 86:
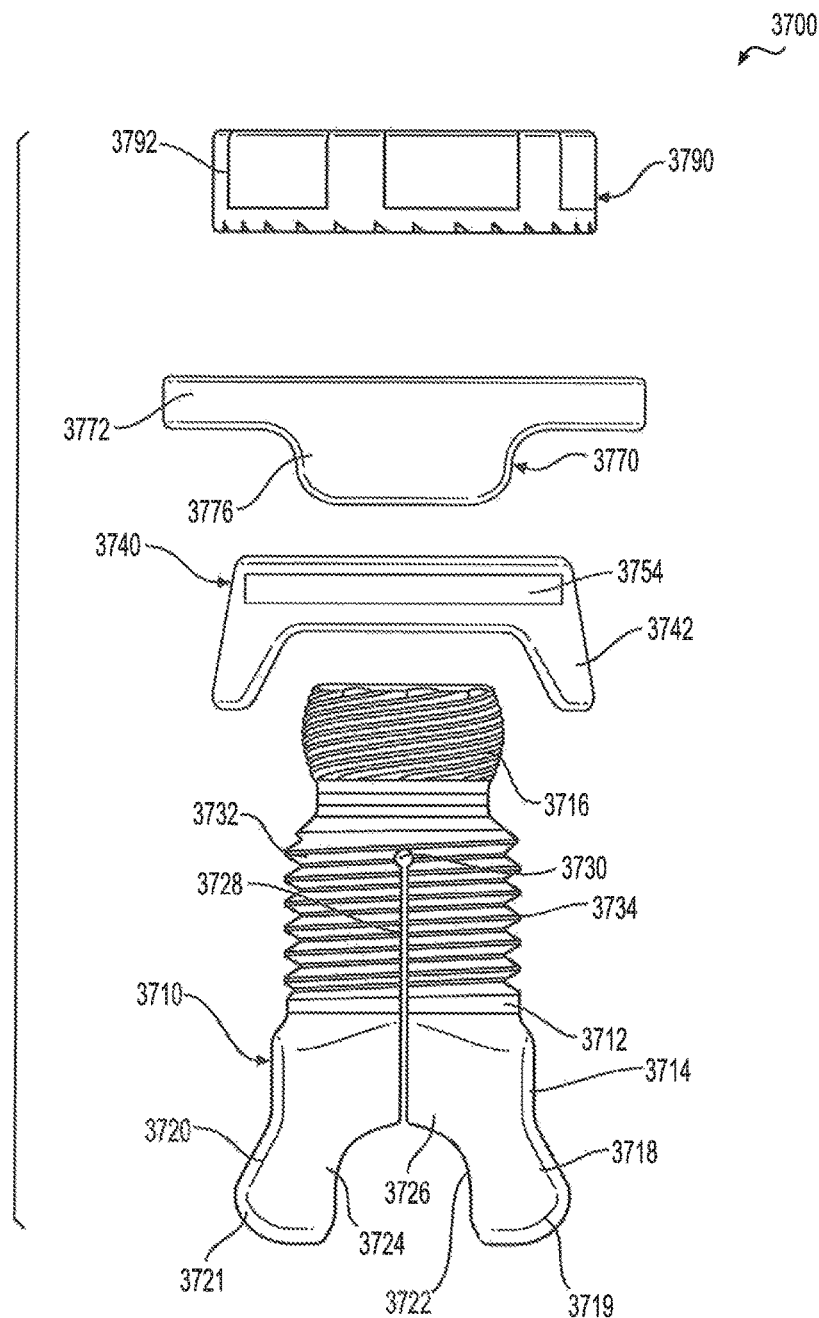
FIG. 86 is an exploded side elevational view of a top loading connector according to a thirty-seventh embodiment.
Figure 87:
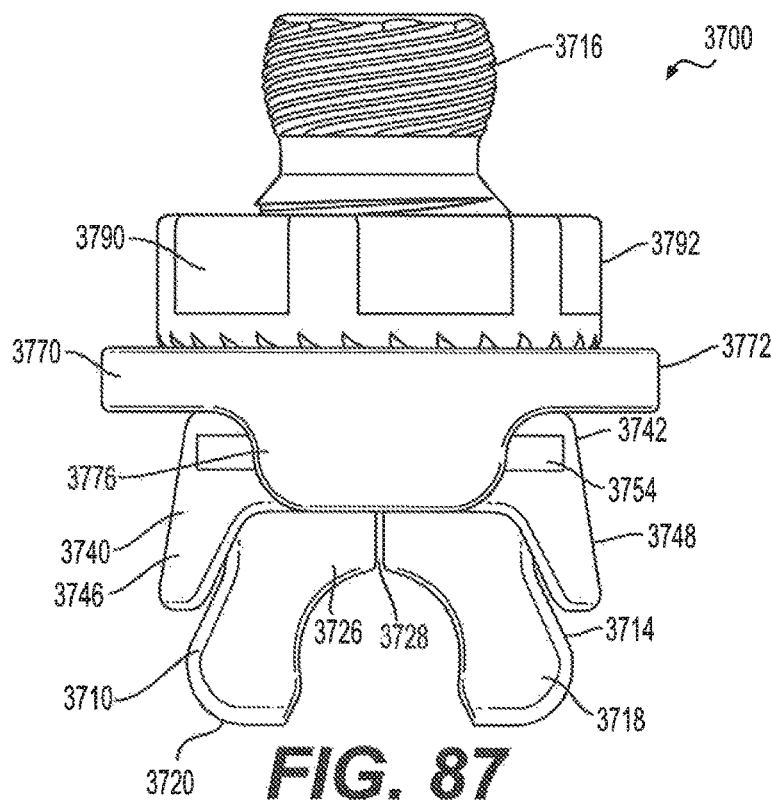
FIG. 87 is a side elevational view of the top loading connector shown in FIG. 86.

Member 3620 includes a round portion 3624 having an axis 3626 that is off-center of the axis of rotation of member 3620 as shown in FIGS. 84 and 85. Rotation of member 3620 to the position shown in FIGS. 82 and 84 causes round portion 3624 to rotate off center, allowing rod 70 to be untouched and unsecured within first passage 3612. Rotation of member 3620 to the position shown in FIGS. 83 and 85 causes round portion 3624 to rotate to the securing position, biasing rod 70 against wall 3614 of first passage 3612.

An exemplary top loading modular connector 3700 is shown in FIGS. 86-91. Connector 3700 includes a threaded shaft 3710, a clamp sleeve 3740 that slides over threaded shaft 3710, a clamp body 3770 that is fit over clamp sleeve 3740, and a locking nut 3790 that secures clamp sleeve 3740 and clamp body 3770 onto threaded shaft 3710.

Threaded shaft 3710 has an elongate body 3712 having a top loading clamping portion 3714 and a connection end 3716 on top of clamping portion 3714. Clamping portion 3714 includes a pair of legs 3718, 3720, each having an arcuate cutout 3722, 3724, respectively, that, when pressed together, form a generally semi-circular surface 3726. Each leg 3718, 3720 includes an outwardly flared portion 3719, 3721, respectively, that is engaged by clamp sleeve 3740 when clamp sleeve 3740 is compressed downwardly toward clamping portion 3714, such that flared portions 3719, 3721 are biased toward each other so that legs 3718, 3720 grip rod 70.

The diameter of surface 3726 is less than the diameter of rod 70. A flexure cut 3728 with a relief cut 3730 at a top end thereof allows clamping portion 3714 to open and clamp around rod 70. A central portion 3732 of threaded shaft 3710 has external threads 3734 that threadingly engage lock nut 3790.

Clamp sleeve 3740 has a generally annular body 3742 with a generally circular diametric opening 3744 that is larger than the diameter of central portion 3732 of threaded shaft 3710 such that clamp sleeve 3740 can be slid over central portion 3732. Clamp sleeve 3740 includes a pair of diametrically opposed clamp legs 3746, 3748 that extend downwardly from body 3742. Each leg 3746, 3748 has a tapered interior cutout 3750, 5752, respectively, that engages flared portions 3721, 3719, respectively, to bias flared portions 3719, 3721 toward each other to engage rod 70.

Body 3742 also includes an elongate detent 3754 on either side of body 3742 between legs 3746, 3748. Detents 3754 each receive a corresponding tang (not shown) on clamp body 3770 to releasably secure clamp body 3770 to clamp sleeve 3740 when locking nut 3790 is threaded onto threaded shaft 3710.

Clamp body 3770 has a generally annular body 3772 with a generally circular diametric opening 3774 that is larger than the diameter of central portion 3732 of threaded shaft 3710 such that clamp body 3770 can be slid over central portion 3732. Clamp body 3770 includes a pair of diametrically opposed tang lips 3776 (only one tang lip 3776 shown in FIG. 87) with a tang (not shown) that extends into a respective detent 3754 in clamp sleeve 3740 to secure clamp sleeve 3740 to clamp body 3770 and restrict rotation of clamp sleeve 3740 about threaded shaft 3710 when locking nut 3790 is threaded onto threaded shaft 3710.

Locking nut 3790 has a body 3792 and a central opening 3794 defined by internal threads 3796 that threadingly engage threads 3734 on threaded shaft 3710.

Figure 88:
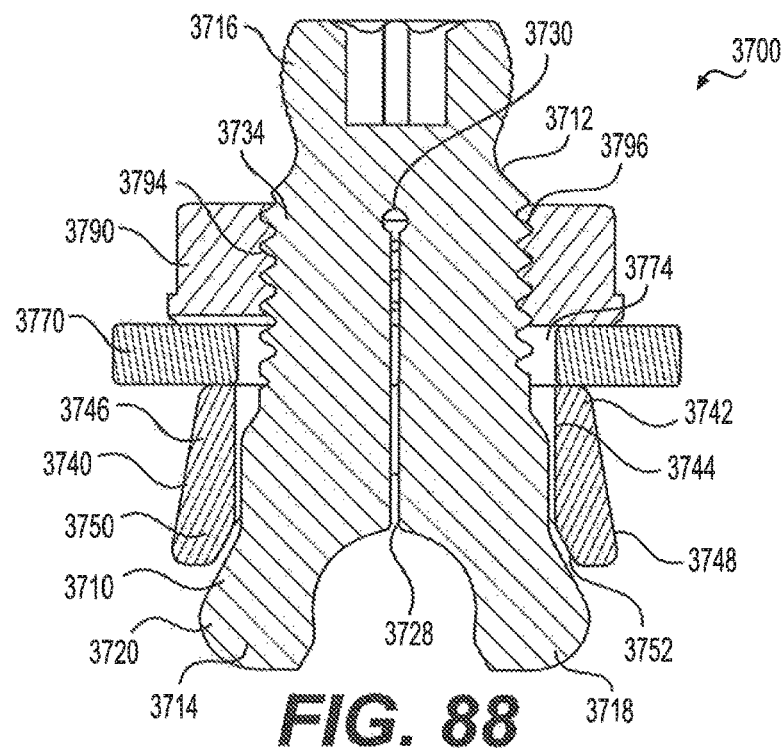
FIG. 88 is a sectional view of the top loading connector shown in FIG. 86.
Figure 89:
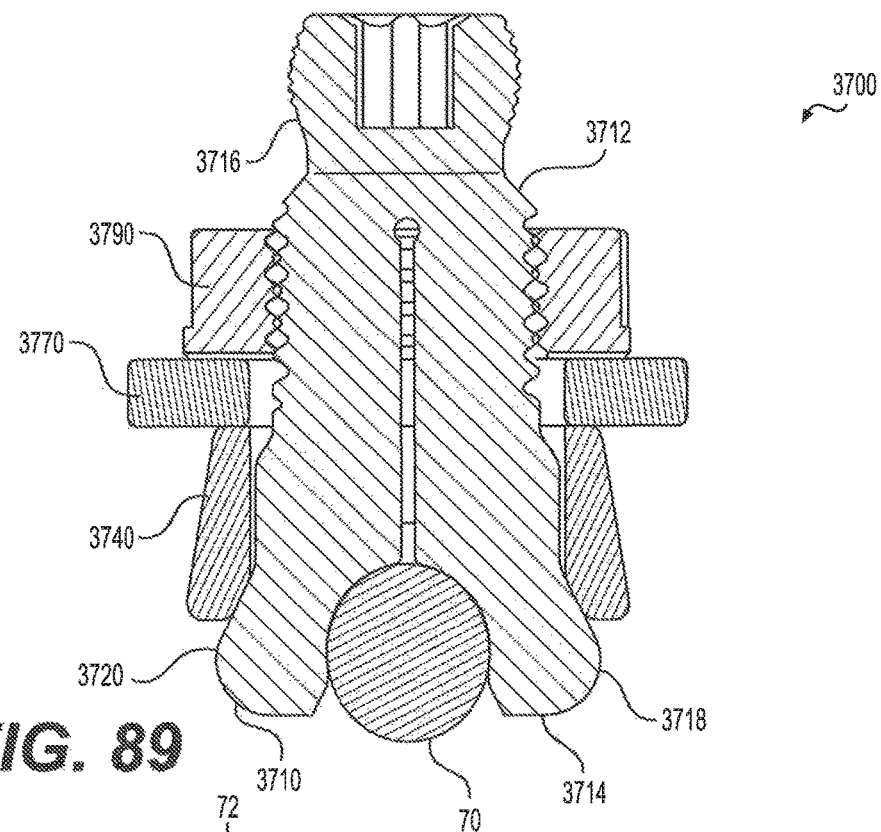
FIG. 89 is a sectional view of the top loading connector shown in FIG. 86, with the connector clamped onto a rod.

In a loading position, as shown in FIG. 88, clamp sleeve 3740 is free to move about clamping portion 3714 of threaded shaft 3710 to allow clamping portion 3714 to flex and accept rod 70. When locking nut 3790 is threaded downwardly onto threads 3734 to the position shown in FIG. 89, locking nut 3790 forces clamp body 3770 downward over clamp sleeve 3740, which in turn forces clamp sleeve 3740 downward along legs 3718, 3720 of threaded shaft 3710, biasing legs 3718, 3720 toward each other, and gripping rod 70.

Figure 90:
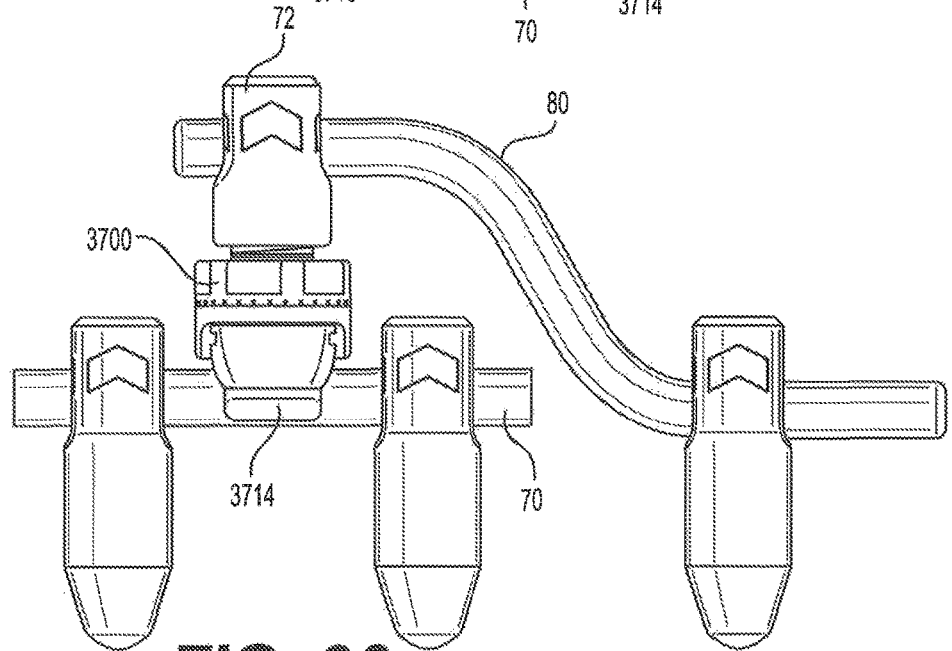
FIG. 90 is a side elevational view of the connector shown in FIG. 86 clamped onto a rod assembly with a screw tulip connector mounted on top of the connector.
Figure 91:
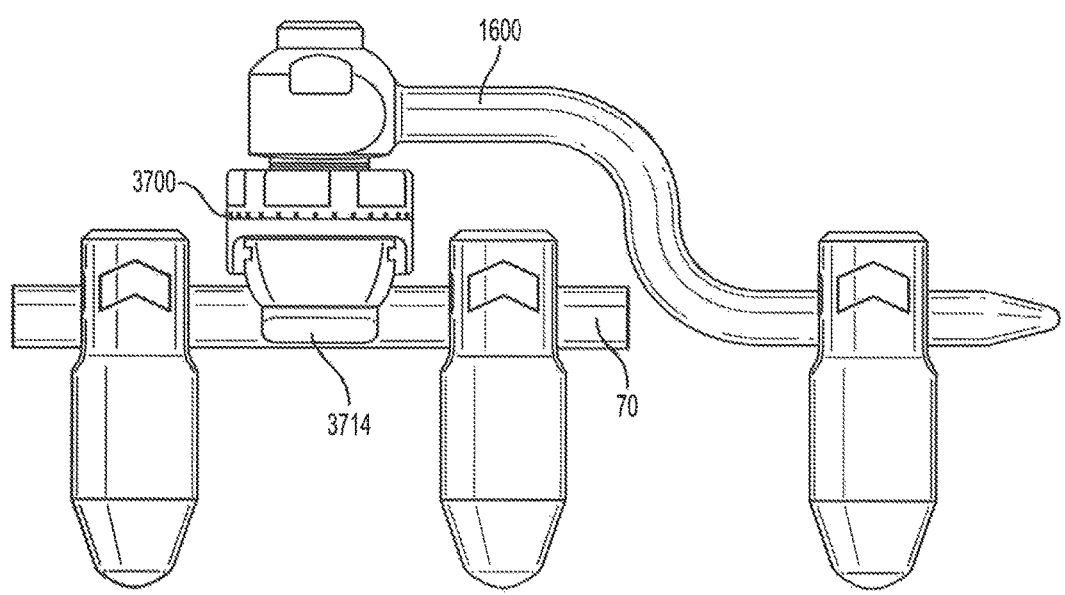
FIG. 91 is a side elevational view of the connector shown in FIG. 86 clamped onto a rod assembly with a connector mounted on top of the connector.
Figure 92:
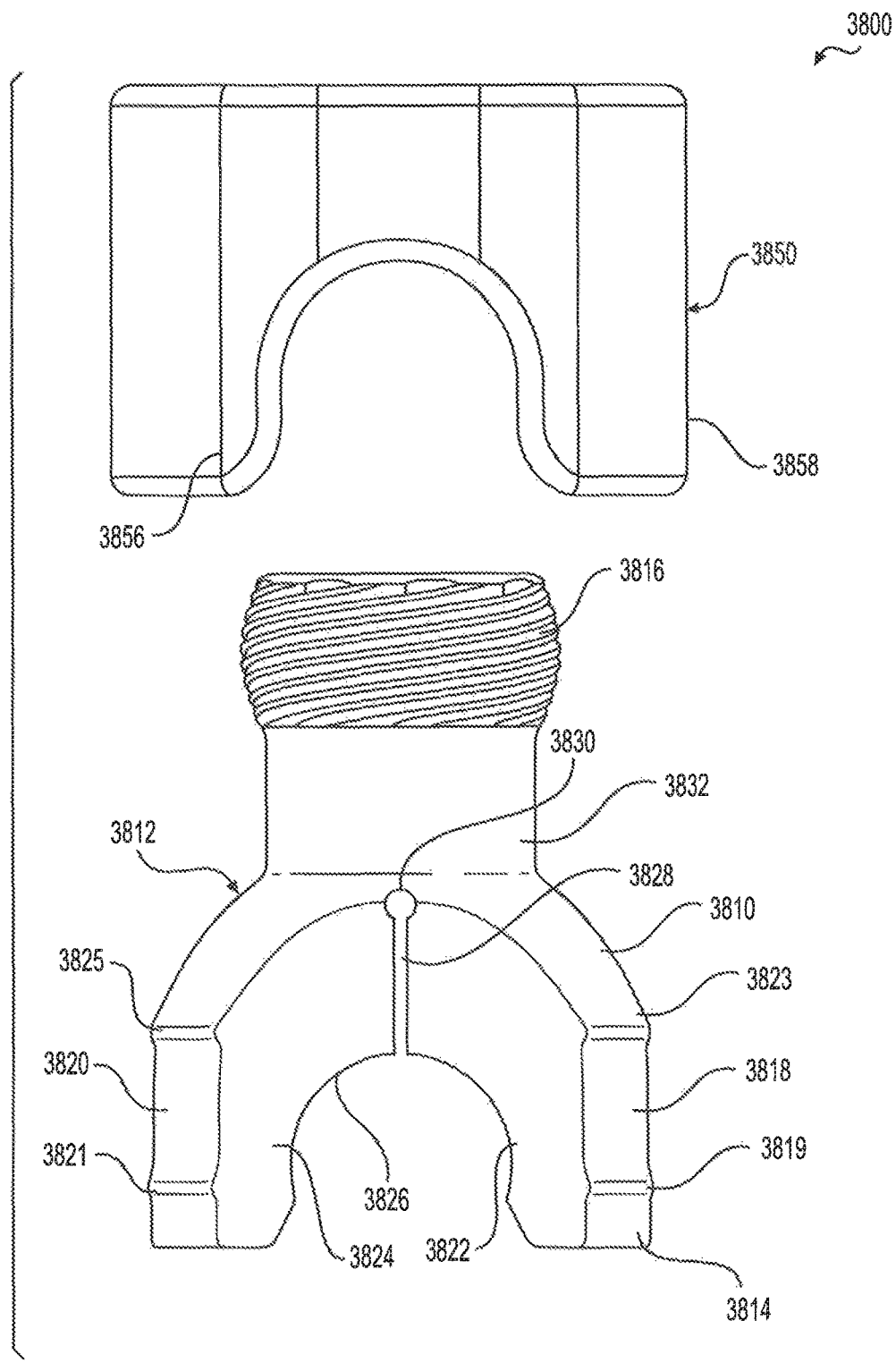
FIG. 92 is an exploded side elevational view of a top loading connector according to a thirty-eighth embodiment.
Figure 93:
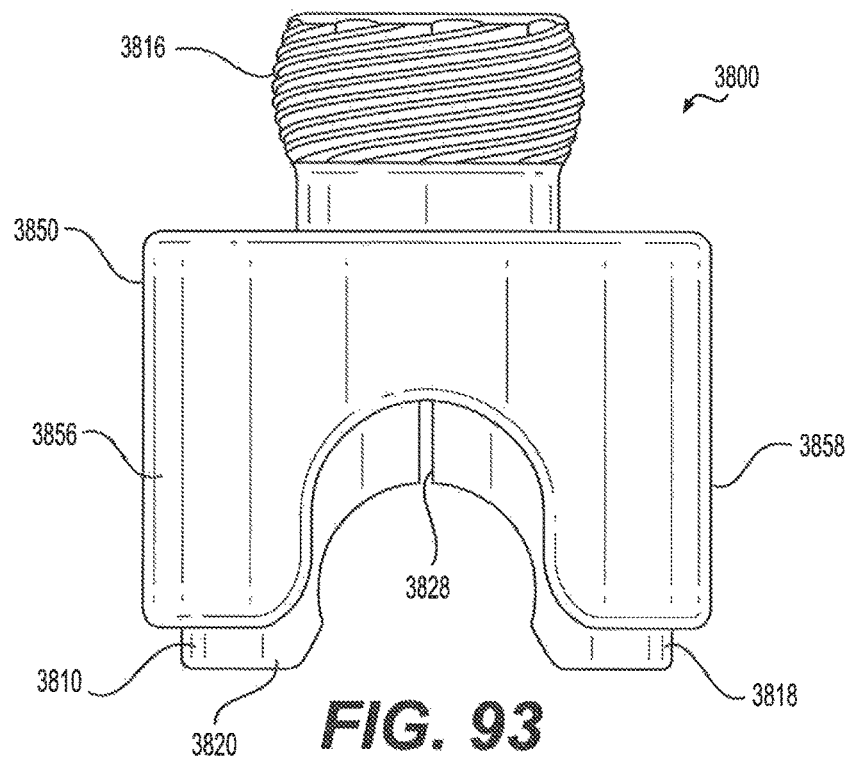
FIG. 93 is a side elevational view of the top loading connector shown in FIG. 92.

As shown in FIGS. 90 and 91, clamping portion 3714 can be attached to an existing rod 70 from above while connection end 3716 serves as the attachment point for a screw tulip 72 (shown in FIG. 90), a connector rod 1600 (shown in FIG. 91), or other suitable construct in order to extend fixation to an adjacent level.

Another exemplary top loading modular connector 3800 is shown in FIGS. 92-97. Connector 3800 includes a clamp shaft 3810 and an outer sleeve 3750 that slides over clamp shaft 3810.

Clamp shaft 3810 has an elongate body 3812 having a top loading clamping portion 3814 and a connection end 3816 on top of clamping portion 3814. Clamping portion 3814 includes a pair of legs 3818, 3820, each having an arcuate cutout 3822, 3824, respectively, that, when pressed together, form a generally semi-circular surface 3826. Each leg 3818, 3820 is flared outwardly from a central portion 3832 of clamp shaft 3810 with a generally convex surface. Central portion 3832 of clamp shaft 3810 has a first diameter, smaller than the diameter of clamping portion 3814.

Each leg 3818, 3820 also includes an outwardly flared lower nub 3819, 3821, respectively, that is engaged by outer sleeve 3850 when outer sleeve 3850 is compressed downwardly toward clamping portion 3814, such that flared lower nubs 3819, 3821 grip outer sleeve 3850 and so that legs 3818, 3820 are biased toward each other, resulting in legs 3818, 3820 gripping rod 70. Also, each leg 3818, 3820 also includes an outwardly flared upper nub 3823, 3825, The diameter of surface 3826 is less than the diameter of rod 70. A flexure cut 3828 with a relief cut 3830 at a top end thereof allows clamping portion 3814 to open and clamp around rod 70.

Clamp shaft 3850 has a generally annular body 3852 with a generally circular diametric lower opening 3854 that is slightly smaller than the diameter of clamping portion 3814 at the lower end of legs 3818, 3820 and a generally circular diametric upper opening 3855 that is larger than the diameter of connection end 3816 such that clamp shaft 3850 can be slid over connection end 3816.

Clamp shaft 3850 includes a pair of diametrically opposed shaft legs 3856, 3858 that extend downwardly from body 3742. Each leg 3856, 3858 has a tapered interior protrusion 3860, 5862, respectively, that engages lower nubs 3819, 3821 respectively, to bias legs 3818, 3820 toward each other to engage rod 70. Upper nubs 3823, 3825 keep outer sleeve 3850 from easily being pulled upwardly off clamp shaft 3810.

Figure 94:
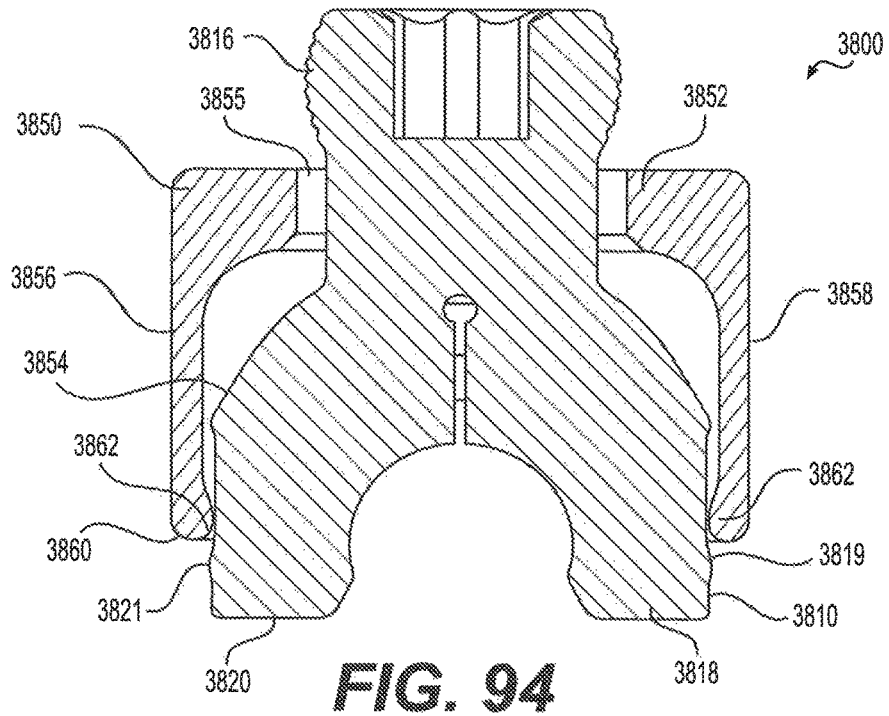
FIG. 94 is a sectional view of the top loading connector shown in FIG. 92.
Figure 95:
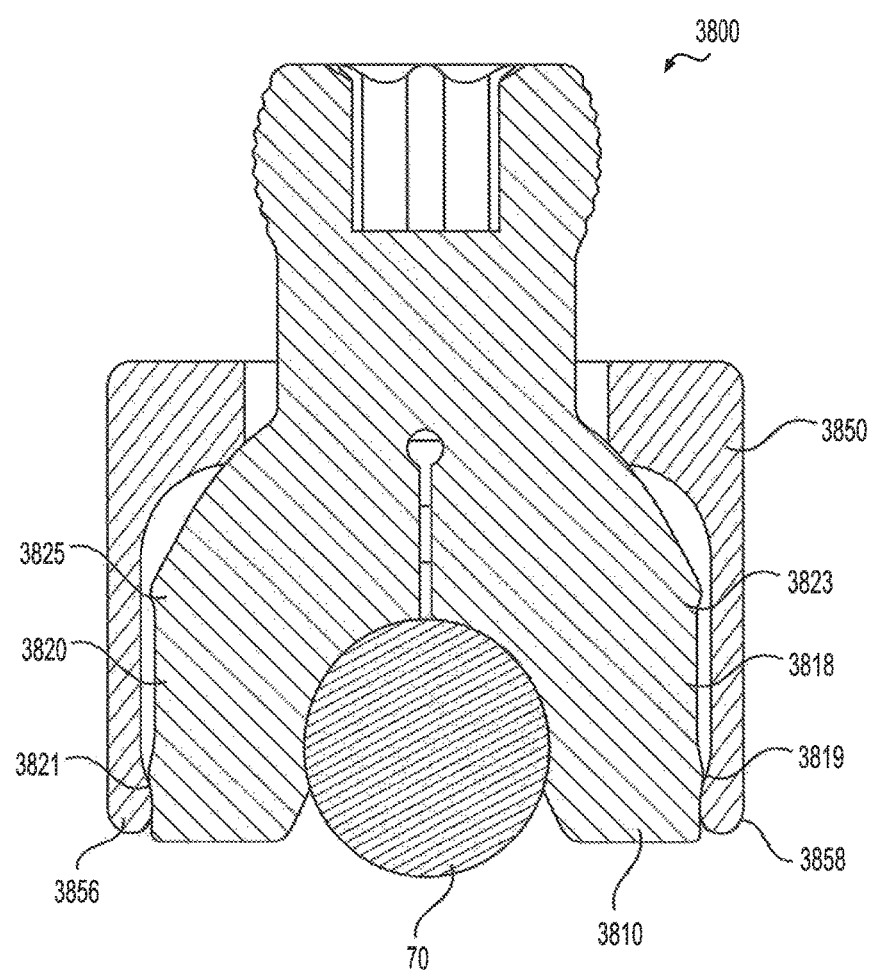
FIG. 95 is a sectional view of the top loading connector shown in FIG. 92, with the connector clamped onto a rod.

In a loading position, as shown in FIG. 94, outer sleeve 3850 is free to move about clamp shaft 3810 to allow clamping portion 3814 to flex and accept rod 70. When outer sleeve 3850 is advanced downwardly over lower nubs 3819, 3821 to the position shown in FIG. 95, shaft legs 3856, 3858 bias legs 3818, 3820 toward each other, and gripping rod 70.

Figure 96:
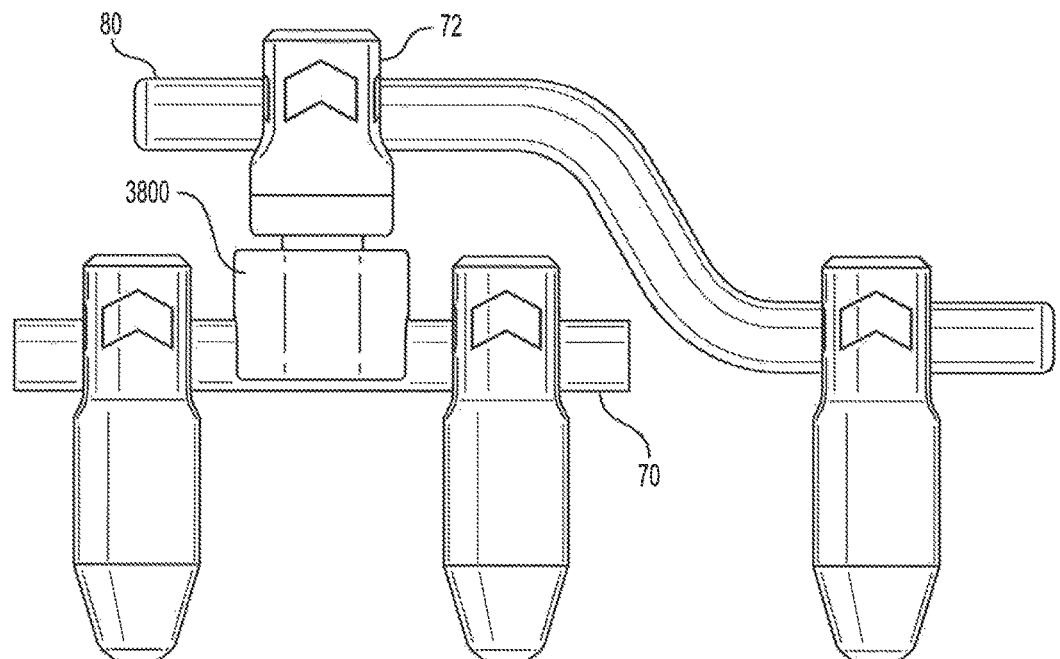
FIG. 96 is a side elevational view of the connector shown in FIG. 92 clamped onto a rod assembly with a screw tulip connector mounted on top of the connector.
Figure 97:
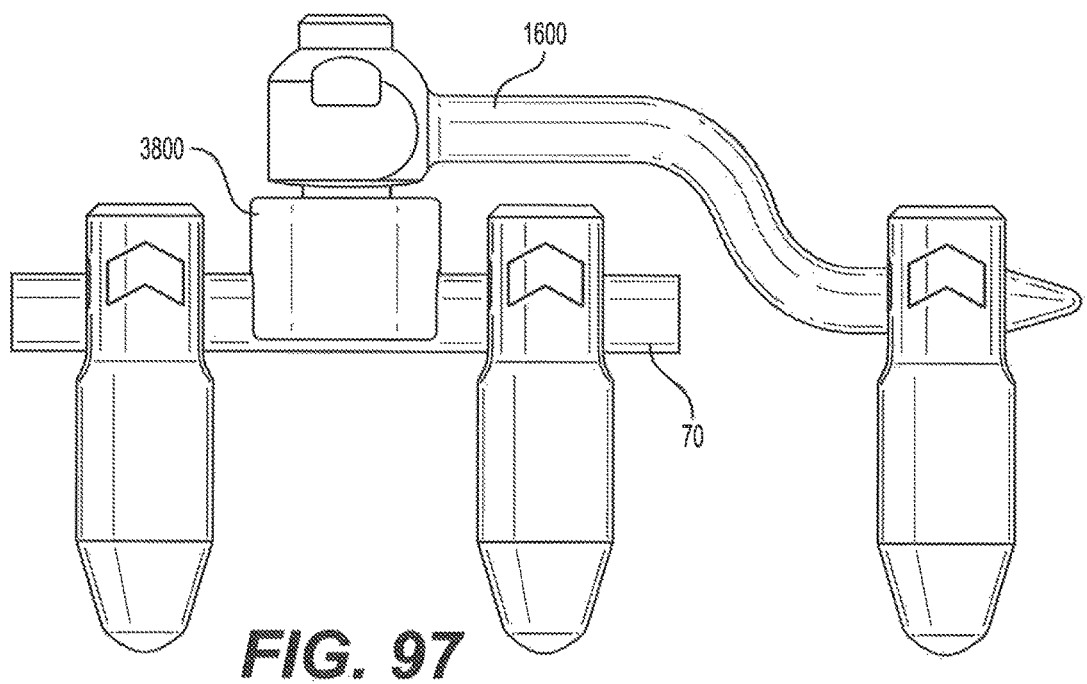
FIG. 97 is a side elevational view of the connector shown in FIG. 92 clamped onto a rod assembly with a connector mounted on top of the connector.

As shown in FIGS. 96 and 97, clamping portion 3814 is attached to an existing rod 70 from above while connection end 3816 serves as the attachment point for a screw tulip 72 (shown in FIG. 96), a connector rod 1600 (shown in FIG. 97), or other suitable construct, in order to extend fixation to an adjacent level.

Turning now to FIGS. 98A-98G, a top loading connector 3900 according to yet another embodiment is shown. Top loading connector 3900 is similar to the top loading connector 3100 shown in FIGS. 73 and 74 except that a clamping mechanism has been added to secure the rod 70 therein.

Connector 3900 is a top loading connector having a closed portion. The connector 3900 has a body 3902 having two clamping portions that are laterally offset from each other. A first clamping portion 3910 configured for attaching to a first spinal rod 50, 70 from above, and a second clamping portion 3950 for attaching to a second spinal rod 50, 70 through a closed passage.

Figure 98A:
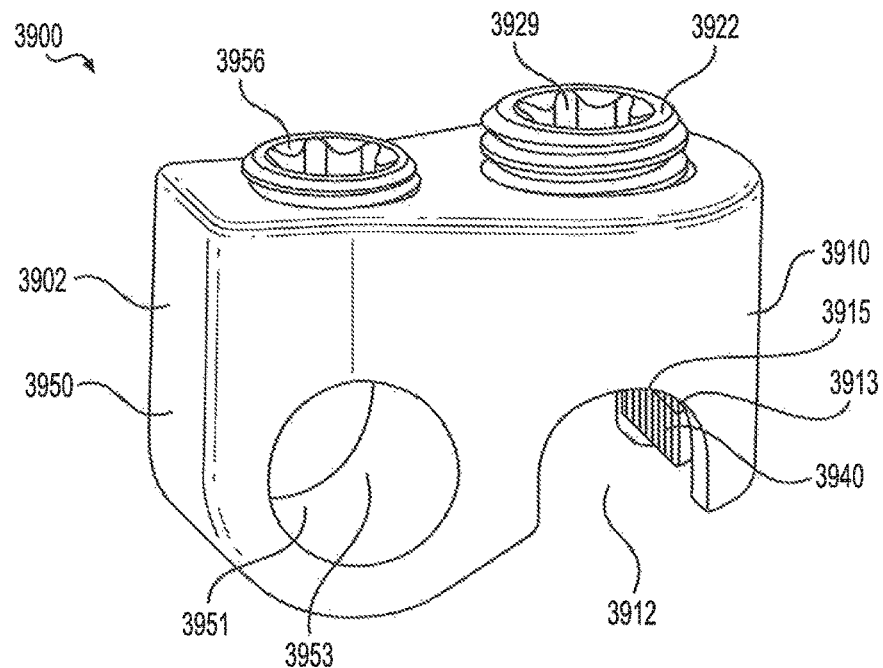
FIGS. 98A-98G depict a closed top loading connector according to yet another embodiment.
Figure 98B:
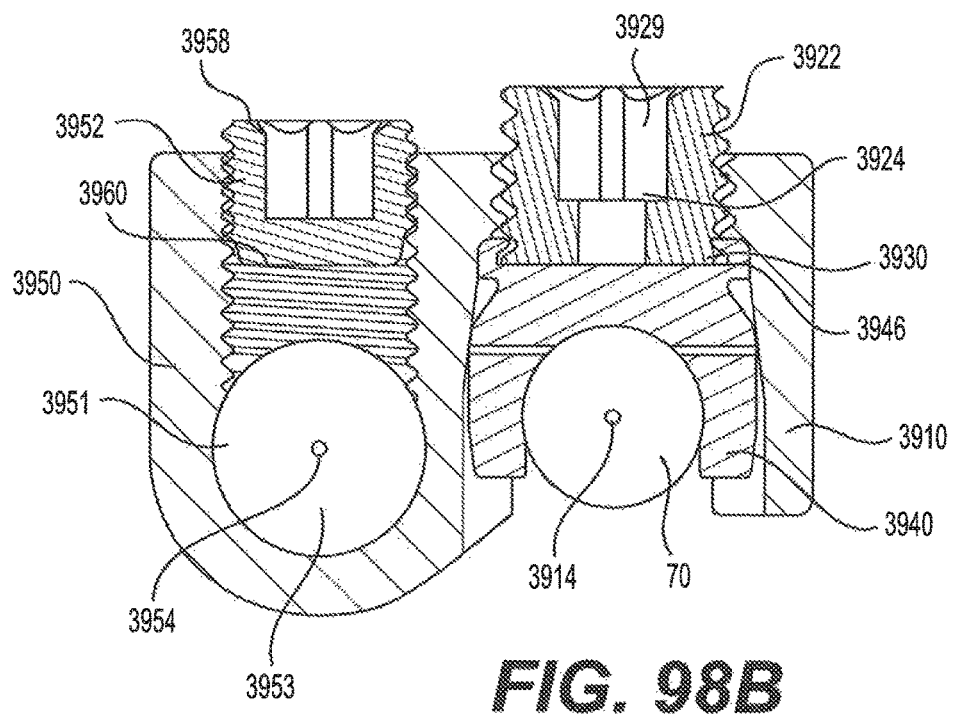
Figure 98C:
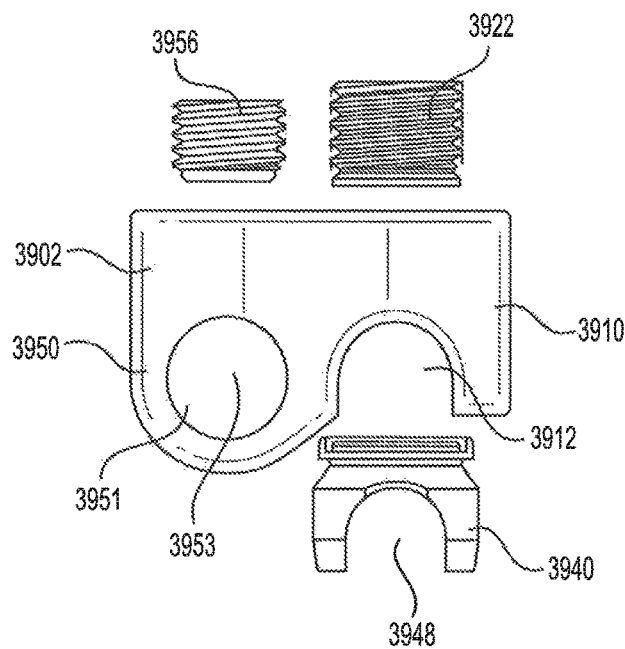
Figure 98D:
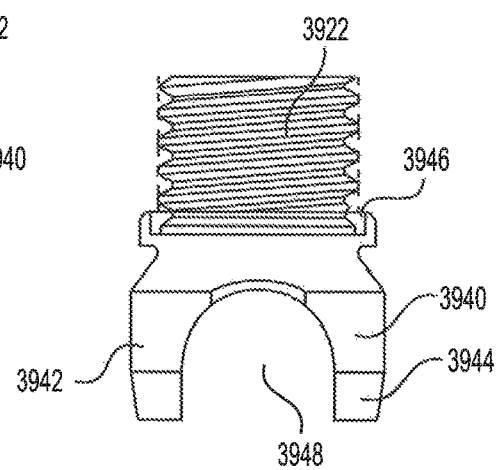
Figure 98E:
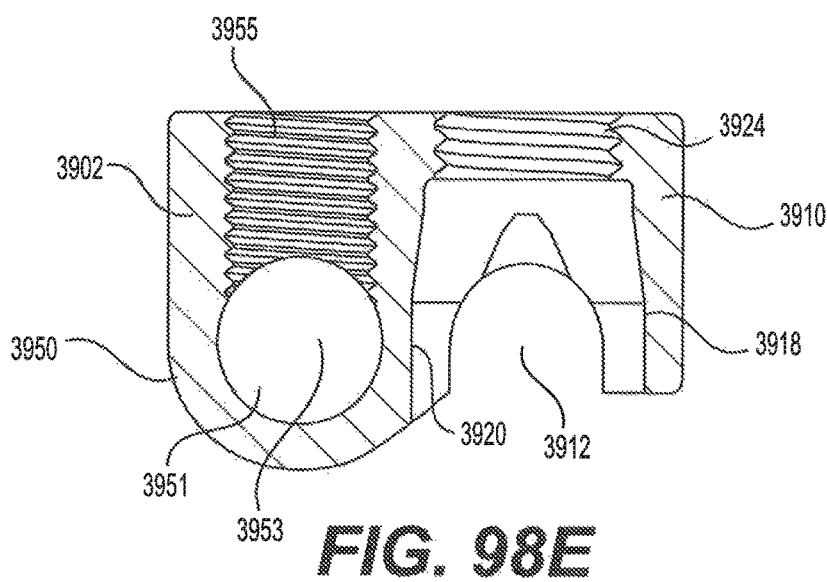
Figure 98F:
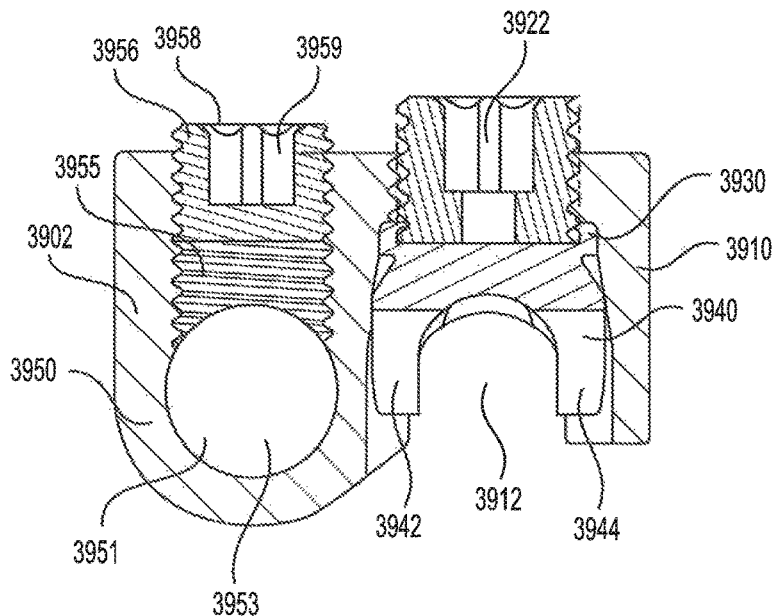

The first clamping portion 3910 has a first axial passage 3912 having a first longitudinal axis 3914 extending therethrough. Referring to FIG. 98B, axis 3914 extends perpendicularly outwardly from the plane of the paper of the Figure. First passage 3912 is sized to allow a first rod, such as rod 50 or 70, to be inserted thereinto. First passage 3912 may be generally U-shaped and has a closed top portion 3913 that has a generally arcuate top wall 3915. As best seen in FIG. 98E, opening 3912 is defined by generally opposing sidewalls 3918, 3920. The opposing sidewalls 3918, 3920 may be include one or more parallel and/or angled surfaces configured to receive a portion of a first securing mechanism 3922.

The first securing mechanism 3922 includes a locking set screw 3926 and a clamp 3940. Clamp 3940 includes a pair of legs 3942, 3944. The clamping legs 3942, 3944 are configured to receive a portion of the rod 50, 70 therein. The clamping legs 3942, 3944 may each have an arcuate cutout, respectively, that generally define a semi-circular surface. Inner surfaces on the opposing legs 3942, 3944 of the clamp 3940 may be textured, for example, to enhance the connection between the first rod 50, 70 and the clamp 3940. The locking set screw 3926 is engaged with an upper portion of the clamp 3940. For example, the engagement end 3930 of the locking set screw 3926 may include an annular protrusion configured to be received in a corresponding recess 3946 in the clamp 3940. The locking set screw 3926 may be free to rotate relative to the clamp 3940.

The first securing mechanism 3922 is rotatably connected to first clamping portion 3910 to releasably secure first rod 50 or 70 in first passage 3912. The set screw 3926 includes a threaded exterior that threadingly engages threaded through-hole 3924. One end of set screw 3926 includes a receiver opening 3929, such as, for example, for an Allen wrench or a Torx® wrench, and the engagement end 3930 that connects to the clamp 3940. The threaded set screw 3926 is able to rotate independently from the clamp 3940. The threaded set screw 3926 threads into the main body 3902 of the connector 3900 from the bottom, allowing the clamp 3940 to translate vertically within the main body 3902. A cutout in the main body 3902, forming opposing sidewalls 3918, 3920, is angled such that the width of the cutout decreases from the bottom of the main body upward. Therefore, when the clamp 3940 translates upward, the wall of the cutout in the main body 3902 contacts the outer edges of the clamp 3940.

Figure 98G:
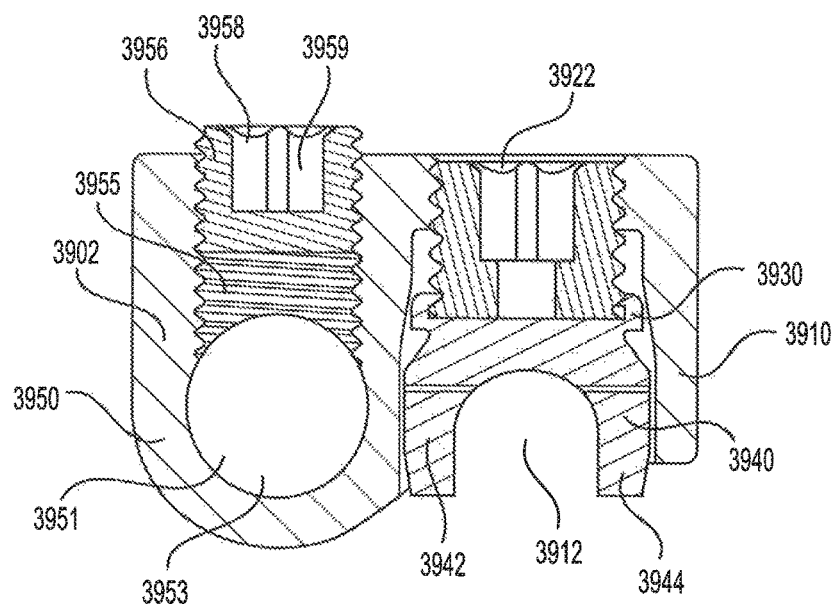

FIG. 98G shows the clamp 3940 in an unlocked position. The configuration of the body of the clamp 3940 allows the clamp 3940 to plastically deform, decreasing the size of the opening 3948 accepting the spinal rod 50, 70. If desired, a relief cut may further be provided to enhance the deformation of the clamp. As the set screw 3926 is threaded upward, to the locked position shown in FIG. 98F, legs 3942, 3944 are biased toward each other, resulting in legs 3942, 3944 gripping rod 50, 70 therebetween. Thus, the top-loading portion 3910 of the connector 3900 is able to reversibly attach to a spinal rod 50, 70 from above by being placed over the rod 50, 70 in the unlocked position (FIG. 98G) and subsequently threading the threaded set screw 3926 upward into the locked position (FIG. 98F) in order to close the clamp 3940 around the spinal rod 50, 70.

The second clamping portion 3950 is a closed connector having a second passage 3951 that has a second longitudinal axis 3954 extending therethrough. Second passage 3951 comprises a generally circular axial passage, or through-opening 3953. Second longitudinal axis 3954 may be substantially parallel or may be axially offset relative to first longitudinal axis 3914. The second passage 3951 is sized and dimensioned to allow the second rod, 50, 70, to be inserted thereinto along second longitudinal axis 3954.

Second clamping portion 3950 includes a second securing mechanism 3952 that is adapted to releasably secure second rod 50, 70 in second passage 3953. Second securing mechanism 3950 includes a threaded through-hole 3955 and a second set screw 3956 that is rotatably inserted into through-hole 3955. Set screw 3956 includes a threaded exterior that threadingly engages threaded through-hole 3955. First end 3958 of set screw 3956 also includes a receiver opening 3959, such as, for example, for an Allen wrench or a Torx® wrench, and an engagement end 3960 that extends into second passage 3951 to bias the rod 50, 70 against the wall of through-opening 3953 to secure rod 50, 70 within the connector 3900.

Connector 3900 can be used, for example, in a revision procedure to add a new construct to an existing construct or may be used a first or single procedure. By way of example only, opening 3912 can be inserted over first rod 70 in an existing construct. First connecting portion 3910 can be secured to first rod 70 by rotating securing mechanism 3922 and advancing clamp 3940 to the locked position to secure first rod 70 to first connecting portion 3910. Second rod 50 can be inserted through closed through-opening 3953 and secured by set screw 3956, thereby securing new spinal construct to the existing spinal construct.

Figure 99:
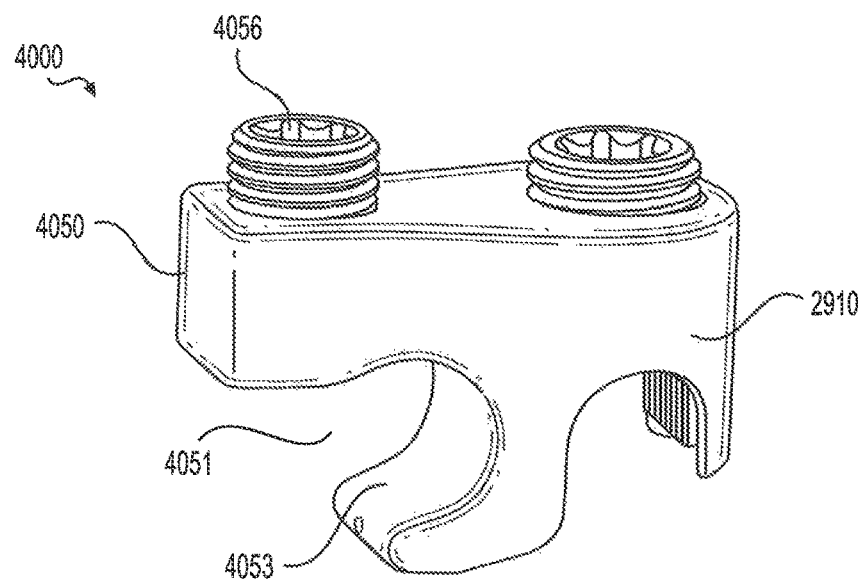
FIG. 99 provides a top loading lateral connector according to yet another embodiment.
Figure 100:
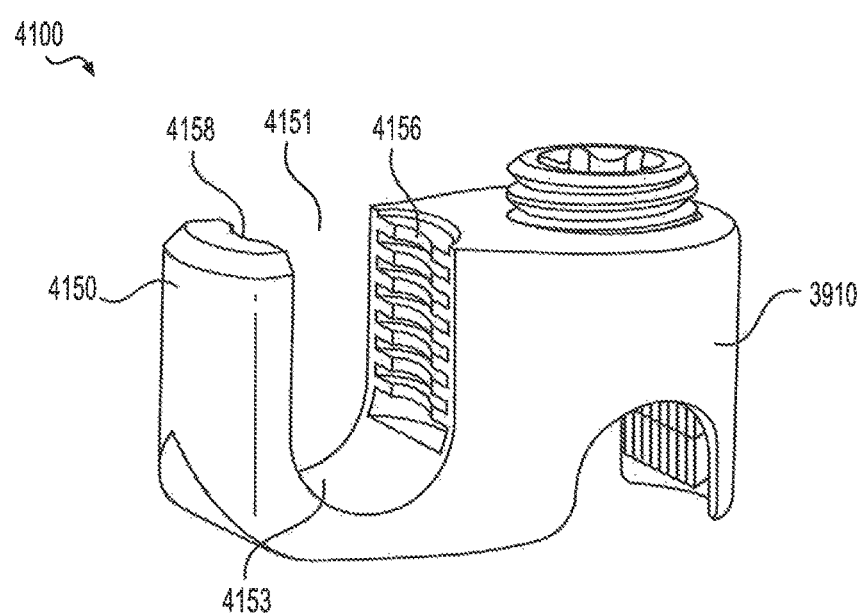
FIG. 100 is a top loading connector with a tulip connection according to yet another embodiment.

An alternative embodiment of a connector 4000 is shown in FIG. 99. Connector 4000 is similar to connector 3900 including first clamping portion 3910 with the set screw 3926 and clamp 3940. Connector 4000 differs from second connecting portion 3950 in that the closed opening 3953 is replaced with a lateral side opening 4051. This lateral opening 4051 is similar to the embodiment described and shown in FIG. 75.

Instead of generally circular passage 3951, in connector 4000, the second connector portion 4050 has second passage 4051 with an opening defined by a generally U-shaped wall 4053 that allows connector 4000 to be inserted over second rod 50, 70 (not shown) by a lateral connection. A set screw 4959 is threaded into a corresponding threaded opening to secure the rod 50, 70 in the passage 4051 and against the wall 4053. Also, connector 4000 can be reversed such that second connecting portion 4050 can be secured to existing rod 50, 70 and first connecting portion 3910 can be secured to a new construct, such as rod 50, 70.

Another alternative embodiment of a connector 4100 is shown in FIG. 4100. Connector 4100 is similar to connector 3900 including first clamping portion 3910 with the set screw 3926 and clamp 3940. Connector 4100 differs from second connecting portion 3950 in that the closed opening 3953 is replaced with a second connection portion 4150 having a "tulip style" connection. This is similar to the tulip-style embodiment described and shown in FIG. 76.

Second connecting portion 4150 has a second passage with a generally U-shaped opening 4151 that opens at the top of second connecting portion 4150 and has a closed bottom wall 4153 that is arcuate in shape. Opening 4154 is defined by bottom wall 4153 and opposing generally planar side walls 4156, 4158 that each includes threaded portions, respectively. After a rod 50, 70 is positioned within the opening 4151, these threads are used to receive a securing member, such as set screw 4056 (shown in FIG. 99). The set screw 4056 is threaded downwardly until the rod 50, 70 is secured against the bottom wall 4153.

Turning now to FIGS. 101A-101F, a top loading connector 4200 according to yet other embodiments is shown. Top loading connector 4200 is similar to the top loading connector 3900 shown in FIGS. 98A-98G except that the closed portion has been replaced with a modular connection point (for example, as previously provided in connectors 500 and 1300).

As best seen in FIG. 101A, connector 4200 is a top loading connector having a modular portion 4250. The connector 4200 has a body 4202 with a first integrated clamping portion 4210 and a second modular portion 4250 laterally offset from one another. The first clamping portion 4210 is configured for attaching to a first spinal rod 50, 70 from above, and the second modular portion 4250 is configured to receive a tulip 72 (FIG. 101E) for attaching to a second spinal rod 50, 70, to receive an integrated rod 1200 (FIG. 101F), or to receive another modular component.

The first clamping portion 4210 has a first axial passage 4212 having a first longitudinal axis 4214 extending therethrough. Referring to FIG. 101C, axis 4214 extends perpendicularly outwardly from the plane of the paper of the Figure. First passage 4212 is sized to allow a first rod, such as rod 50 or 70, to be inserted thereinto. First passage 4212 may be generally U-shaped and has a closed top portion 4213 that has a generally arcuate top wall 4215. As best seen in FIG. 101A, opening 4212 is defined by generally opposing sidewalls 4218, 4220. The opposing sidewalls 4218, 4220 may include one or more parallel and/or angled surfaces configured to receive a portion of a first securing mechanism 4222.

The first securing mechanism 4222 includes a locking set screw 4226 and a clamp 4240. Clamp 4240 includes a pair of legs 4242, 4244. The clamping legs 4242, 4244 are configured to receive a portion of the rod 50, 70 therein. The clamping legs 4242, 4244 may each have an arcuate cutout, respectively, that generally define a semi-circular surface. Inner surfaces on the opposing legs 4242, 4244 of the clamp 4240 may be textured, for example, to enhance the connection between the first rod 50, 70 and the clamp 4240. The locking set screw 4226 is engaged with an upper portion of the clamp 4240. For example, the engagement end 4230 of the locking set screw 4226 may include an annular protrusion configured to be received in a corresponding recess 4246 in the clamp 4240. The annular protrusion may be substantially smooth and substantially cylindrical in shape, for example, having a diameter greater than the remainder of the locking set screw 4226. The locking set screw 4226 may be free to rotate relative to the clamp 4240.

The first securing mechanism 4222 is rotatably connected to first clamping portion 4210 to releasably secure first rod 50 or 70 in first passage 4212. The upper portion of set screw 4226 includes a threaded exterior that threadingly engages threaded through-hole 4224. One end of set screw 4226 includes a receiver opening 4229, such as, for example, of a shape configured to receive an Allen wrench or a Torx® wrench, and the other end of the set screw 4226 includes engagement end 4230 that connects to the clamp 4240. The threaded set screw 4226 is able to rotate independently from the clamp 4240. The threaded set screw 4226 threads into the main body 4202 of the connector 4200, allowing the clamp 4240 to translate vertically within the main body 4202. A cutout in the main body 4202, forming opposing sidewalls 4218, 4220, may be angled such that the width of the cutout decreases from the bottom of the main body upward. Therefore, when the clamp 4240 translates upward, the wall of the cutout in the main body 4202 contacts the outer edges of the clamp 4240.

FIG. 101B shows the clamp 4240 in an unlocked position. The configuration of the body of the clamp 4240 allows the clamp 4240 to plastically deform, decreasing the size of the opening 4248 accepting the spinal rod 50, 70. As shown, one or more relief cuts 4245 may be provided to enhance the deformation of the clamp 4240. The relief cuts 4245 may be straight or angled in the clamp body 4240. As the set screw 4226 is threaded upward, to the locked position shown in FIG. 101C, legs 4242, 4244 are biased toward each other, resulting in legs 4242, 4244 gripping rod 50, 70 therebetween. Thus, the top-loading portion 4210 of the connector 4200 is able to reversibly attach to a spinal rod 50, 70 from above by being placed over the rod 50, 70 in the unlocked position (FIG. 101B) and subsequently threading the threaded set screw 4226 upward into the locked position (FIG. 101C) in order to close the clamp 4240 around the spinal rod 50, 70.

The second clamping portion 4250 is a modular connector. The modular clamping portion 4250 may be in the form of a post 4252 extending from the body 4202 of the connector 4200. The post 4252 may extend generally orthogonally or perpendicularly from the portion of the body 4202 connecting the first clamping portion 4210 to the second clamping portion 4250. It is also envisioned that the post 4252 may extend from the first clamping portion 4210 at any other suitable angle or direction. The post 4252 or connection point may have a partially spherical outer surface with a generally flat top surface, for example. The post 4252 may having one or more recesses or openings 4254 therein configured to be engaged by an instrument (not shown). The spherical outer surface may be threaded, for example, to enhance engagement with the corresponding opening in the headed rod 1200 or tulip assembly 72.

Figure 101D:
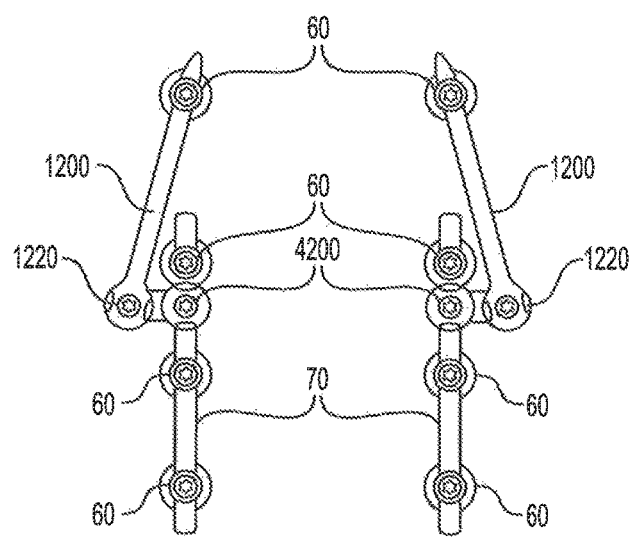
Figure 101E:
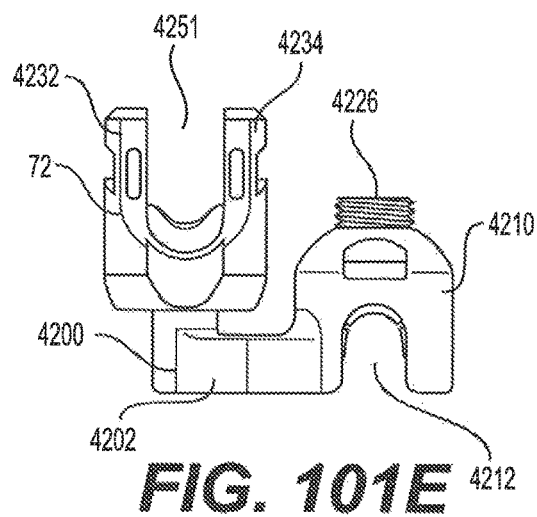

As best seen in FIG. 101E, the modular post 4250 of connector 4200 may be configured to receive a tulip assembly 72. The tulip 72 may include a first extension 4232 separated from a second extension 4234 defining a passage 4251 therebetween that has a second longitudinal axis extending therethrough. Passage 4251 may comprise a generally U-shaped passage or through-opening. The tulip 72 may be configured to receive a second rod 50, 70 (not shown) along the second longitudinal axis. The second passage 4251 is sized and dimensioned to allow the second rod 50, 70 to be bottom loaded into the tulip 72. The tulip 72 is configured to rotate or articulate about the post 4250 such that the second rod 50, 70 may be aligned substantially parallel, angled, or axially offset relative to the first longitudinal axis 4214 of the first rod 50, 70. Once the desired orientation of the second rod 50, 70 relative to the first rod 50, 70 is achieved, a locking cap (not shown) may be positioned to secure the rod 50, 70 to the tulip 72 and secure the position of the tulip 72 relative to the connector 4200.

Figure 101F:
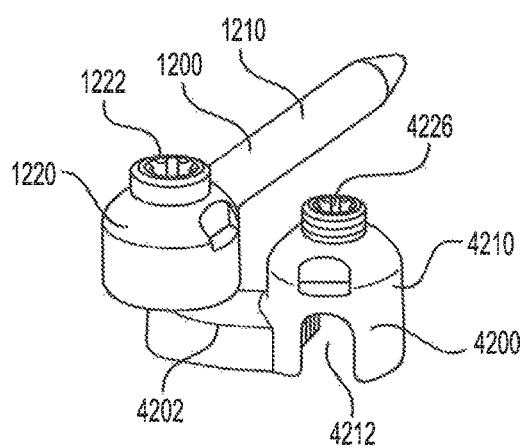

Turning now to FIG. 101F, the modular post 4250 of the connector 4200 is further configured to receive a headed rod 1200. The headed rod 1200 includes a rod portion 1210 with modular connection point 1220 at a first end and terminating at a second free end. Connection point 1220 has an opening sized and dimensioned to receive the modular connector post 4250 and one or more clamping elements positioned in the connection point 1220 are configured to retain the post 4250 of the first clamping portion 4210 within the connection point 1220. For example, the headed rod 1200 may include one or more of the connectors described in U.S. Publication No. 2016/0030091, which is incorporated by reference herein in its entirety for all purposes. The connection point 1220 may include a threaded connector, such as, for example, a fastener or set screw 1222 rotatably connected to the headed rod 1200 to secure rod 1210 to connector 4210. The headed rod 1200 is configured to rotate or articulate about the post 4250 such that the integrated rod 1210 may be aligned substantially parallel, angled, or axially offset relative to the first longitudinal axis 4214 of the first rod 50, 70. Once the desired orientation of the integrated rod 1210 relative to the first rod 50, 70 is achieved, the set screw 1222 may be tightened to secure headed rod 1200 to the connector 4200 and secure the relative position of the headed rod 1200 relative to the connector 4200.

Connector 4200 can be used, for example, in a revision procedure to add a new construct to an existing construct or may be used in a first or single procedure. By way of example, as shown in FIG. 101D, an existing construct may be comprised of rod 70 secured to the spine by a plurality of fasteners 60 (e.g., tulip style polyaxial pedicle screws). In between two existing fasteners 60 or adjacent an existing fastener, for example, connector 4200 may be connected to the existing construct. In particular, opening 4212 of the first clamping portion 4210 of connector 4200 can be inserted over rod 70 of the existing construct. First clamping portion 4210 can be secured to rod 70 by rotating set screw 4226 and advancing clamp 4240 to the locked position (FIG. 101C) to secure rod 70 to first clamping portion 4210. In the embodiment shown, headed rod 1200 can be attached to the modular connector 4250 and secured thereto as described herein. It is also envisioned that other modular connectors, such as tulip 72 may be connected to the modular connector 4250 to revise the existing construct. The free end of the headed rod 1200 or additional rod 50, 70 (when tulip 72 is used) can be secured by one or more additional fasteners 60, thereby securing a new spinal construct to the existing spinal construct. Although one variation is depicted, it is envisioned that different configurations of rods and connectors may be selected by a surgeon or one of skill in the art.

The connectors described herein offer versatility in connecting spinal rod implants together. In the case of an existing construct being accessed in a revision surgery, the new fixation constructs may be attached without the need to remove the original surgical hardware. Attaching directly to existing spinal rod constructs saves operating time, causes less disruption to the patient, and improves patient healing times. The connectors maximize utility in cases of varying patient anatomy and different configurations for existing constructs. The different connection modes offer a wide range of options for improved patient outcomes.

It will be further understood that various changes in the details, materials, and arrangements of the parts which have been described and illustrated in order to explain the nature of this invention may be made by those skilled in the art without departing from the scope of the invention as expressed in the claims.

What is claimed is:

1. A modular connector system comprising:
   a connector having a body having an upper surface, a lower surface, and a side surface connecting the upper surface and the lower surface, the body having a first clamping portion and a second modular portion;
   the first clamping portion having:
      a first passage having a first longitudinal axis extending therethrough such that the longitudinal axis extends in a direction from the upper surface to the lower surface,
      the first passage being sized to allow a first rod to be inserted therein;
      a bottom portion having an opening in communication with the first passage; and
      a first securing mechanism comprising a set screw, a clamp having two opposing legs, and an opening defined between the two opposing legs, the clamp being connected to the set screw and the set screw being rotatably connected to the body, the first securing mechanism having an unlocked position configured to receive the first rod and a locked position configured to releasably secure the first rod in the opening between the two opposing legs of the clamp and in the first passage; and
   the second modular portion having:
      a post extending from the body away from the lower surface and having a second longitudinal axis that is parallel to the first longitudinal axis, the post having a partially spherical outer surface,
   wherein the legs of the clamp of the first securing mechanism do not extend beyond the lower surface of the body when the securing mechanism is in the unlocked position and the locked position,
   wherein the two opposing legs move inwardly toward one another as the clamp is driven upward in the body to the locked position by rotation of the set screw, and
   wherein the set screw is able to rotate independently from the clamp.

2. The system according to claim 1, wherein the post has a flat upper surface and an opening extending therein.

3. The system according to claim 1, wherein the post is configured to receive a plurality of different modular connectors.

4. The system according to claim 3, wherein each modular connector is configured to articulate relative to the body of the connector.

5. The system according to claim 1, further comprising a tulip-style assembly coupled to the post.

6. The system according to claim 1, further comprising a headed rod coupled to the post.

7. The system according to claim 1, wherein the first passage is defined by generally opposing sidewalls having one or more angled surfaces.

8. The system according to claim 1, wherein an annular protrusion on an engagement end of the set screw is received in a recess in a top portion of the clamp.

9. A modular connector system comprising:
   a connector having a body having an upper surface, a lower surface, and a side surface connecting the upper surface and the lower surface, the body having a first clamping portion and a second modular portion;
   the first clamping portion having:
      a first passage having a first longitudinal axis extending therethrough such that the longitudinal axis extends in a direction from the upper surface to the lower surface,
      the first passage being sized to allow a first rod to be inserted therein;
      a bottom portion having an opening in communication with the first passage; and
      a first securing mechanism comprising a set screw, a clamp having two opposing legs, and an opening defined between the two opposing legs, the clamp being connected to the set screw and the set screw being rotatably connected to the body, the first securing mechanism having an unlocked position configured to receive the first rod and a locked position configured to releasably secure the first rod in the opening between the two opposing legs of the clamp and in the first passage; and
   the second modular portion having:
      a post extending from the body away from the lower surface and having a second longitudinal axis that is parallel to the first longitudinal axis, the post having a partially spherical outer surface,
   wherein the legs of the clamp of the first securing mechanism do not extend beyond the lower surface of the body when the securing mechanism is in the unlocked position and the locked position, and
   wherein the two opposing legs move inwardly toward one another as the clamp is driven upward in the body to the locked position by rotation of the set screw.

10. The system according to claim 9, wherein the post has a flat upper surface and an opening extending therein.

11. The system according to claim 9, wherein the post is configured to receive a plurality of different modular connectors, and wherein the modular connector is configured to articulate relative to the body of the connector.

12. The system according to claim 11, wherein the modular connector is a tulip-style assembly.

13. The system according to claim 11, wherein the modular connector is a headed rod.

14. The system according to claim 13, wherein the headed rod extends from a first end having a modular connection point to a second end terminating at a distal free end.

15. The system according to claim 9, wherein the first passage is defined by generally opposing sidewalls having one or more angled surfaces.

16. The system according to claim 9, wherein an annular protrusion on an engagement end of the set screw is received in a recess in a top portion of the clamp.

* * * * *